(12) United States Patent
Baba et al.

(10) Patent No.: US 8,542,444 B2
(45) Date of Patent: Sep. 24, 2013

(54) IMAGE PICKUP OPTICAL SYSTEM FOR CAPSULE ENDOSCOPE

(75) Inventors: Tomoyuki Baba, Saitama (JP); Hitoshi Miyano, Saitama (JP)

(73) Assignee: FUJIFILM Corporation, Tokyo (JP)

( * ) Notice: Subject to any disclaimer, the term of this patent is extended or adjusted under 35 U.S.C. 154(b) by 60 days.

(21) Appl. No.: 13/257,518

(22) PCT Filed: Mar. 24, 2010

(86) PCT No.: PCT/JP2010/055140
§ 371 (c)(1),
(2), (4) Date: Sep. 19, 2011

(87) PCT Pub. No.: WO2010/110349
PCT Pub. Date: Sep. 30, 2010

(65) Prior Publication Data
US 2012/0016199 A1    Jan. 19, 2012

(30) Foreign Application Priority Data

Mar. 24, 2009  (JP) .................................. 2009-071918
Mar. 25, 2009  (JP) .................................. 2009-074546

(51) Int. Cl.
*G02B 3/00*  (2006.01)
*A61B 1/05*  (2006.01)
*A61M 39/02*  (2006.01)

(52) U.S. Cl.
CPC ... *G02B 3/00* (2013.01); *A61B 1/05* (2013.01); *A61M 2039/0279* (2013.01)
USPC ............................. 359/642; 600/101; 600/109

(58) Field of Classification Search
USPC ................. 359/656–661, 811–822, 642, 725; 600/112, 168, 176; D4/138
See application file for complete search history.

(56) References Cited

U.S. PATENT DOCUMENTS 6,939,295 B2 *  9/2005  Yokoi et al. ................... 600/176
7,317,180 B2 *  1/2008  Konno et al. .............. 250/208.1
(Continued)

FOREIGN PATENT DOCUMENTS

JP        7-181377 A     7/1995
JP        2006-61438 A   3/2006
(Continued)

OTHER PUBLICATIONS

First Office Action, dated Jan. 14, 2013, issued in corresponding CN Application No. 201080013445.3, 12 pages in English and Chinese.

*Primary Examiner* — Ricky Mack
*Assistant Examiner* — William Alexander
(74) *Attorney, Agent, or Firm* — Sughrue Mion, PLLC

(57) ABSTRACT

A capsule endoscope includes an image pickup optical system for imaging an object. The image pickup optical system satisfies a condition expressed by $-5 \leq \Delta Zr/\Delta Zp \leq 5$. Assuming $\omega max$ is a maximum half angle of view, $\Delta Zr$ is a difference between a position of a real image surface with respect to light flux of $2\omega max$ and that with respect to light flux of $\omega max$, and $\Delta Zp$ is a difference between a paraxial image forming position of a first virtual object plane surface and that of a second virtual object plane surface. The first virtual object plane surface passes through an intersection point P1 of the object and principal rays of $2\omega max$. The second virtual object plane surface passes through an intersection point of the object and principal rays of $\omega max$. The first and second virtual object planes are vertical to the optical axis.

6 Claims, 34 Drawing Sheets

(56) References Cited

U.S. PATENT DOCUMENTS

| | | | |
|---|---|---|---|
| 7,465,271 B2 * | 12/2008 | Kanazawa | 600/179 |
| 7,542,218 B2 * | 6/2009 | Togino | 359/725 |
| 7,561,351 B2 * | 7/2009 | Konno | 359/811 |
| 7,701,650 B2 * | 4/2010 | Lin | 359/793 |
| 7,955,276 B2 * | 6/2011 | Yoshino | 600/587 |
| 8,254,038 B2 * | 8/2012 | Togino | 359/725 |
| 2005/0054901 A1 * | 3/2005 | Yoshino | 600/176 |
| 2005/0054902 A1 * | 3/2005 | Konno | 600/176 |
| 2005/0288557 A1 * | 12/2005 | Yokoi et al. | 600/176 |
| 2006/0114575 A1 | 6/2006 | Togino et al. | |
| 2007/0118017 A1 * | 5/2007 | Honda | 600/160 |
| 2009/0099416 A1 * | 4/2009 | Yoshino | 600/109 |
| 2009/0273666 A1 * | 11/2009 | Konno et al. | 348/65 |
| 2009/0278920 A1 | 11/2009 | Kamo | |
| 2009/0306477 A1 * | 12/2009 | Togino | 600/176 |
| 2009/0310230 A1 * | 12/2009 | Togino | 359/725 |
| 2010/0110564 A1 * | 5/2010 | Togino | 359/725 |
| 2011/0169931 A1 * | 7/2011 | Pascal et al. | 348/68 |
| 2011/0286112 A1 * | 11/2011 | Orihara et al. | 359/716 |

FOREIGN PATENT DOCUMENTS

| | | | |
|---|---|---|---|
| JP | 2006-243689 A | | 9/2006 |
| JP | 4128504 B2 | | 7/2008 |
| JP | 4128505 B2 | | 7/2008 |
| JP | 2008-309859 A | | 12/2008 |
| JP | 2009-276371 A | | 11/2009 |
| WO | WO 2008-004377 | * | 1/2008 |

* cited by examiner

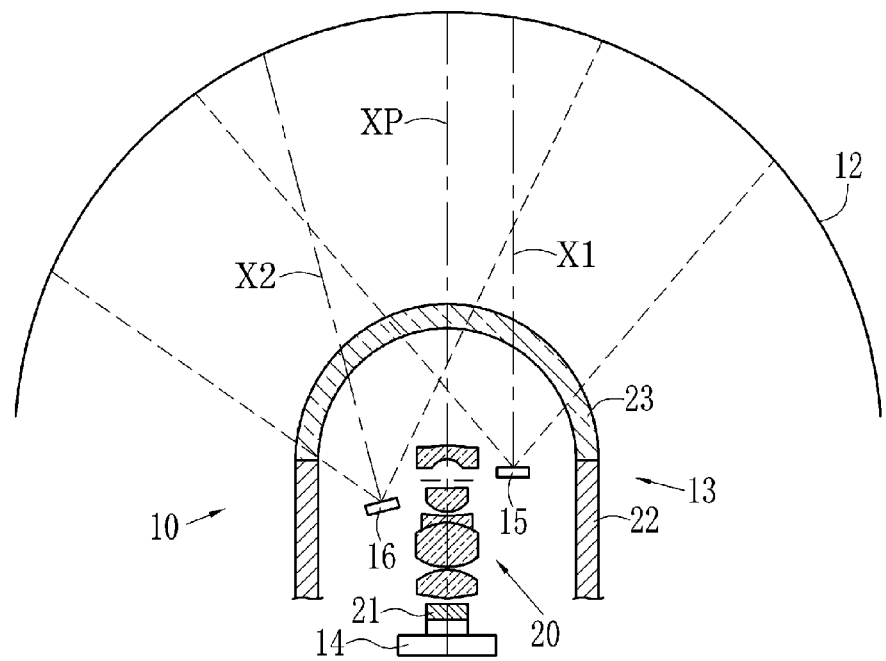
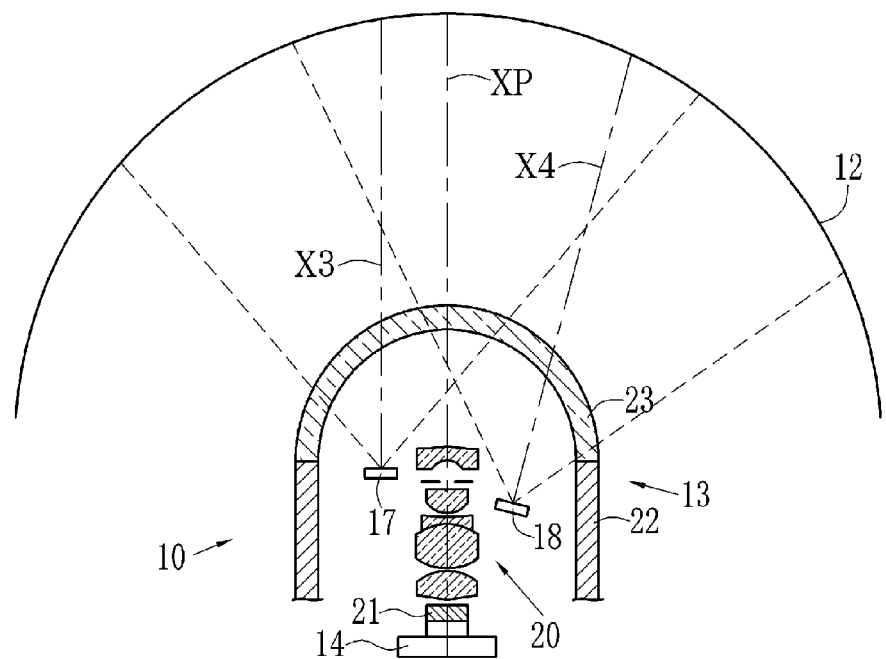

$(Y(\omega+\Delta\omega)-Y(\omega))/Y(\Delta\omega)$ $(Y(\omega+\Delta\omega)-Y(\omega))/Y(\Delta\omega)$

SPHERICAL ABERRATION     ASTIGMATISM     CHROMATIC ABERRATION OF MAGNIFICATION $(Y(\omega + \Delta\omega) - Y(\omega))/Y(\Delta\omega)$ $(Y(\omega+\Delta\omega)-Y(\omega))/Y(\Delta\omega)$

SPHERICAL ABERRATION    ASTIGMATISM    CHROMATIC ABERRATION OF MAGNIFICATION $(Y(\omega+\Delta\omega)-Y(\omega))/Y(\Delta\omega)$

SPHERICAL ABERRATION     ASTIGMATISM     CHROMATIC ABERRATION OF MAGNIFICATION $(Y(\omega+\Delta\omega)-Y(\omega))/Y(\Delta\omega)$

SPHERICAL ABERRATION    ASTIGMATISM    CHROMATIC ABERRATION OF MAGNIFICATION $(Y(\omega+\Delta\omega)-Y(\omega))/Y(\Delta\omega)$

IMAGE PICKUP OPTICAL SYSTEM FOR CAPSULE ENDOSCOPE

CROSS REFERENCE TO RELATED APPLICATIONS

This application is a National Stage of International Application No. PCT/JP2010/055140, filed on Mar. 24, 2010, which claims priority from Japanese Patent Application Nos. 2009-071918, filed on Mar. 24, 2009, and 2009-074546, filed Mar. 25, 2009, the contents of all of which are incorporated herein by reference in their entirety.

TECHNICAL FIELD

The present invention relates to an image pickup optical system for use in a capsule endoscope which is used in a manner that a patient swallows it.

BACKGROUND ART

Recently, in a medical field, diagnosis has been conducted by means of an insertion-type endoscope having a long insertion portion provided with an imaging device at its front end, and a capsule endoscope in which an imaging device is accommodated in a capsule. The capsule endoscope is formed so as to have a size swallowable for a subject under inspection. Therefore, the capsule endoscope has an advantage in that it can remove not only the load on a patient at the time of swallowing the insertion portion of the insertion-type endoscope but also the load on a patient while the insertion portion of the insertion-type endoscope is kept being inserted in a body cavity of the patient for many hours.

The capsule endoscope is provided with a dome-shaped transparent cover at its front end so as to readily advance along a tubular channel after being swallowed into the body cavity, and a cylindrical capsule main body is connected to the transparent cover. An optical axis of an image pickup optical system is generally designed to pass through a center of the transparent cover. Accordingly, the image pickup optical system receives not only light flux near the optical axis but also light flux made incident thereon with a large incident angle through a peripheral portion of the transparent cover. Further, an object distance tends to be longer on the optical axis, and tends to be shorter as an angle of view in imaging becomes wider. Therefore, in the general image pickup optical system in which an image of a planar object is formed on a planar image pickup surface vertical to the optical axis, a range in which preferable image-forming can be achieved is extremely limited.

Under the circumstances described above, an image pickup optical system having a wide angle of view is known as is disclosed in Patent Document 1. However, if a peripheral portion of the object is made to be in focus in the optical design, a central portion of the object falls outside of the depth of field to be out of focus. In contrast, if the central portion of the object is made to be in focus excessively, the peripheral portion of the object falls outside of the depth of field to be out of focus. As the countermeasure of such a problem, according to an image pickup optical system disclosed in Patent Documents 2 and 3, the image surface is made to coincide with the neighborhood of the image pickup surface in the center of a screen at the maximum angle of view, such that the entire object including not only its central portion but also its peripheral portion falls within the depth of field.

PRIOR ART DOCUMENTS

Patent Documents
 Patent Document 1: JP 2006-61438 A
 Patent Document 2: JP 4128504 B
 Patent Document 3: JP 4128505 B

SUMMARY OF INVENTION

Problems to be Solved by the Invention

Not only light flux from an optical axis and its periphery, but also light flux made incident on the optical axis with a large incident angle through the periphery of a transparent cover contains much useful information for diagnosis in the capsule endoscope, and therefore an image pickup optical system is required to have a wide angle of view. With regard to this point, according to the image pickup optical system disclosed in Patent Documents 2 and 3, although the relation between the angle of view and the object distance which is required for the capsule endoscope is optimized, the angle of view is 113.6° at most. The angle of view of 113.6° is at an insufficient level. Further, in the above Patent Documents, although the optical system adopting a front aperture stop has an advantage in suppressing an outer diameter of the lens at an object side to small, it has a disadvantage as follows. In the optical system adopting the front aperture stop, the thickness of the aperture stop causes vignetting in the light beam, or a radius of curvature of a lens surface just behind the aperture stop is large, thus leading to large loss of light amount when the angle of view becomes wider.

In order to focus the object having a concave surface toward the image pickup optical system on a plane image pickup surface vertical to the optical axis, it is sufficient to generate negative curvature of field in the optical system. Further, in order to control the curvature of field as described above, it is sufficient to increase Petzval sum by the third aberration coefficient at a positive value. In order to generate negative curvature of field in the optical system, it is general that low refractive-index material is used for the positive lens and high refractive-index material is used for the negative lens in the optical system. However, when it is taken into consideration that a plastic lens is used for the image pickup optical system of the capsule endoscope which is to be used only once basically for the purpose of achieving low cost, it becomes hard to obtain the high refractive-index material, and adjustment of the Petzval sum becomes difficult. Note that, it is also possible to give flexibility to the adjustment of the Petzval sum by increasing the number of the lenses, however, in such a case, the total length of the optical system becomes long and the capsule inevitably becomes long and large. Accordingly, it is difficult to adopt the above countermeasure to the capsule endoscope which is used in a manner that a patient swallows it.

Means for Solving the Problems

In view of the above, an object of the present invention is to provide an image pickup optical system for use in a capsule endoscope capable of widening an angle of view and making the image surface coincide with the neighborhood of the image pickup surface vertical to an optical axis over the whole angle of view, such that the almost whole object which is curved so as to be concave toward the image pickup optical system is within the depth of field.

In order to achieve the above object, an image pickup optical system of the present invention is configured to satisfy a condition expressed by $-5.0 \leq \Delta Zr/\Delta Zp \leq 5.0$ when the image pickup optical system is disposed in front of an object in the shape of concave curved surface and the image capturing is performed. Note that, $\Delta Zr$ denotes a difference between a position of a real image surface with respect to light flux of a maximum angle of view 2ωmax and a position of the real image surface with respect to light flux of a half angle of view ωmax. Δ Zp denotes a difference between a paraxial image forming position of a virtual object plane surface passing through an intersection point of the object and principal rays of 2ωmax and being vertical to an optical axis and that of a virtual object plane surface passing through an intersection point of the object and principal rays of ωmax and being vertical to the optical axis. The above condition is preferably suitable for an optical system in which the maximum angle of view 2ωmax is set to at least 135°. In the case where the maximum angle of view 2ωmax of the optical system is set to 120°, the upper limit and the lower limit of the above condition preferably satisfies $-0.5 \leq \Delta Zr/\Delta Zp \leq 0.5$.

The reason why the condition for the value of $\Delta Zr/\Delta Zp$ changes is as follows. The depth of field of the image pickup optical system is generally defined by a diameter of circle of confusion. However, practically, as the distance toward the object becomes longer, the image of the object becomes smaller on the image surface, and therefore high resolving power is required, and in contrast, as the distance toward the object becomes shorter, magnification of image is increased, and therefore the required resolving power is not so high as that for the long-distance object. The image pickup optical system of the present invention is configured in consideration of the type of usage specific to the capsule endoscope in which as the distance toward the object becomes shorter, the incident angle of the light beam becomes larger, and as the distance toward the object becomes longer, the incident angle of the light beam becomes smaller. Accordingly, as the imaging angle of view becomes narrower, the number of long-distance objects on an imaging screen is increased, and high resolving power is required. Therefore, it is necessary to narrow the condition of the $\Delta Zr/\Delta Zp$.

It is possible to widen the angle of view of the optical system by increasing distortion toward the minus side. However, in such a case, when the short-distance object in the peripheral portion of the image is desired to be captured successfully as in the case of the present invention, the distortion makes the image distorted largely, and thus magnification of image is decreased. Therefore, it becomes difficult to sufficiently improve image forming properties with respect to the light flux from the short-distance object with a large incident angle. In this regard, in the image pickup optical system of the present invention, the relation expressed by $0.7 < (Y(\omega+\Delta\omega)-Y(\omega))/Y(\Delta\omega)$ is satisfied, in which $Y(\Delta\omega)$ denotes an image height at an arbitrary angle of view ω, and Δω denotes an amount of slight change in the arbitrary angle of view ω. Accordingly, it is also possible to prevent the images from being distorted by the distortion to a level causing no problem in practical use, thus exhibiting preferable image forming properties.

In order to achieve curvature of field specific to the image pickup optical system of the present invention, a negative lens which is convex toward the object is preferably disposed at a position nearest to the object. Further, it is advantageous that at least a surface of the negative lens at a side near to the object is aspherical as well as at least one of surfaces of the positive lens disposed at a position nearest to an image surface is aspherical, in view of cost and shortening of the total length of the optical system. Note that, the convex surface of the negative lens at the side nearer to the object does not always have to be a convex surface whose top is protruded most, and may be an aspheric surface in which the paraxial area is concave and the outer peripheral area is curved so as to approach the image surface, for example.

Since such a negative lens is used at the position nearest to the object, the light beams made incident with a large angle from the periphery are emitted with a small angle with respect to the optical axis due to the initial negative power, and the incident angle with respect to the aperture stop becomes smaller. Accordingly, loss of light amount due to the thickness of the aperture stop can be decreased in comparison with the optical system having a front aperture stop. At the back of the negative lens is disposed the positive lens group constituted of a plurality of lenses and having a positive power as a whole. If the lens at the position nearest to the object and the lens at the position nearest to the image surface in the positive lens group are positive lenses so as to distribute the positive power, the curvature of field can be readily adjusted while the aberration occurred in the negative lens is corrected.

Effect of the Invention

According to the present invention, it is possible to widen the angle of view and make the image surface coincide with the neighborhood of the image pickup surface vertical to the optical axis over the whole angle of view such that the entire object is within the depth of field. Thus, a brilliant image of a lesion which is not out of focus can be obtained, wherever the lesion exists in the object.

BRIEF DESCRIPTION OF DRAWINGS

FIG. 1 is a cross sectional view of a capsule endoscope of the present invention.

FIG. 2 is a cross sectional view of the capsule endoscope of FIG. 1 rotated by 90° along an optical axis.

MODE FOR CARRYING OUT THE INVENTION

Figure 3:
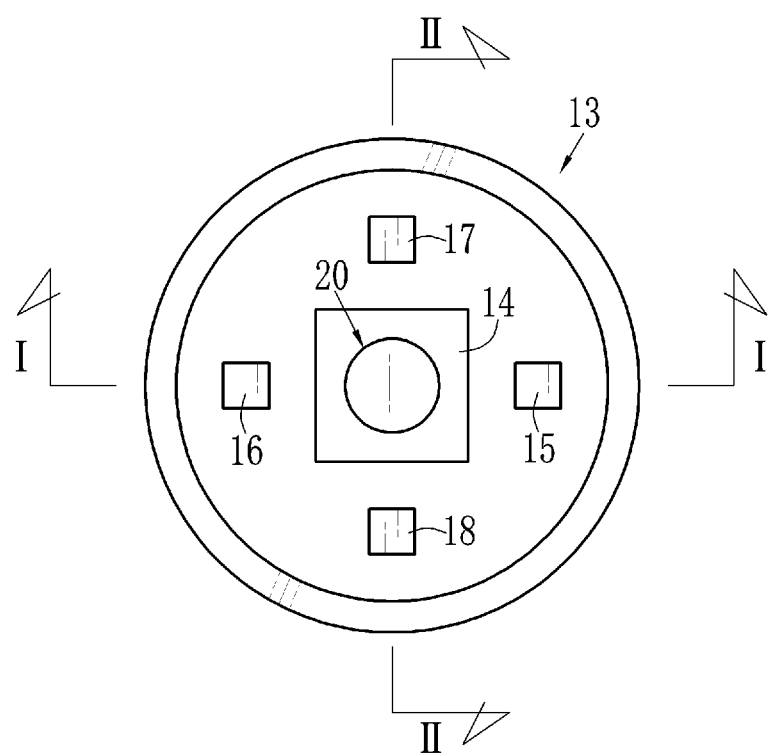
FIG. 3 is a plane view of four LEDs disposed in a capsule.

FIG. 1 shows only a front part of a capsule endoscope 10. The capsule endoscope 10 is in the form of capsule having a size of around ten millimeters in diameter and around twenty millimeters in length, such that a subject under inspection easily swallows it. The capsule endoscope 10 captures images of interior of the stomach, intestine, and the like at a fixed time interval from the time when the capsule endoscope 10 is swallowed by the subject under inspection to the time when the capsule endoscope 10 is discharged outside the body of the subject. An image pickup optical system of the present invention installed into the capsule endoscope 10 has a function of successfully forming an image of an object 12 on a plane vertical to an optical axis, on the assumption that the object 12 is in the shape of concave hemisphere surface. Note that, the object 12 does not always have to be in the shape of complete concave hemisphere surface, and may be another concave curved surface.

FIG. 2 shows the capsule endoscope 10 rotated by 90° about a central axis thereof. In FIGS. 1 and 2, an outer package of the capsule endoscope 10 is a capsule 13. An opaque capsule main body 22 of the capsule 13 has a closed rear end and a front end provided with a dome-shaped transparent cover 23. The capsule 13 contains an area-type image pickup device 14 whose front surface is provided with a cover glass 21, first to fourth LEDs (Light Emitting Diodes) 15 to 18 as illumination sources, and an image pickup optical system 20. Further, the capsule 13 contains a battery for driving the image pickup device 14, and an antenna for transmitting image signals obtained by the image pickup device 14 to a receiver attached to the periphery of the subject under inspection (both of them being omitted in the drawing). The image pickup optical system 20 forms an image of object light received through the powerless transparent cover 23 on an image pickup surface of the image pickup device 14.

FIG. 3 shows the capsule endoscope 10 as seen from its front through the transparent cover 23. As shown in FIG. 3, the first to fourth LEDs 15 to 18 are disposed around the image pickup optical system 20 so as to be apart from each other with a pitch of about 90°. The second and fourth LEDs 16 and 18 are shifted toward the image pickup device 14 in a direction of an optical axis XP of the image pickup optical system 20 in comparison with the first and third LEDs 15 and 17. The first and third LEDs 15 and 17 are disposed such that an illumination optical axis X1 of the first LED 15 and an illumination optical axis X3 of the third LED 17 are parallel to the optical axis XP of the image pickup optical system 20, respectively. The first and third LEDs 15 and 17 illuminate mainly a central portion of the object 12 including its center portion and peripheral portion. Further, the second and fourth LEDs 16 and 18 are disposed such that an illumination optical axis X2 of the second LED 16 and an illumination optical axis X4 of the fourth LED 18 are inclined by a certain angle with respect to the optical axis XP of the image pickup optical system 20. The second and fourth LEDs 16 and 18 illuminate mainly a peripheral portion of the object 12 extending from the central portion of the object 12 to the edges thereof.

Accordingly, it is possible to apply illumination light uniformly toward almost allover the object 12 which is in the shape of concave hemisphere surface. Additionally, even if each of the LEDs 15 to 18 applies illumination light toward the object 12 in the capsule 13, flare does not appear.

Figure 4:
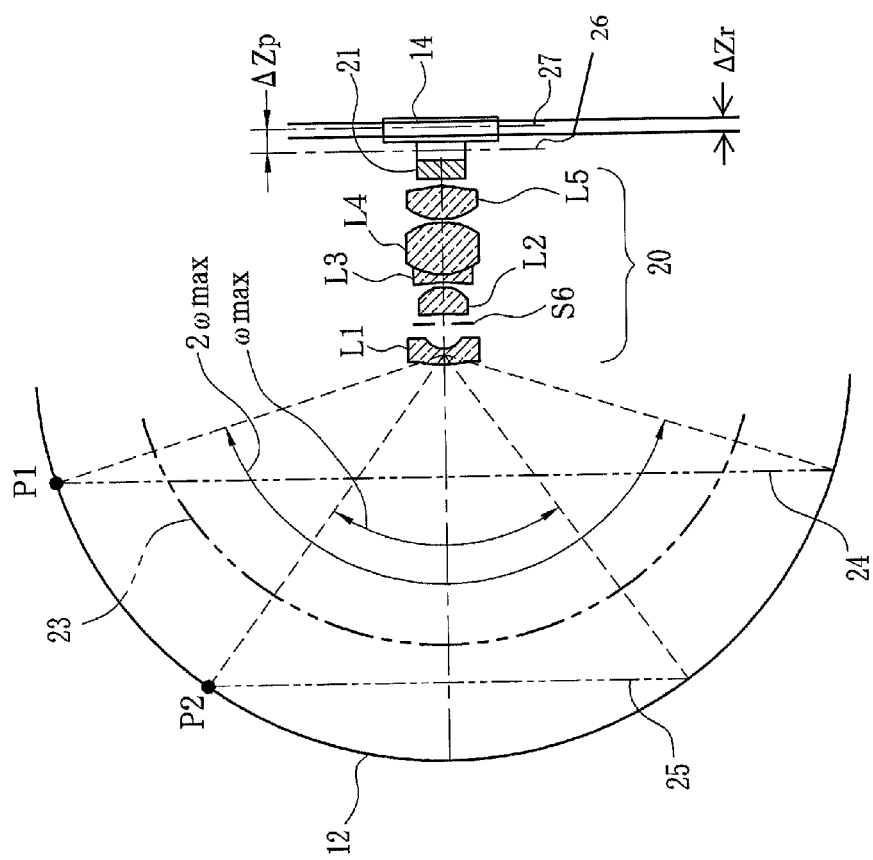
FIG. 4 is an explanatory view about mathematical expression 1.

As shown in FIG. 4, the image pickup optical system 20 consists of a first lens L1, an aperture stop S6, a second lens L2, a third lens L3, a fourth lens L4, and a fifth lens L5, which are disposed in this order from the side of the object 12. Note that, in FIG. 4, in order to avoid complexity of the drawing, the LEDs 15 to 18 are omitted, and a front surface of the transparent cover 23 is shown by a chain double-dashed line. The image pickup optical system 20 has negative curvature of field, and a function of successfully forming an image of the concave object 12 on an image pickup surface vertical to the optical axis XP. For the purpose of achieving such image forming properties, in the image pickup optical system 20, the first lens L1 is basically a negative lens which is convex toward the object 12, and preferably at least a surface of the first lens L1 facing the object 12 is designed to be aspherical. Further, any one of surfaces of the fifth lens L5 is designed to be aspherical, too.

As the difference between the position of a real image surface on the optical axis XP with respect to light flux of a maximum angle of view ($2\omega max$) and that with respect to light flux of a maximum half angle of view ($\omega max$) is smaller, the image forming properties are regard to be more preferable. A virtual plane 24 is configured to pass through an intersection point P1 of the object 12 and principal rays with the maximum angle of view ($2\omega max$) and to be vertical to the optical axis XP. A virtual plane 25 is configured to pass through an intersection point P2 of the object 12 and principal rays with the maximum half angle of view ($\omega max$) and to be vertical to the optical axis XP. As the difference between one of paraxial image forming positions 26 and 27 of the virtual plane 24 and the other of paraxial image forming positions 26 and 27 of the virtual plane 25 is smaller, the image forming properties are regard to be more preferable. In particular, when the maximum angle of view ($2\omega max$) of the image pickup optical system 20 is at least 120°, the image pickup optical system 20 is designed such that the following mathematical expression 1 is satisfied.

$$-0.5 \leq \frac{\Delta Z_r}{\Delta Z_p} \leq 0.5 \qquad \text{[Mathematical Expression 1]}$$

In the mathematical expression 1, when the maximum angle of view of the image pickup optical system 20 is denoted by $2\omega max$ and the maximum half angle of view thereof is denoted by $\omega max$, $\Delta Zr$ and $\Delta Zp$ denote as follows.

$\Delta Zr$: Difference between the position of the real image surface with respect to the light flux of $2\omega max$ and that with respect to the light flux of $\omega max$.

$\Delta Zp$: Difference between the paraxial image surface position of the virtual object plane surface 24 and that of the virtual object plane surface 25, in which the virtual object plane surface 24 passes through the intersection point P1 of the object 12 and principal rays of $2\omega max$ and is vertical to the optical axis XP, and virtual object plane surface 25 passes through the intersection point P2 of the object 12 and principal rays of $\omega max$ and is vertical to the optical axis XP.

When the image pickup optical system 20 satisfies the condition of the mathematical expression 1, the curvature of field can be sufficiently corrected, and the whole object 12 including the central portion of the concave hemisphere surface and the peripheral portion thereof is within the depth of field of the image pickup optical system 20. Thereby, since it is possible to obtain brilliant images in which both the central portion of the image and the peripheral portion thereof are in focus, even if a lesion exists in the peripheral portion of the image, the lesion can be found with absolute accuracy.

When $\Delta Zr/\Delta Zp$ is less than −0.5, due to the effect by the curvature of field of the image pickup optical system 20, the position of the real image surface with respect to the light flux of $2\omega max$ is significantly deviated toward the object 12 in comparison with the position of the real image surface with respect to the light flux of $\omega max$. In contrast, when $\Delta Zr/\Delta Zp$ is more than 0.5, due to the effect by the object 12 being in the shape of concave curved surface, the position of the real image surface with respect to the light flux of $2\omega max$ is significantly deviated toward an opposite side of the object 12 in comparison with the position of the real image surface with respect to the light flux of $\omega max$. In any cases, the real image surface with respect to the light flux of $2\omega max$ and that with respect to the light flux of $\omega max$ are significantly deviated in the direction of the optical axis XP, and therefore it becomes impossible to successfully form images of both of the real image surfaces on the image pickup surface vertical to the optical axis XP. Accordingly, in the image pickup optical system 20 in which the maximum angle of view ($2\omega max$) is at least 120°, it is preferable to satisfy the condition expressed by ABS ($\Delta Zr/\Delta Zp$)$\leqq 0.5$. Note that, ABS represents the absolute value of the value in brackets.

When the maximum angle of view ($2\omega max$) of the image pickup optical system 20 is further widen so as to be at least 135°, the value of ABS ($\Delta Zr/\Delta Zp$) can be liberalized and may be set within the range satisfying the following mathematical expression 2.

$$-5.0 \leq \frac{\Delta Z_r}{\Delta Z_p} \leq 5.0 \qquad \text{[Mathematical Expression 2]}$$

Note that, what the $\Delta Zr$ represents and what the $\Delta Zp$ represents in the mathematical expression 2 are common to those in the mathematical expression 1 described above. In the case where $\Delta Zr/\Delta Zp$ is less than −5.0 as a lower limit in the mathematical expression 2, there is exhibited the tendency common to that in the case where $\Delta Zr/\Delta Zp$ is less than −0.5 as the lower limit in the mathematical expression 1. In the case where $\Delta Zr/\Delta Zp$ is more than 5.0 as an upper limit in the mathematical expression 2, there is exhibited the tendency common to that in the case where $\Delta Zr/\Delta Zp$ is more than the upper limit in the mathematical expression 1. Accordingly, in the image pickup optical system 20 in which the maximum angle of view ($2\omega max$) is at least 135°, it is preferable to satisfy the condition expressed by ABS ($\Delta Zr/\Delta Zp$)$\leqq 5.0$.

Moreover, either when the maximum angle of view ($2\omega max$) is at least 120° or when the maximum angle of view ($2\omega max$) is at least 135°, the image pickup optical system 20 is configured to satisfy the following mathematical expression 3 in which an image height when the angle of view is ($\omega$) is denoted by Y($\omega$). Note that, the following mathematical expression 3 may be satisfied under the condition that the angle of view is at most 45°.

$$0.7 < \frac{Y(\omega + \Delta\omega) - Y(\omega)}{Y(\Delta\omega)} \qquad \text{[Mathematical Expression 3]}$$

"Y(ω+Δω)−Y(ω)" in the mathematical expression 3 represents the difference between the image height Y(ω+Δω) when the angle of view slightly changes from ω to Δω (namely, when the angle of view is (ω+Δω)), and the image height Y(ω) when the angle of view is ω. "Y(Δω)" in the mathematical expression 3 represents the difference Y(0+Δω)−Y(0) between the image height Y(Δω) when the angle of view slightly changes from 0° to Δω (namely, when the angle of view is Δω), and the image height Y(0) when the angle of view is 0°. In view of Y(0)=0, it is concluded that Y(0+Δω)−Y(0)=Y(Δω). Accordingly, "(Y(ω+Δω)−Y(ω))/Y(Δω)" in the mathematical expression 3 represents how much distortion is generated in the peripheral portion of the image in comparison with the central portion thereof.

Figure 5C:
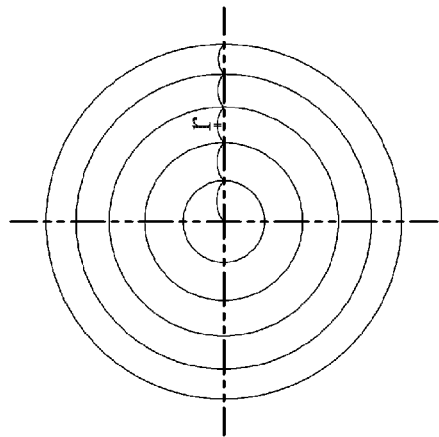
FIGS. 5B to 5E are explanatory views of images obtained by capturing the concentric circles of FIG. 5A.
Figure 5E:
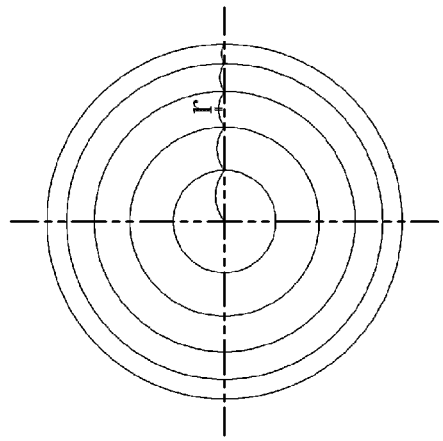

Here, (Y(ω+Δω)−Y(ω))/Y(Δω) denotes distortion index Q, and the image pickup optical system 20 is designed such that the value of distortion index Q becomes "1.0", "0.7", "0.5", and "0.3", respectively. Then, the degree of distortion generated in the image obtained by each of the image pickup optical systems is evaluated. With regard to the evaluation, as shown in FIG. 5A, a plurality of circles (concentric circles) 30a to 30e each having a radius of "r", "2r", "3r", "4r", and "5r" are set on the object 12 such that the center of each of the circles is on the optical axis XP. The concentric circles are respectively captured by each of the image pickup optical system 20. Then, the degree of distortion in the peripheral portion of the image is evaluated based on how the distance between the concentric circles changes in the peripheral portion of the image obtained by the image capturing.

Figure 5B:
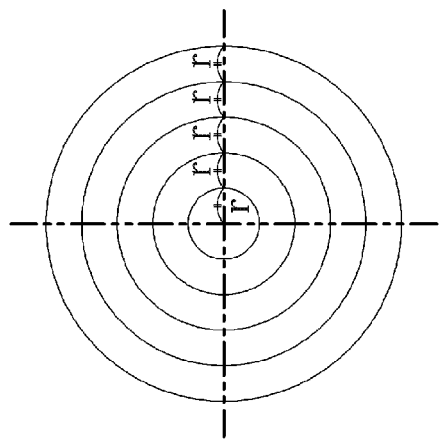

FIG. 5B shows the image captured by the image pickup optical system 20 designed so as to satisfy Q=1.0. As shown by the image, the distance between the circles on the image is denoted by a distance r, as in the case of the distance between the plurality of circles 30a to 30e set on the object 12. In this way, when the distance between the circles in the central portion of the image is the same as the distance between the circles in the peripheral portion of the image, it is concluded that the distortion does not occur in the peripheral portion of the image. Accordingly, if the body cavity of the subject under inspection is captured by using the capsule endoscope 10 incorporating the above image pickup optical system 20, the distortion hardly occur in the peripheral portion of the image, and therefore it becomes easy to recognize the lesion.

FIG. 5C shows the image captured by the image pickup optical system 20 designed so as to satisfy Q=0.7. As shown by the image, the distance between the circles in the central portion of the image is slightly larger than the radius r, and the distance between the circles in the peripheral portion of the image is slightly smaller than the radius r. However, the difference therebetween is negligible, and therefore large distortion is not observed in the central portion and the peripheral portion of the image. Accordingly, the image pickup optical system 20 designed so as to satisfy Q=0.7 is considered to be within the satisfactory level in practical use in the image diagnosis.

Figure 5D:
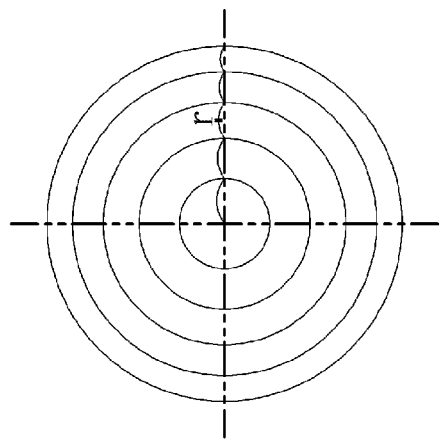
Figure 5A:
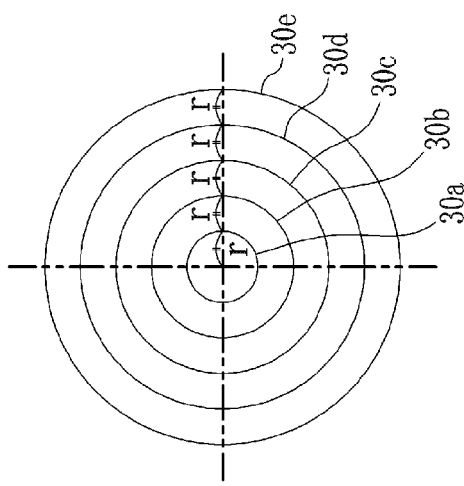
FIG. 5A is an explanatory view of concentric circles provided to a concave hemispherical surface as an object.

FIG. 5D shows the image captured by the image pickup optical system 20 designed so as to satisfy Q=0.5. It can be easily acknowledged from the image that the distance between the circles is large in the central portion of the image, and the distance between the circles is small in the peripheral portion of the image. This tendency is a general feature exhibited in the image pickup optical system having a wide angle of view. However, when distortion of such an extent appears in the image, the image is not suitable for medical diagnosis. There arises a possibility of the lesion being overlooked in the peripheral portion of the image, in particular. Moreover, FIG. 5E shows the image captured by the image pickup optical system designed so as to satisfy Q=0.3. It can be prominently acknowledged from the image that the distance between the circles is large in the central portion of the image, and the distance between the circles is small in the peripheral portion of the image. Accordingly, it is clear that the image pickup optical system designed so as to satisfy Q=0.3 is not suitable for medical diagnosis and is not practical.

In view of the above, either when the maximum angle of view (2ωmax) is at least 120° or when the maximum angle of view (2ωmax) is at least 135°, as far as the image pickup optical system is designed such that the value of distortion index Q, namely, the value of (Y(+Δω)−Y(ω))/Y(Δω) is more than 0.7, it is possible to suppress the distortion in the peripheral portion of the image to a level sufficient for practical use. In the case where the distortion is suppressed in this way, it is possible to surely prevent the lesion from being overlooked even in the peripheral portion of the image, and it becomes possible to increase reliability of image diagnosis. Note that, the value of distortion index Q is preferably more than 0.7 and less than 1.3, and more preferably in the range of more than 0.8 to less than 1.2.

Further, when the image pickup optical system 20 consists of five lenses, namely, the first to fifth lenses, the whole object 12 including its central portion and peripheral portion is within the depth of field of the image pickup optical system 20. Accordingly, a brilliant image in which both of the central portion and the peripheral portion are in focus can be obtained, and distortion in the peripheral portion of the image is at a negligible level. Note that the image pickup optical system 20 is not limited to the configuration composed of five lenses, and may be composed of four lenses, namely, the first to fourth lenses. In the case where the image pickup optical system 20 is composed of four lenses, almost the same effect as that obtained by the image pickup optical system 20 composed of five lenses can be obtained. Furthermore, the image pickup optical system of the present invention can be applied to the image pickup optical system for the capsule endoscope which is swallowed into the body cavity such that the position and the posture thereof in the body cavity at the time of image capturing can be controlled in accordance with control signals received from the outside.

Embodiment

Hereinafter, the present invention is further described in detail by showing concrete numerical values in the following Embodiments 1 to 15 and Comparative Embodiments 1 to 6 as to the image pickup optical system mounted to the capsule endoscope.

[Embodiment 1]

Figure 6:
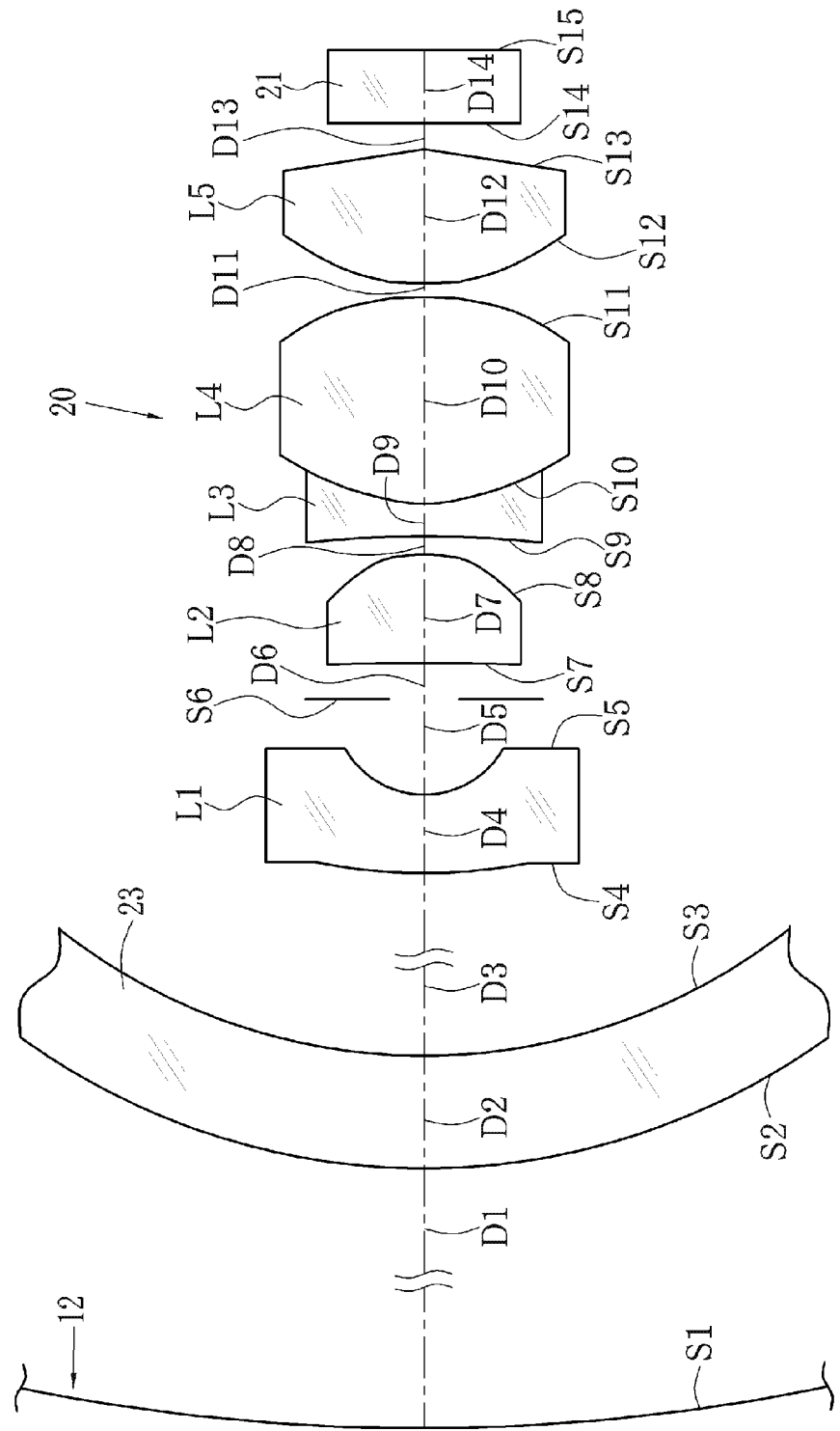
FIG. 6 is a lens configuration diagram of an image pickup optical system according to a first embodiment of the present invention.

As shown in FIG. 6, the image pickup optical system 20 of Embodiment 1 includes five lenses, namely, the first to fifth lenses L1 to L5, and the aperture stop S6. In the capsule 13, the first lens L1, the aperture stop S6, the second lens L2, the third lens L3, the fourth lens L4, and the fifth lens L5 are disposed in this order from the side of the object 12 in the shape of concave hemisphere surface. The third lens L3 and the fourth lens L4 constitute a laminated lens.

The surface of the object 12 is assigned with a number S1, and the surface of each of the components including the transparent cover 23 in the image pickup optical system 20 is assigned with a surface number Si sequentially toward the image surface. Specifically, the front surface of the transparent cover 23 is assigned with S2, and the rear surface thereof is assigned with S3. Subsequently, the surface number Si is assigned in order to the front and rear surfaces of each of the first to fifth lenses L1 to L5, and the rear surface of the cover glass 21 is assigned with a surface number S15. Note that, a joint surface S10 is common to the rear surface of the third lens L3 and the front surface of the fourth lens L4. The rear surface S15 of the cover glass 21 corresponds to the image pickup surface of the image pickup device 14. Additionally, the distance between the surface Si and the surface S(i+1) (surface separation) along the optical axis of the image pickup optical system 20 is denoted by Di. Specifically, the surface separation between the surface S1 and the surface S2 is denoted by D1, and the surface separation between the surface S2 and the surface S3 is denoted by D2. Similarly, the surface separation between the surface S14 and the surface S15 is denoted by D14.

The image pickup optical system 20 is designed based on lens data shown in the following Table 1.

TABLE 1 f = 1.0 Fno = 1.4 2ωmax = 120°

| SURFACE | RADIUS OF CURVATURE | SURFACE SEPARATION | $N_d$ | $v_d$ |
|---|---|---|---|---|
| OBJ | 37.3880 | 24.3625 | | |
| 2 | 13.0255 | 1.9297 | 1.57500 | 32.2 |
| 3 | 11.0958 | 9.8032 | | |
| 4* | 4.5962 | 1.2061 | 1.53039 | 55.2 |
| 5* | 0.7626 | 1.8407 | | |
| APERTURE STOP | ∞ | 0.6628 | | |
| 7* | 29.9508 | 1.9689 | 1.53039 | 55.2 |
| 8* | −2.0294 | 0.2413 | | |
| 9 | −29.3124 | 0.7236 | 1.92286 | 18.9 |
| 10 | 4.8243 | 3.7077 | 1.72916 | 54.7 |
| 11 | −5.0041 | 0.2412 | | |
| 12* | 4.2899 | 2.4120 | 1.53039 | 55.2 |
| 13* | −2.6662 | 0.4704 | | |
| 14 | ∞ | 1.3146 | 1.55920 | 53.9 |
| 15 | ∞ | 0.0000 | | |
| IMG | ∞ | | | |

In Table 1, "OBJ" represents the object 12 in the shape of concave hemisphere surface, "APERTURE STOP" represents the aperture stop S6, "IMG" represents the image pickup surface of the image pickup device 14, "RADIUS OF CURVATURE" represents the radius of curvature (mm) of each of the surfaces Si, "SURFACE SEPARATION" represents each surface separation Di (mm) between the surfaces Si and S(i+1), "Nd" represents refractive index for d line having a wavelength of 587.6 nm, "$v_d$" represents Abbe's number, "f" represents the focal length of the whole image pickup optical system 20, "Fno" represents F value F of the image pickup optical system 20, and "2ωmax" represents the maximum angle of view.

Moreover, as shown by "*" in the column of the surface number in Table 1, the both surfaces S4 and S5 of the first lens, the both surfaces S7 and S8 of the second lens, and the both surfaces S12 and S13 of the fifth lens are aspherical. The aspherical shape is numerically expressed by the following mathematical expression 4 with use of the curvature (the reciprocal of radius of paraxial curvature R) c, the conic constant K, the distance from the optical axis $\rho$ ($\rho^2 = x^2 + y^2$), and the aspherical degree of ith number. The conic constant K and the aspherical constant Ai of the surfaces S4, S5, S7, S8, S12, and S13 are shown in Table 2. Note that, in Embodiments 2 to 15 which will be described later, the notation of the lens data and the mathematical expression 4 for determining the aspherical shape are commonly used.

$$z = \frac{c\rho^2}{1 + \sqrt{1 - (K+1)c^2\rho^2}} + \sum_i A_i \rho^i \quad \text{[Mathematical Expression 4]}$$

$$(\rho^2 = x^2 + y^2)$$

TABLE 2

| SURFACE | K | $A_3$ | $A_4$ | $A_5$ |
|---|---|---|---|---|
| 4 | −1.0000 | −3.1911E−02 | −1.3237E−02 | 2.6667E−03 |
| 5 | −1.0000 | −7.2213E−01 | 1.0601E+00 | −3.2718E−01 |
| 7 | −1.0000 | 6.5178E−03 | −6.7047E−05 | −5.3129E−02 |
| 8 | −1.0000 | −3.8364E−03 | 1.5483E−02 | −1.0465E−02 |
| 12 | −1.0000 | −3.5805E−02 | 4.6875E−02 | −1.4934E−02 |
| 13 | −1.0000 | 7.1495E−02 | 1.7164E−03 | −8.3989E−04 |

| SURFACE | $A_6$ | $A_7$ | $A_8$ | $A_9$ |
|---|---|---|---|---|
| 4 | 1.0090E−03 | 1.6604E−04 | −4.8482E−06 | −1.4417E−05 |
| 5 | −4.1593E−01 | −3.5206E−02 | 2.3279E−01 | 1.6234E−01 |
| 7 | 6.9474E−03 | 3.5489E−02 | −8.0267E−05 | −1.2559E−02 |
| 8 | 1.2919E−03 | −7.6095E−03 | 2.6037E−03 | 1.1487E−03 |
| 12 | −8.0459E−04 | 7.4194E−04 | 1.4060E−04 | −9.2904E−06 |
| 13 | −1.0037E−03 | −4.0258E−04 | −9.5516E−05 | 1.9474E−05 |

| SURFACE | $A_{10}$ | $A_{11}$ | $A_{12}$ | $A_{13}$ |
|---|---|---|---|---|
| 4 | −5.8184E−06 | −1.5724E−06 | −1.6519E−07 | 7.8017E−08 |
| 5 | −5.0788E−02 | −1.4257E−01 | 5.1202E−02 | 1.3674E−02 |
| 7 | −8.5493E−03 | 5.9519E−04 | 1.6546E−02 | −1.0997E−02 |
| 8 | 8.7078E−04 | 2.4020E−05 | −8.3396E−04 | −1.2885E−04 |
| 12 | −9.8806E−06 | −3.2675E−06 | −7.1004E−07 | −3.9997E−08 |
| 13 | 3.7285E−05 | 6.2802E−07 | 3.3755E−07 | −1.8678E−07 |

| SURFACE | $A_{14}$ | $A_{15}$ | $A_{16}$ | $A_{17}$ |
|---|---|---|---|---|
| 4 | 5.7448E−08 | 1.9743E−08 | 1.3443E−09 | −2.2787E−09 |
| 5 | −5.5570E−03 | −5.0334E−05 | 1.6869E−17 | 6.9935E−19 |
| 7 | 1.7577E−03 | 1.2639E−04 | −1.4320E−07 | 4.9356E−09 |

TABLE 2-continued

| 8  | 2.9420E−04  | −2.4577E−05 | −1.2654E−05 | −1.4738E−07 |
|----|-------------|-------------|-------------|-------------|
| 12 | 3.3395E−08  | 2.5653E−08  | 1.1006E−08  | 3.1808E−09  |
| 13 | −1.3249E−07 | −4.0694E−08 | −8.1148E−09 | 1.3025E−09  |

| SURFACE | $A_{18}$ | $A_{19}$ | $A_{20}$ |
|---------|----------|----------|----------|
| 4  | −4.9358E−10 | 1.4347E−10  | 1.6018E−13  |
| 5  | −9.2841E−17 | −5.1143E−16 | −2.1203E−17 |
| 7  | 3.4281E−17  | 9.1722E−19  | 3.8025E−20  |
| 8  | 4.9787E−10  | 1.2020E−21  | 5.8918E−20  |
| 12 | −4.5905E−10 | −3.1571E−10 | −1.5121E−11 |
| 13 | 2.9595E−09  | −1.6047E−10 | −9.2263E−11 |

Figure 7:
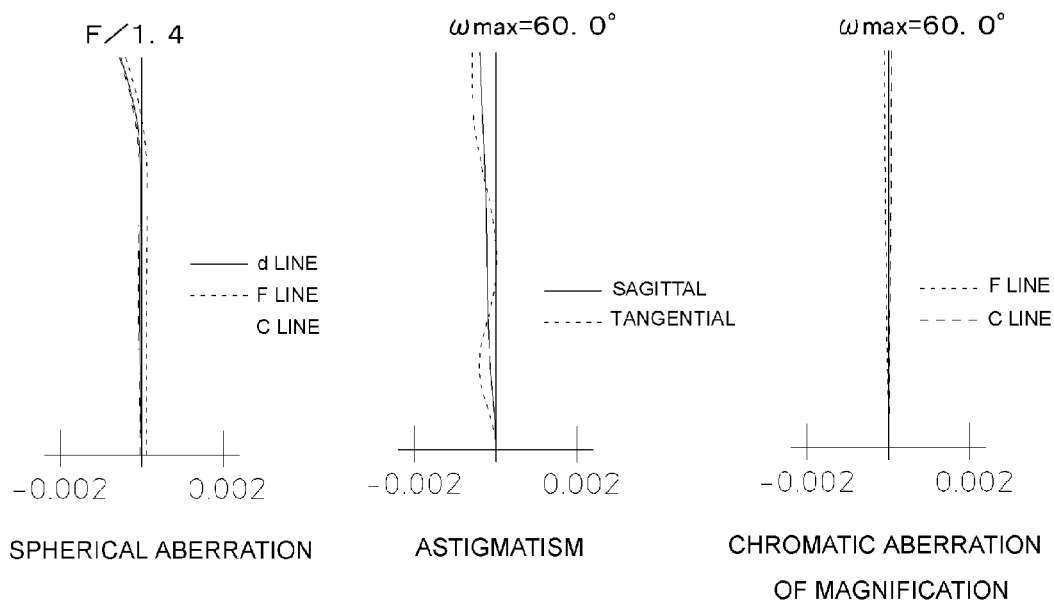
FIG. 7 is an aberration diagram of the image pickup optical system according to the first embodiment.

FIG. 7 shows spherical aberration, astigmatism, and chromatic aberration of magnification when the object 12 is focused on the image pickup surface through the transparent cover 23, and the cover glass 21 disposed in front of the image pickup device, in the image pickup optical system 20. As to the spherical aberration, d line having a wavelength of 587.6 nm is shown by a solid line, F line having a wavelength of 486.13 nm is shown by a first broken line, and C line having a wavelength of 656.27 nm is shown by a second broken line which is less minute than the first broken line. Further, astigmatism in the sagittal direction is shown by a solid line, and astigmatism in the tangential direction is shown by a first broken line. Furthermore, as to the chromatic aberration of magnification, F line is shown by the first broken line, and C line is shown by the second broken line which is less minute than the first broken line. Note that, also in Embodiments 2 to 15 which will be described later, it is common that the object 12 is focused on the image pickup surface through the transparent cover 23 and the cover glass 21, and that the spherical aberration, astigmatism, and chromatic aberration of magnification at the time of the focusing are described in the similar manner as that in Embodiment 1.

In the image pickup optical system 20 in Embodiment 1, ΔZr is −0.001 and ΔZp is 0.020. Accordingly, in the image pickup optical system 20 in which the maximum angle of view 2ωmax is 120°, ΔZr/ΔZp is within the range of not only the mathematical expression 2 but also the mathematical expression 1, and therefore the curvature of field is sufficiently corrected, and the whole object 12 including the central portion and the peripheral portion thereof is within the depth of field of the image pickup optical system 20. Thereby, a brilliant image in which both the central portion of the image and the peripheral portion thereof are in focus is obtained, and even if a lesion exists in the peripheral portion of the image, the lesion can be found with absolute accuracy.

Figure 8:
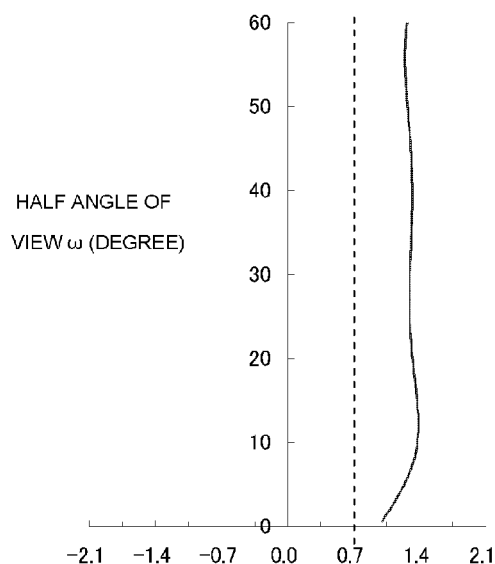
FIG. 8 is a graph showing distortion of the image pickup optical system according to the first embodiment.

As shown in FIG. 8, (Y(ω+Δω)−Y(ω))/Y(Δω) is more than 0.7 in the entire range of the half angle of view ω. Therefore, the image pickup optical system 20 satisfies the condition of the mathematical expression 3, and can suppress generation of distortion in the peripheral portion of the image. Accordingly, even if a lesion exists in the peripheral portion of the image, the lesion is not so distorted as to be overlooked, and therefore the lesion can be found with absolute accuracy.

[Embodiment 2]

Figure 9:
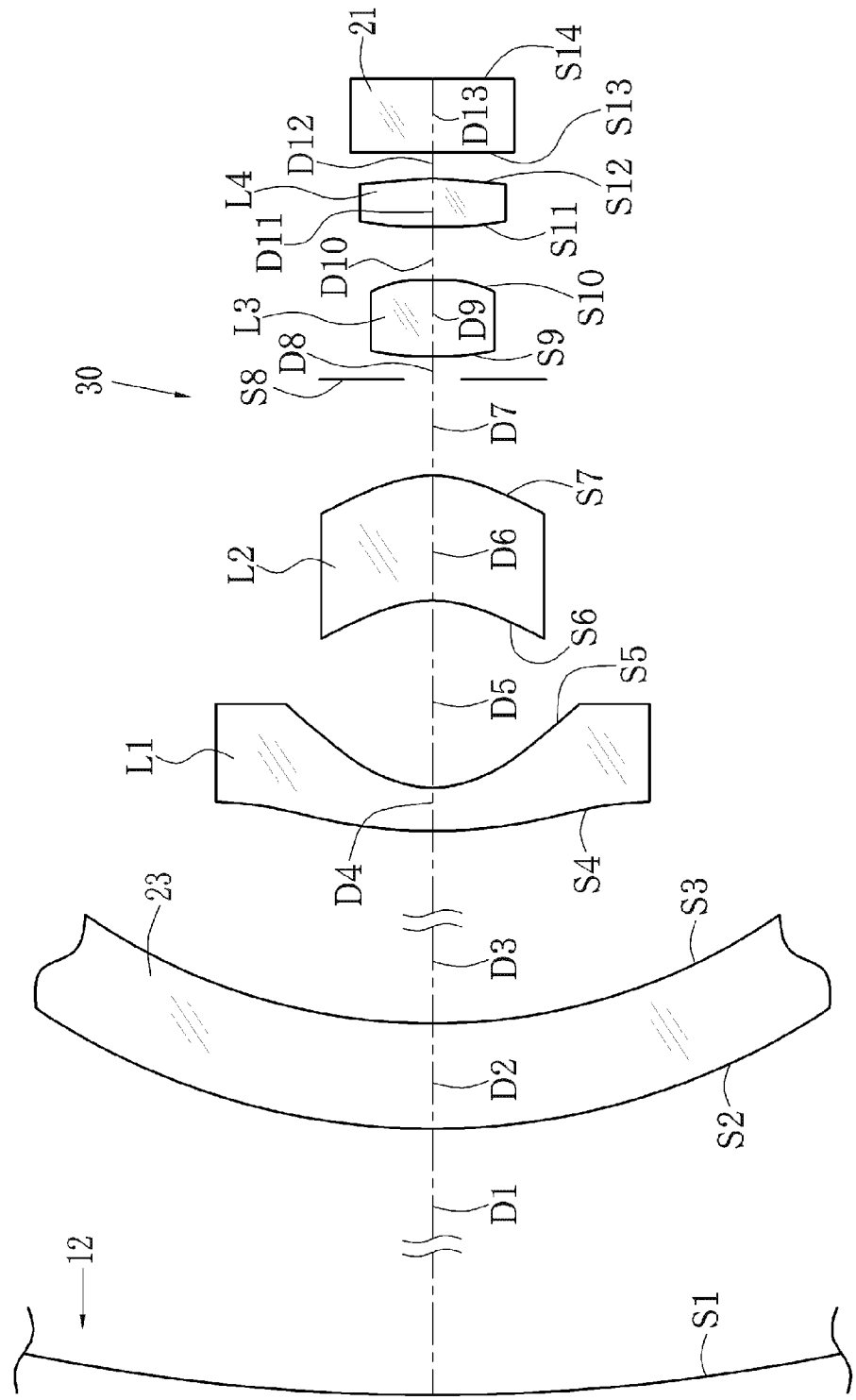
FIG. 9 is a lens configuration diagram of an image pickup optical system according to a second embodiment of the present invention.

As shown in FIG. 9, an image pickup optical system 30 of Embodiment 2 includes four lenses, namely, the first to fourth lenses L1 to L4, and an aperture stop S8. In the capsule 13, the first lens L1, the second lens L2, the aperture stop S8, the third lens L3, and the fourth lens L4 are disposed in this order from the side of the object 12 in the shape of concave hemisphere surface. The image pickup optical system 30 is designed based on lens data shown in the following Table 3.

TABLE 3 f = 1.0    Fno = 2.0    2ωmax = 130°

| SURFACE | RADIUS OF CURVATURE | SURFACE SEPARATION | $N_d$ | $v_d$ |
|---------|---------------------|--------------------|-------|-------|
| OBJ | 39.5606 | 25.7782 | | |
| 2   | 13.7824 | 2.0418  | 1.57500 | 32.2 |
| 3   | 11.7406 | 12.1829 | | |
| 4*  | 5.0795  | 0.7657  | 1.59988 | 61.1 |
| 5*  | 1.6044  | 3.4900  | | |
| 6*  | −3.3222 | 2.4804  | 1.62959 | 35.4 |
| 7*  | −2.7823 | 1.8455  | | |
| APERTURE STOP | ∞ | 0.3889 | | |
| 9*  | 5.1694  | 1.4993  | 1.49231 | 65.3 |
| 10* | −4.1621 | 0.9778  | | |
| 11* | 5.9761  | 0.9368  | 1.62896 | 60.0 |
| 12* | −3.3789 | 0.4856  | | |
| 13  | ∞       | 1.3910  | 1.55920 | 53.9 |
| 14  | ∞       | 0.0000  | | |
| IMG | ∞       |         | | |

As shown by "*" in the column of the surface number in Table 3, the both surfaces S4 and S5 of the first lens, the both surfaces S6 and S7 of the second lens, the both surfaces S9 and S10 of the third lens, and the both surfaces S11 and S12 of the fourth lens are aspherical. The conic constant K and the aspherical constant Ai of the surfaces S4, S5, S6, S7, S9, S10, S11, and S12 are shown in Table 4.

TABLE 4

| SURFACE | K | $A_3$ | $A_4$ | $A_5$ |
|---------|---|-------|-------|-------|
| 4  | −1.0000 | −2.0501E−02 | 6.4026E−04  | 5.6140E−05  |
| 5  | −1.0000 | −4.3069E−02 | 5.6383E−04  | 1.5408E−05  |
| 6  | −1.0000 | 1.6453E−03  | −1.4624E−03 | −8.5712E−07 |
| 7  | −1.0000 | 1.3316E−02  | −1.4576E−03 | 3.8609E−06  |
| 9  | −1.0000 | 3.1361E−03  | −1.8619E−02 | 2.5537E−02  |
| 10 | −1.0000 | −5.7329E−02 | 1.6786E−02  | 2.4299E−02  |
| 11 | −1.0000 | −1.3975E−02 | −1.9713E−03 | −2.5743E−04 |
| 12 | −1.0000 | 6.4008E−02  | 3.8239E−03  | 1.0578E−03  |

TABLE 4-continued

| SURFACE | $A_6$ | $A_7$ | $A_8$ | $A_9$ |
|---|---|---|---|---|
| 4 | 1.7422E-06 | 6.7475E-08 | 3.6954E-10 | -5.4165E-10 |
| 5 | 2.9559E-06 | 7.2531E-07 | 1.7534E-07 | 4.3091E-08 |
| 6 | 4.7656E-08 | 2.7950E-07 | 2.6414E-07 | 1.4935E-07 |
| 7 | 7.3642E-06 | 1.7963E-06 | 4.2105E-07 | 1.2531E-07 |
| 9 | -2.7382E-03 | -5.2721E-04 | -1.5154E-02 | -1.6241E-02 |
| 10 | 5.4677E-02 | -2.1719E-01 | 1.7186E-01 | -3.4155E-03 |
| 11 | 3.2253E-04 | 3.1503E-04 | 1.7658E-04 | 1.2592E-04 |
| 12 | 2.4858E-04 | 2.4932E-05 | -2.8668E-06 | 2.2412E-05 |

| SURFACE | $A_{10}$ | $A_{11}$ | $A_{12}$ | $A_{13}$ |
|---|---|---|---|---|
| 4 | -1.7096E-10 | -4.4965E-11 | -8.2587E-12 | -1.3975E-12 |
| 5 | 1.1113E-08 | 2.9617E-09 | 7.9249E-10 | 2.0786E-10 |
| 6 | 7.5671E-08 | 3.5467E-08 | 1.5719E-08 | 6.8059E-09 |
| 7 | 4.1332E-08 | 1.5972E-08 | 6.5313E-09 | 2.7188E-09 |
| 9 | 9.3617E-03 | 7.1994E-03 | -7.4710E-04 | -3.2288E-06 |
| 10 | 1.3576E-02 | -6.7705E-02 | 2.8537E-02 | -1.2542E-04 |
| 11 | 1.0712E-04 | -4.1601E-05 | -2.0497E-04 | -2.4984E-05 |
| 12 | 4.3447E-05 | 2.0654E-05 | 1.5589E-05 | -2.5035E-07 |

| SURFACE | $A_{14}$ | $A_{15}$ | $A_{16}$ | $A_{17}$ |
|---|---|---|---|---|
| 4 | -2.3366E-13 | -1.6504E-14 | 1.6164E-15 | 1.2950E-15 |
| 5 | 5.2447E-11 | 1.2383E-11 | 2.6242E-12 | 4.3402E-13 |
| 6 | 2.8850E-09 | 1.2116E-09 | 5.0839E-10 | 2.1381E-10 |
| 7 | 1.1161E-09 | 4.5007E-10 | 1.7812E-10 | 7.0028E-11 |
| 9 | -3.9856E-19 | 6.7351E-21 | 0.0000E+00 | 1.9589E-19 |
| 10 | -4.1614E-07 | -8.9654E-20 | 1.6664E-21 | 0.0000E+00 |
| 11 | 3.2249E-05 | 7.0371E-09 | 2.8102E-21 | 0.0000E+00 |
| 12 | -2.2463E-05 | 6.7575E-08 | 1.1437E-20 | -8.3818E-28 |

| SURFACE | $A_{18}$ | $A_{19}$ | $A_{20}$ |
|---|---|---|---|
| 4 | 5.8032E-16 | 1.8130E-16 | 5.0782E-17 |
| 5 | 1.7618E-14 | -2.8848E-14 | -9.3040E-15 |
| 6 | 6.4088E-11 | 2.3582E-11 | 1.8866E-30 |
| 7 | 2.7138E-11 | 1.0078E-11 | 1.4585E-13 |
| 9 | 7.6750E-21 | 3.0071E-22 | 1.1782E-23 |
| 10 | 0.0000E+00 | 3.0071E-22 | 1.1782E-23 |
| 11 | 0.0000E+00 | 0.0000E+00 | 0.0000E+00 |
| 12 | 0.0000E+00 | 0.0000E+00 | 0.0000E+00 |

Figure 10:
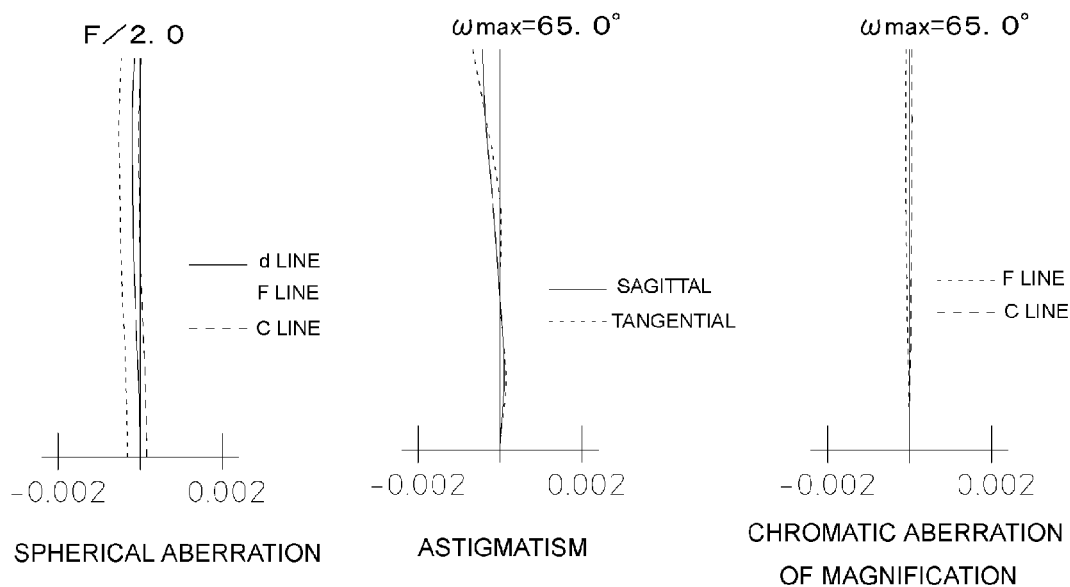
FIG. 10 is an aberration diagram of the image pickup optical system according to the second embodiment.

FIG. 10 shows spherical aberration, astigmatism, and chromatic aberration of magnification in the image pickup optical system. In the image pickup optical system 30 of Embodiment 2, the maximum angle of view is 130°, ΔZr is -0.005, and ΔZp is 0.028. Accordingly, ΔZr/Δ Zp is -0.167, which is within the range of not only the mathematical expression 2 but also the mathematical expression 1. Therefore, the curvature of field is sufficiently corrected, and the whole object 12 including the central portion and the peripheral portion thereof is within the depth of field of the image pickup optical system 30. Thereby, a brilliant image in which both the central portion of the image and the peripheral portion thereof are in focus is obtained, and even if a lesion exists in the peripheral portion of the image, the lesion can be found with absolute accuracy.

Figure 11:
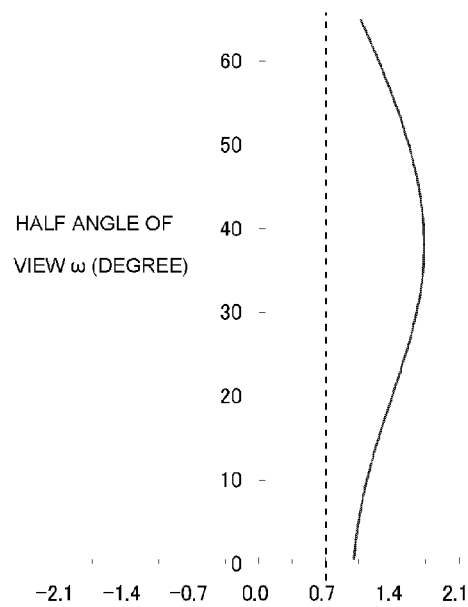
FIG. 11 is a graph showing distortion of the image pickup optical system according to the second embodiment.

As shown in FIG. 11, (Y(ω+Δω)-Y(ω))/Y(Δω) is more than 0.7 in the entire range of the half angle of view ω. Therefore, the image pickup optical system 30 satisfies the condition of the mathematical expression 3, and can suppress the distortion in the peripheral portion of the image. Accordingly, even if a lesion exists in the peripheral portion of the image, the lesion is not so distorted as to be overlooked, and the lesion can be found with absolute accuracy.

[Embodiment 3]

Figure 12:
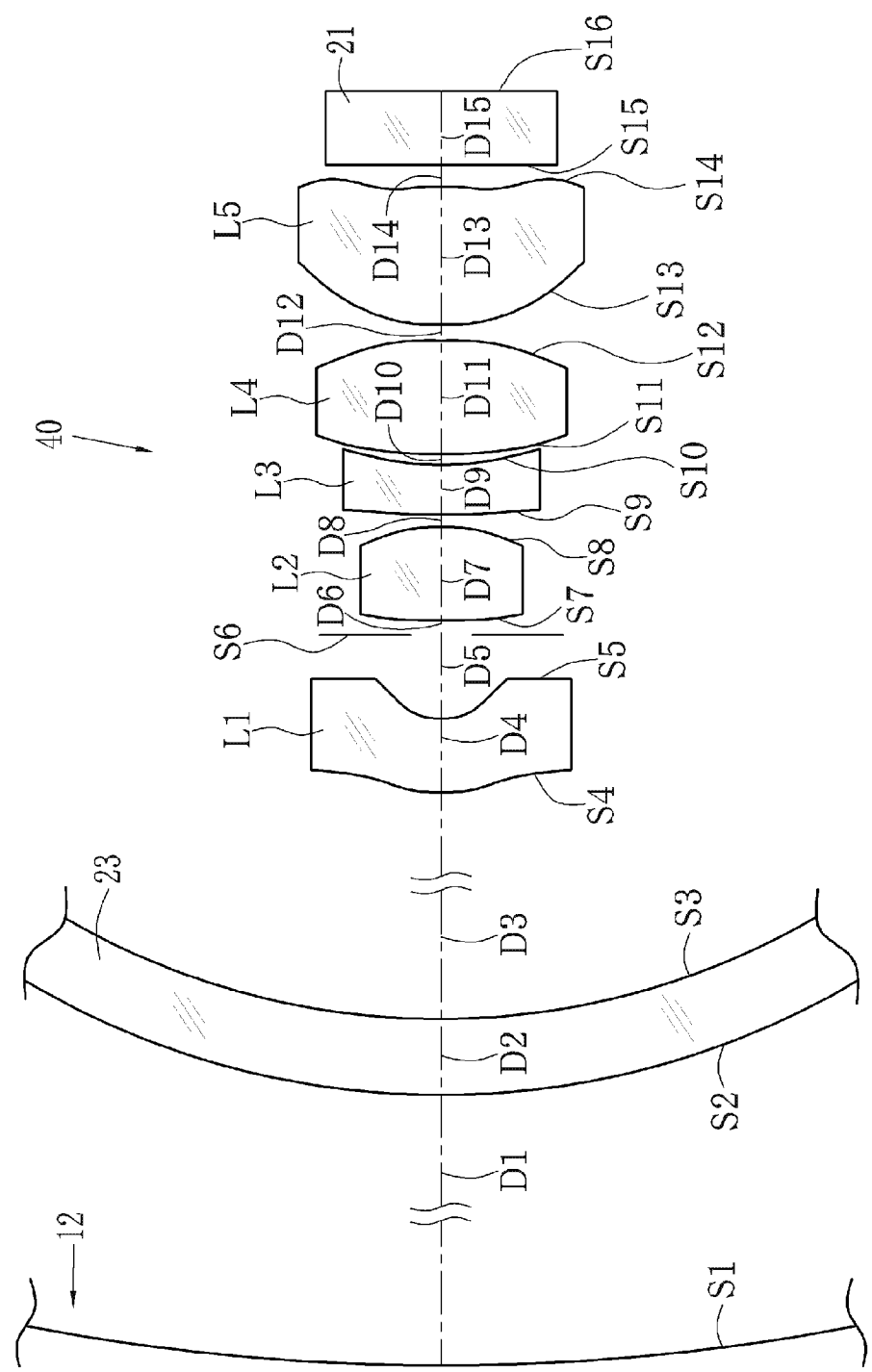
FIG. 12 is a lens configuration diagram of an image pickup optical system according to a third embodiment of the present invention.

As shown in FIG. 12, an image pickup optical system 40 of Embodiment 3 includes five lenses, namely, the first to fifth lenses L1 to L5, and the aperture stop S6. In the capsule 13, the first lens L1, the aperture stop S6, the second lens L2, the third lens L3, the fourth lens L4, and the fifth lens L5 are disposed in this order from the side of the object 12 in the shape of concave hemisphere surface. The image pickup optical system 40 is designed based on lens data shown in the following Table 5.

TABLE 5

| f = 1.0 Fno = 1.4 2ωmax = 130° | | | | |
|---|---|---|---|---|
| SURFACE | RADIUS OF CURVATURE | SURFACE SEPARATION | $N_d$ | $v_d$ |
| OBJ | 29.0646 | 18.3763 | | |
| 2 | 10.6883 | 0.9376 | 1.58600 | 55.0 |
| 3 | 9.7507 | 9.0608 | | |
| 4* | 7.6427 | 0.9376 | 1.53039 | 55.2 |
| 5* | 0.7890 | 1.0730 | | |
| APERTURE STOP | ∞ | 0.1921 | | |
| 7 | 5.8843 | 1.2083 | 1.72916 | 54.7 |
| 8 | -2.3685 | 0.1875 | | |
| 9 | 14.4343 | 0.5625 | 1.92286 | 18.9 |
| 10 | 3.1531 | 0.1875 | | |
| 11 | 5.3173 | 1.4824 | 1.72916 | 54.7 |
| 12 | -3.7807 | 0.1875 | | |
| 13* | 2.9814 | 1.7960 | 1.53039 | 55.2 |
| 14* | -1.6144 | 0.2585 | | |
| 15 | ∞ | 0.9376 | 1.55920 | 53.9 |
| 16 | ∞ | 0.0000 | | |
| IMG | ∞ | | | |

As shown by "*" in the column of the surface number in Table 5, the both surfaces S4 and S5 of the first lens L1 and the both surfaces S13 and S14 of the fifth lens L5 are aspherical. The conic constant K and the aspherical constant Ai of the surfaces S4, S5, S13, and S14 are shown in Table 6.

of the object 12. The third lens L3 and the fourth lens L4 constitute a laminated lens. As in the case of the above Embodiments, FIG. 7 shows lens data, and FIG. 8 shows data of the aspherical surfaces each of which is assigned with "*" in the column of the surface number.

TABLE 6

| SURFACE | K | $A_3$ | $A_4$ | $A_5$ |
|---|---|---|---|---|
| 4 | −1.0000 | 2.8635E−01 | −1.3493E−01 | −5.5162E−02 |
| 5 | −1.0000 | 1.3048E−01 | 1.2018E+00 | −1.9042E+00 |
| 13 | −1.0000 | 2.6955E−02 | 3.1178E−02 | −2.7344E−02 |
| 14 | −1.0000 | 3.4708E−01 | 5.3036E−02 | −5.8731E−02 |

| SURFACE | $A_6$ | $A_7$ | $A_8$ | $A_9$ |
|---|---|---|---|---|
| 4 | −4.7267E−03 | 7.8112E−03 | 5.4810E−03 | 2.1856E−03 |
| 5 | −3.8642E+00 | 7.2601E+00 | 6.0466E+00 | −2.1930E+01 |
| 13 | 5.9775E−03 | 3.4712E−03 | −3.7983E−04 | −7.2378E−04 |
| 14 | −3.0082E−02 | −5.3533E−03 | 2.1681E−03 | 2.3301E−03 |

| SURFACE | $A_{10}$ | $A_{11}$ | $A_{12}$ | $A_{13}$ |
|---|---|---|---|---|
| 4 | 4.3373E−04 | −1.4517E−04 | −2.2093E−04 | −3.0188E−04 |
| 5 | 1.8094E+01 | −1.9584E+00 | −5.7833E+00 | 3.2192E+00 |
| 13 | −2.2372E−04 | −1.9247E−05 | 4.7273E−05 | 2.9245E−05 |
| 14 | 1.2452E−03 | 1.0549E−04 | −5.5831E−05 | −4.4047E−05 |

| SURFACE | $A_{14}$ | $A_{15}$ | $A_{16}$ | $A_{17}$ |
|---|---|---|---|---|
| 4 | −2.2543E−04 | 2.2081E−04 | −2.4064E−05 | 3.2946E−06 |
| 5 | −4.4566E−01 | −1.6772E−03 | 7.3712E−16 | 3.9447E−17 |
| 13 | 1.0991E−05 | −2.1717E−06 | −2.8377E−06 | −1.3897E−06 |
| 14 | −8.4327E−05 | 1.5416E−06 | 8.9907E−06 | 2.3941E−06 |

| SURFACE | $A_{18}$ | $A_{19}$ | $A_{20}$ |
|---|---|---|---|
| 4 | −2.8705E−06 | 2.2033E−08 | 5.1511E−10 |
| 5 | 9.1388E−11 | 4.0410E−12 | 2.1548E−13 |
| 13 | 6.6916E−07 | −1.6113E−08 | −9.9746E−10 |
| 14 | −5.3968E−07 | −1.1076E−08 | −1.1041E−08 |

Figure 13:
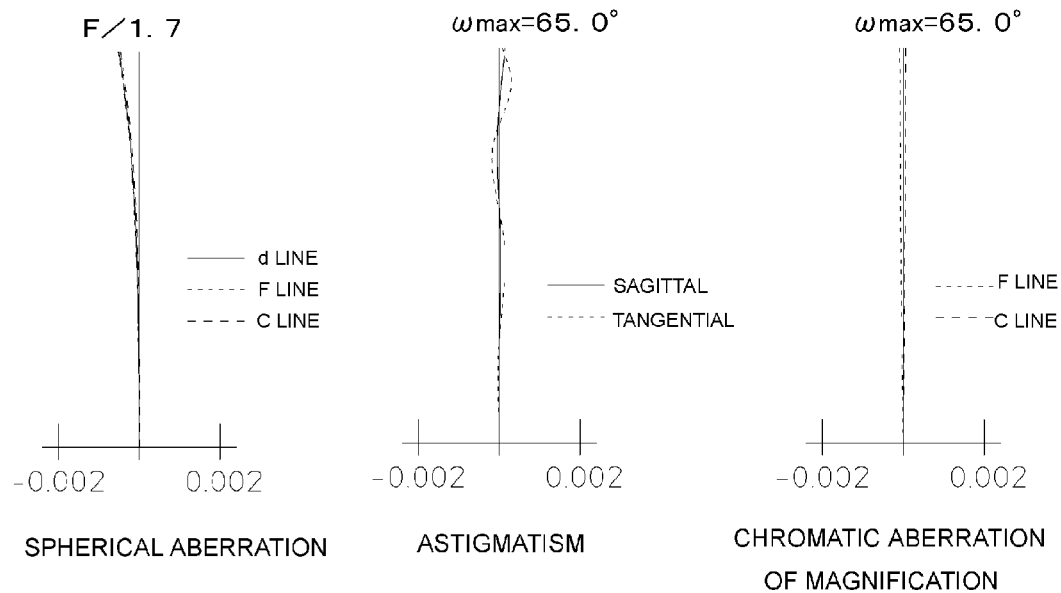
FIG. 13 is an aberration diagram of the image pickup optical system according to the third embodiment.
Figure 14:
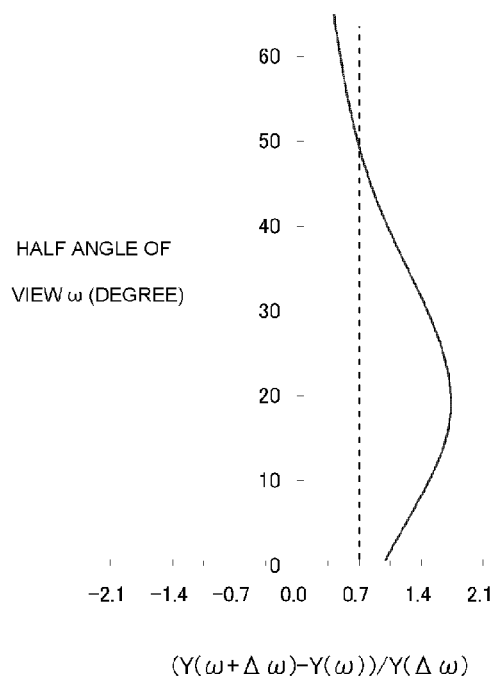
FIG. 14 is a graph showing distortion of the image pickup optical system according to the third embodiment.

FIG. 13 shows spherical aberration, astigmatism, and chromatic aberration of magnification in the image pickup optical system 40 as in the case of the above Embodiments. ΔZr is 0.003, and Δ Zp is 0.036. Accordingly, in the image pickup optical system 40 in which the maximum angle of view 2ωmax is 130°, ΔZr/ΔZp is 0.081, and therefore the image pickup optical system 40 satisfies not only the mathematical expression 2 but also the mathematical expression 1. Therefore, the curvature of field is sufficiently corrected, and the whole object 12 including its central portion and peripheral portion is within the depth of field of the image pickup optical system 40. Further, as shown in FIG. 14, (Y(ω+Δω)−Y(ω))/Y(Δω) is more than 0.7 in almost all the range of the half angle of view w. Therefore, it is possible to suppress the distortion in the image. Thereby, a brilliant image in which both the central portion of the image and the peripheral portion thereof are in focus is obtained, and even if a lesion exists in the peripheral portion of the image, the lesion can be found with absolute accuracy.

[Embodiment 4]

Figure 15:
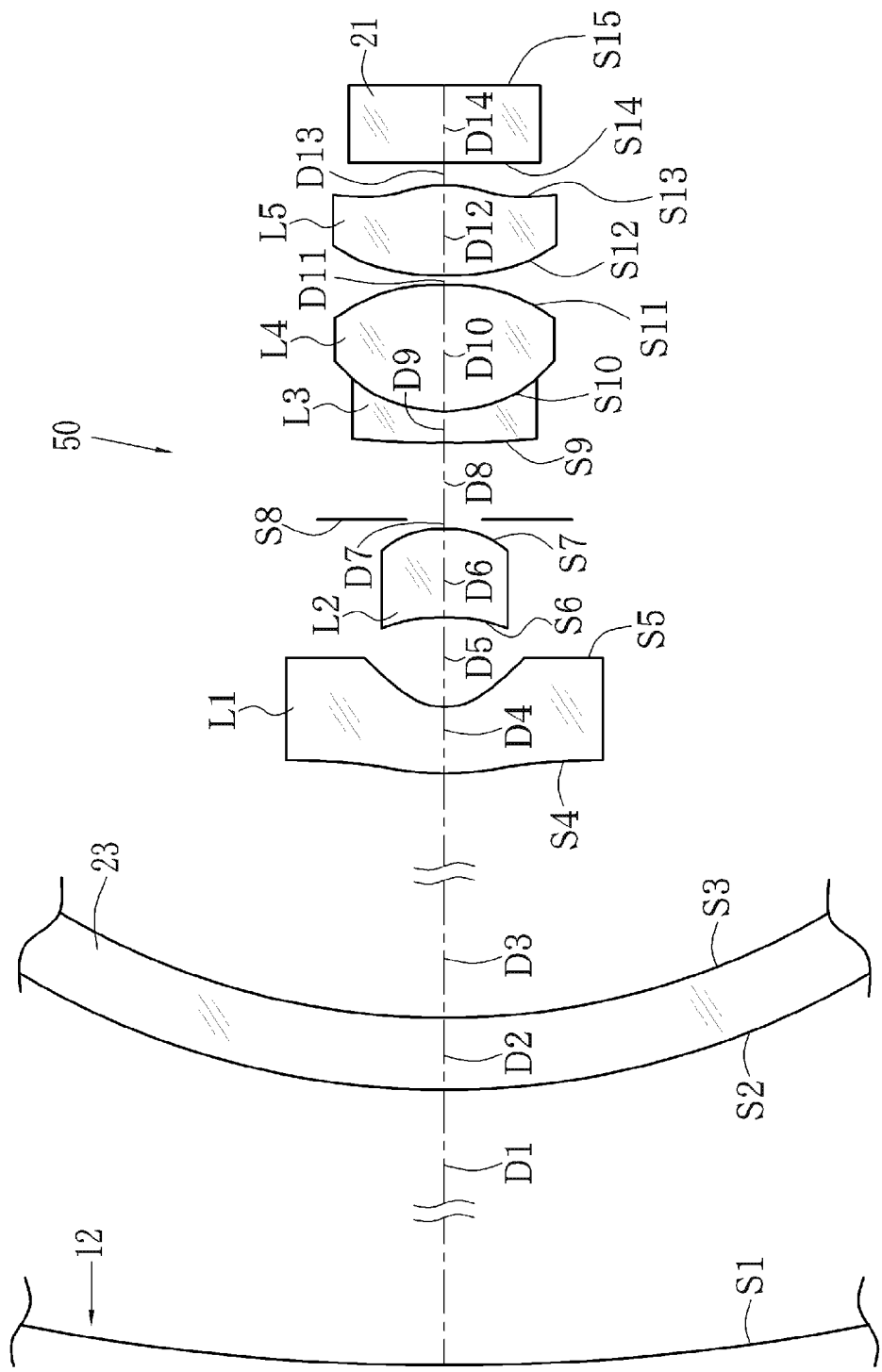
FIG. 15 is a lens configuration diagram of an image pickup optical system according to a fourth embodiment of the present invention.

As shown in FIG. 15, an image pickup optical system 50 of Embodiment 4 includes the first lens L1, the second lens L2, the aperture stop S8, the third lens L3, the fourth lens L4, and the fifth lens L5, which are disposed in this order from the side

TABLE 7

| | f = 1.0 Fno = 1.4 2ωmax = 125° | | | |
|---|---|---|---|---|
| SURFACE | RADIUS OF CURVATURE | SURFACE SEPARATION | $N_d$ | $v_d$ |
| OBJ | 52.7239 | 33.3351 | | |
| 2 | 19.3888 | 1.7008 | 1.58600 | 55.0 |
| 3 | 17.6880 | 17.0074 | | |
| 4* | 5.2946 | 1.5139 | 1.53159 | 55.4 |
| 5* | 0.8891 | 2.0503 | | |
| 6* | −5.9555 | 2.0397 | 1.63178 | 23.2 |
| 7* | −2.6434 | 0.1701 | | |
| APERTURE STOP | ∞ | 1.7936 | | |
| 9 | 36.1366 | 0.7325 | 1.84666 | 23.8 |
| 10 | 3.4022 | 2.9713 | 1.72916 | 54.7 |
| 11 | −4.4544 | 0.1703 | | |
| 12* | 6.2668 | 2.0450 | 1.54378 | 55.7 |
| 13* | −2.5715 | 0.6555 | | |
| 14 | ∞ | 1.7008 | 1.55920 | 53.9 |
| 15 | ∞ | 0.0000 | | |
| IMG | ∞ | | | |

TABLE 8

| SURFACE | K | $A_3$ | $A_4$ | $A_5$ |
|---|---|---|---|---|
| 4 | −1.0000 | −1.9923E−02 | −4.6538E−03 | 6.6680E−04 |
| 5 | −1.0000 | −4.5601E−01 | 4.1102E−01 | −7.8056E−02 |
| 6 | −1.0000 | 1.8433E−02 | −5.1519E−02 | 3.8602E−03 |
| 7 | −1.0000 | −1.4578E−02 | 3.2847E−02 | −2.7181E−02 |
| 12 | −1.0000 | −1.2298E−02 | 1.5591E−02 | −3.7547E−03 |
| 13 | −1.0000 | 5.8994E−02 | 5.4660E−03 | 3.1128E−04 |

| SURFACE | $A_6$ | $A_7$ | $A_8$ | $A_9$ |
|---|---|---|---|---|
| 4 | 1.7902E−04 | 2.1145E−05 | −4.1897E−07 | −9.0971E−07 |
| 5 | −7.8055E−02 | −6.9739E−03 | 1.9975E−02 | 1.0245E−02 |
| 6 | 1.0699E−02 | 4.0125E−03 | −2.9932E−03 | −5.0475E−03 |
| 7 | −2.6759E−03 | 3.1390E−03 | 2.2492E−03 | 1.2013E−04 |
| 12 | −4.0691E−05 | 1.2236E−04 | 1.3086E−05 | −1.5159E−06 |
| 13 | −2.8313E−04 | −8.3211E−05 | −1.3140E−05 | −4.5317E−06 |

| SURFACE | $A_{10}$ | $A_{11}$ | $A_{12}$ | $A_{13}$ |
|---|---|---|---|---|
| 4 | −2.6137E−07 | −4.7619E−08 | −3.7807E−09 | 1.2921E−09 |
| 5 | −2.2268E−03 | −4.5038E−03 | 1.2009E−03 | 2.2592E−04 |
| 6 | 1.1318E−03 | 1.1407E−03 | −9.8276E−05 | −1.2913E−04 |
| 7 | 1.0143E−04 | −2.6607E−04 | −3.5757E−04 | 1.9831E−04 |
| 12 | −9.8995E−07 | −3.2232E−07 | −2.8262E−08 | 7.9296E−10 |
| 13 | 9.4782E−07 | 1.3032E−07 | 2.5212E−08 | 1.3574E−08 |

| SURFACE | $A_{14}$ | $A_{15}$ | $A_{16}$ | $A_{17}$ |
|---|---|---|---|---|
| 4 | 6.5989E−10 | 1.6005E−10 | 7.2856E−12 | −9.4053E−12 |
| 5 | −6.8325E−05 | −4.2745E−07 | 1.1389E−11 | 2.8595E−21 |
| 6 | 2.0647E−05 | 1.0009E−06 | −8.0772E−16 | 2.0205E−11 |
| 7 | −8.7066E−06 | −3.7052E−07 | −8.2954E−08 | −4.9366E−10 |
| 12 | 6.6772E−09 | 2.3977E−09 | −1.0292E−09 | 1.2059E−10 |
| 13 | −2.3294E−08 | 8.1870E−09 | −2.7203E−09 | 4.2447E−10 |

| SURFACE | $A_{18}$ | $A_{19}$ | $A_{20}$ |
|---|---|---|---|
| 4 | −1.4375E−12 | 2.9615E−13 | 6.5820E−16 |
| 5 | −2.6919E−19 | −1.0516E−18 | −3.0915E−20 |
| 6 | 9.9243E−20 | 1.8830E−21 | 5.5361E−23 |
| 7 | 1.4436E−12 | −2.0632E−24 | 8.5817E−23 |
| 12 | −3.6749E−12 | −5.1734E−13 | −1.1508E−14 |
| 13 | 8.4678E−12 | −1.3572E−13 | −1.3446E−13 |

Figure 16:
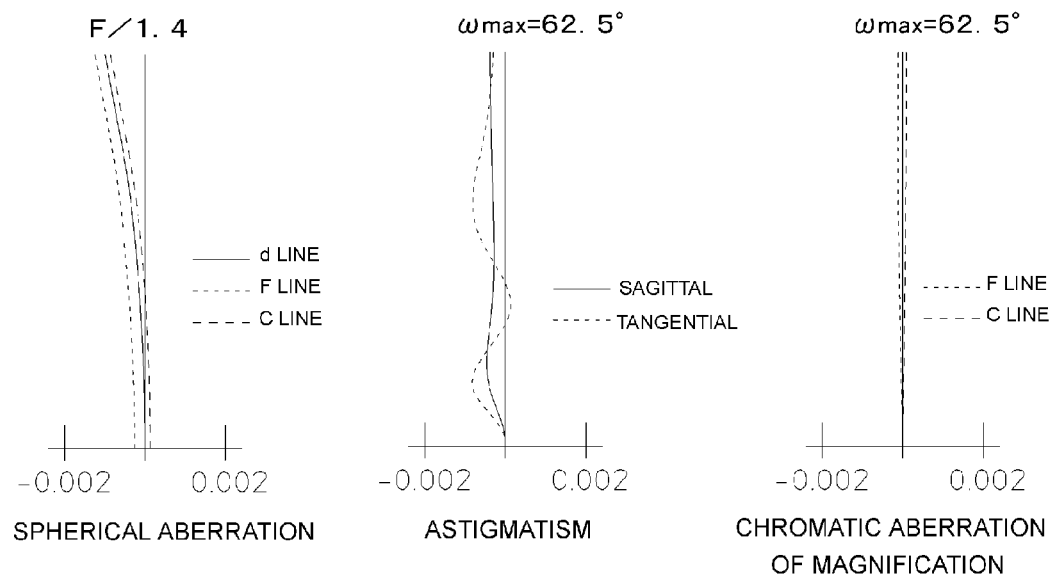
FIG. 16 is an aberration diagram of the image pickup optical system according to the fourth embodiment.
Figure 17:
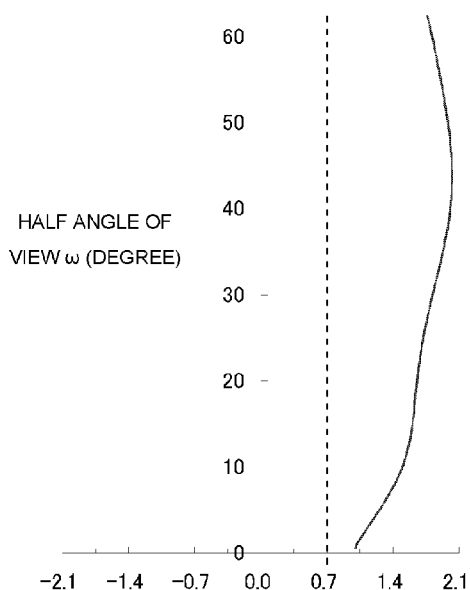
FIG. 17 is a graph showing distortion of the image pickup optical system according to the fourth embodiment.

FIG. 16 shows spherical aberration, astigmatism, and chromatic aberration of magnification in the image pickup optical system 50. The maximum angle of the image pickup optical system 50 is 125°. ΔZr is −0.005, ΔZp is 0.018, and ΔZr/ΔZp is −0.279, which is within the range of not only the mathematical expression but also the mathematical expression 1. Therefore, the curvature of field is sufficiently corrected, and the whole object 12 including its central portion and peripheral portion is within the depth of field of the image pickup optical system 50. Thereby, a brilliant image in which both the central portion of the image and the peripheral portion thereof are in focus is obtained, and even if a lesion exists in the peripheral portion of the image, the lesion can be found with absolute accuracy. Further, as shown in FIG. 17, (Y(w+Δω)−Y(ω))/Y(Δω) is more than 0.7. Therefore, the image pickup optical system 50 satisfies the condition of the mathematical expression 3, and can successively suppress the distortion in the peripheral portion of the image.

[Embodiment 5]

Figure 18:
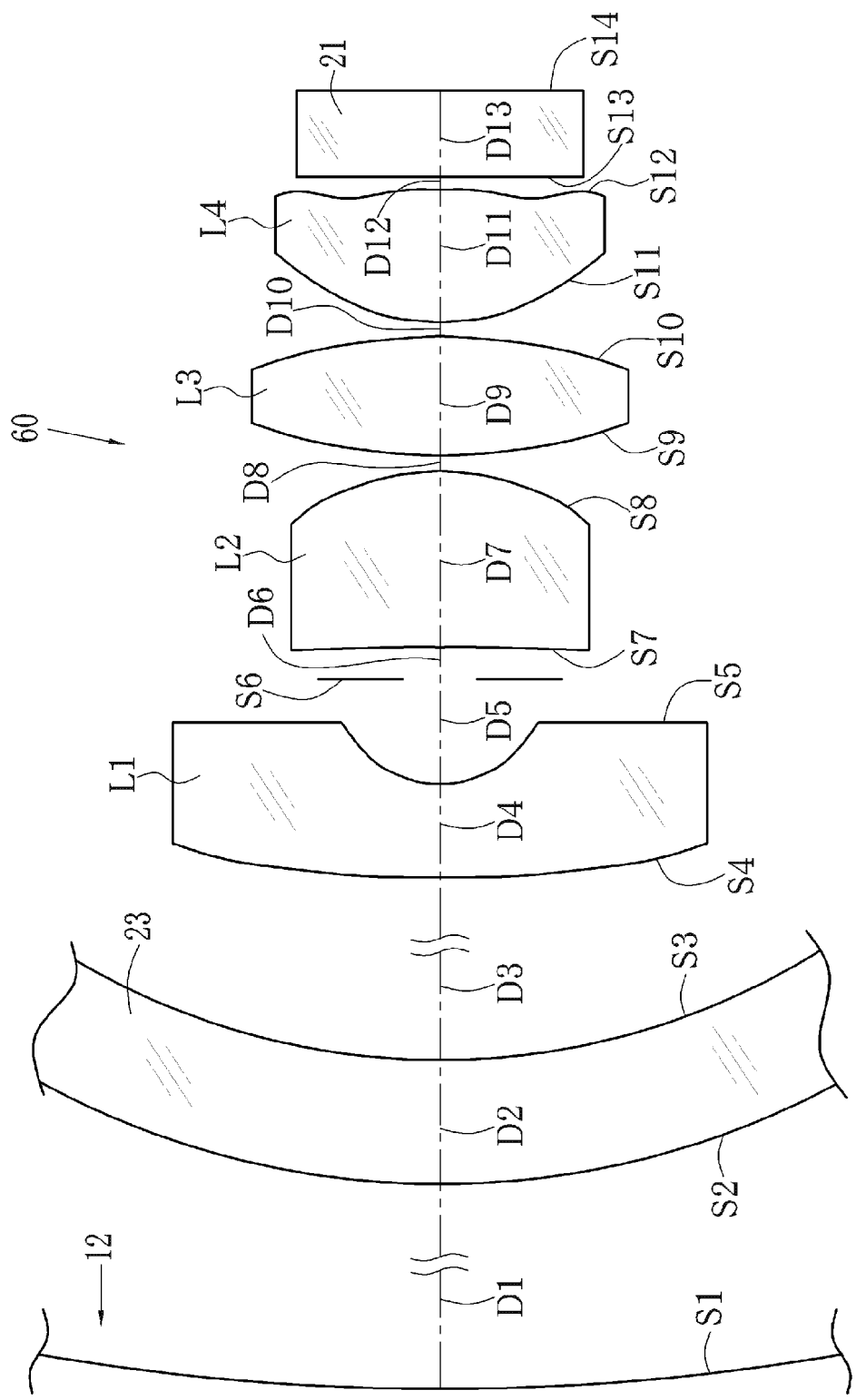
FIG. 18 is a lens configuration diagram of an image pickup optical system according to a fifth embodiment of the present invention.
Figure 19:
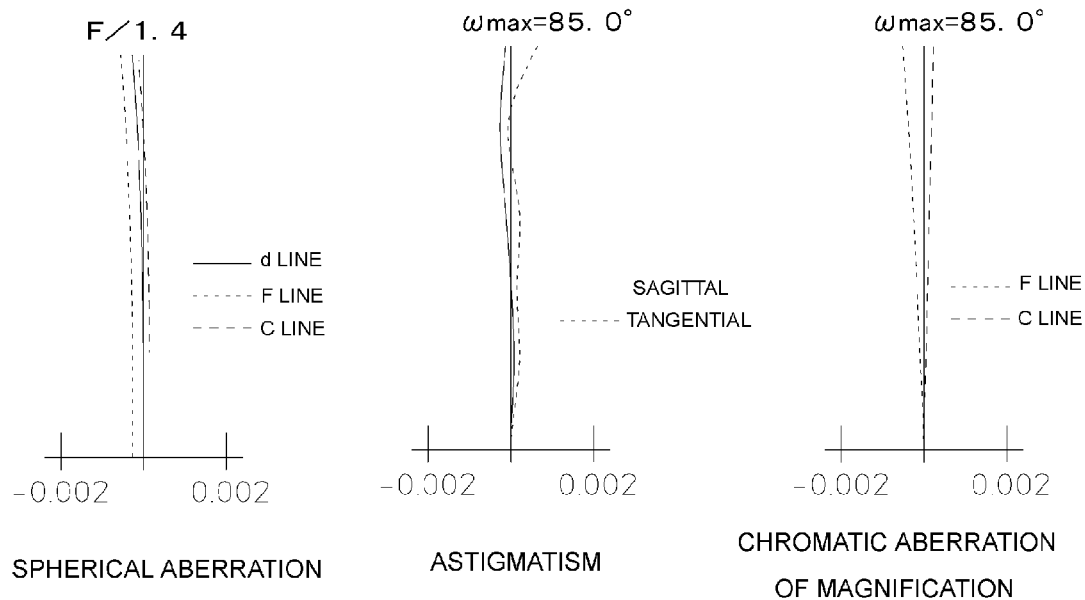
FIG. 19 is an aberration diagram of the image pickup optical system according to the fifth embodiment.

The configuration of an image pickup optical system 60 of Embodiment 5 is shown in FIG. 18. As in the case of the above Embodiments, Table 9 shows lens data, Table 10 shows data of aspherical surfaces respectively assigned with the surface numbers S4, S5, S11, and S12. FIG. 19 shows the spherical aberration, astigmatism, and chromatic aberration of magnification.

TABLE 9 f = 1.0   Fno = 1.4   2ωmax = 170°

| SURFACE | RADIUS OF CURVATURE | SURFACE SEPARATION | $N_d$ | $v_d$ |
|---|---|---|---|---|
| OBJ | 29.0057 | 16.9570 | | |
| 2 | 10.2579 | 1.4971 | 1.57500 | 32.2 |
| 3 | 8.7517 | 5.8627 | | |
| 4* | 21.0846 | 1.1291 | 1.53039 | 55.2 |
| 5* | 1.2635 | 1.2642 | | |
| APERTURE STOP | ∞ | 0.3829 | | |
| 7 | −21.3026 | 2.1301 | 1.80400 | 46.6 |
| 8 | −3.0244 | 0.1873 | | |
| 9 | 7.5453 | 1.4255 | 1.80400 | 46.6 |
| 10 | −7.1995 | 0.1865 | | |
| 11* | 2.6921 | 1.5813 | 1.53039 | 55.2 |
| 12* | −4.0858 | 0.1806 | | |
| 13 | ∞ | 1.0199 | 1.55920 | 53.9 |
| 14 | ∞ | 0.0000 | | |
| IMG | ∞ | | | |

TABLE 10

| SURFACE | K | $A_3$ | $A_4$ | $A_5$ |
|---|---|---|---|---|
| 4 | −1.0000 | 1.1806E−03 | 6.0847E−04 | 1.1648E−04 |
| 5 | −1.0000 | 3.0189E−02 | 2.9023E−02 | −1.1704E−03 |
| 11 | −1.0000 | 6.2958E−03 | −6.0490E−03 | 3.8647E−03 |
| 12 | −1.0000 | 4.0413E−02 | 1.1306E−02 | 2.8963E−03 |

| SURFACE | $A_6$ | $A_7$ | $A_8$ | $A_9$ |
|---|---|---|---|---|
| 4 | 1.1526E−05 | −3.1849E−07 | −5.5674E−07 | −1.9003E−07 |
| 5 | −1.1450E−04 | 3.8652E−03 | 4.5996E−03 | 3.2054E−03 |
| 11 | 1.3835E−03 | 9.1107E−05 | −1.2677E−04 | −7.7351E−05 |
| 12 | 1.6035E−03 | 9.4610E−04 | 4.0676E−04 | 9.5714E−05 |

| SURFACE | $A_{10}$ | $A_{11}$ | $A_{12}$ | $A_{13}$ |
|---|---|---|---|---|
| 4 | −4.4059E−08 | −6.2540E−09 | 3.8526E−10 | 6.0256E−10 |
| 5 | 1.5331E−03 | 4.4516E−04 | −5.1892E−05 | −2.0610E−04 |
| 11 | −2.3361E−05 | −8.6265E−08 | 5.3226E−06 | 4.3320E−06 |
| 12 | −3.5343E−05 | −6.5696E−05 | −5.5364E−05 | −3.5172E−05 |

| SURFACE | $A_{14}$ | $A_{15}$ | $A_{16}$ | $A_{17}$ |
|---|---|---|---|---|
| 4 | 1.8528E−10 | 1.0491E−11 | −3.7667E−12 | −6.3129E−13 |
| 5 | −2.1831E−04 | −1.9444E−04 | −3.3983E−05 | −2.3424E−07 |
| 11 | 2.3286E−06 | 8.4037E−07 | 3.8252E−08 | −2.8889E−07 |
| 12 | −1.7641E−05 | −5.8258E−06 | 8.5904E−07 | 3.9596E−06 |

| SURFACE | $A_{18}$ | $A_{19}$ | $A_{20}$ |
|---|---|---|---|
| 4 | −1.3027E−13 | −2.5007E−15 | 3.8559E−15 |
| 5 | −1.2454E−07 | 0.0000E+00 | 3.9978E−20 |
| 11 | −3.6116E−07 | −1.7141E−08 | 0.0000E+00 |
| 12 | 1.5778E−07 | 0.0000E+00 | 0.0000E+00 |

Figure 20:
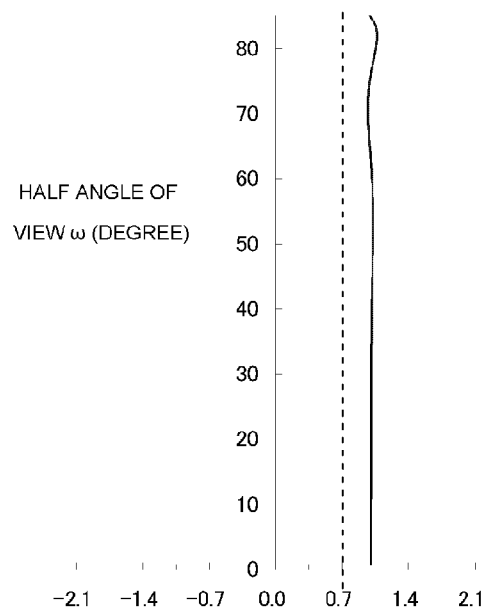
FIG. 20 is a graph showing distortion of the image pickup optical system according to the fifth embodiment.

The maximum angle of the image pickup optical system 60 of Embodiment 5 is 170°. ΔZr is −0.018, ΔZp is 0.202, and ΔZr/ΔZp is −0.088, which is within the range of not only the mathematical expression 2 but also the mathematical expression 1. Moreover, as shown in FIG. 20, (Y(ω+Δω)−Y(ω))/Y (Δω) is more than 0.7. Therefore, the image pickup optical system 60 also satisfies the condition of the mathematical expression 3, and the image of the object 12 including its central portion and peripheral portion is successively within the depth of field. Accordingly, the peripheral portion of the image is not distorted so much, and it is possible to successively performing the image forming.

[Embodiment 6]

Figure 21:
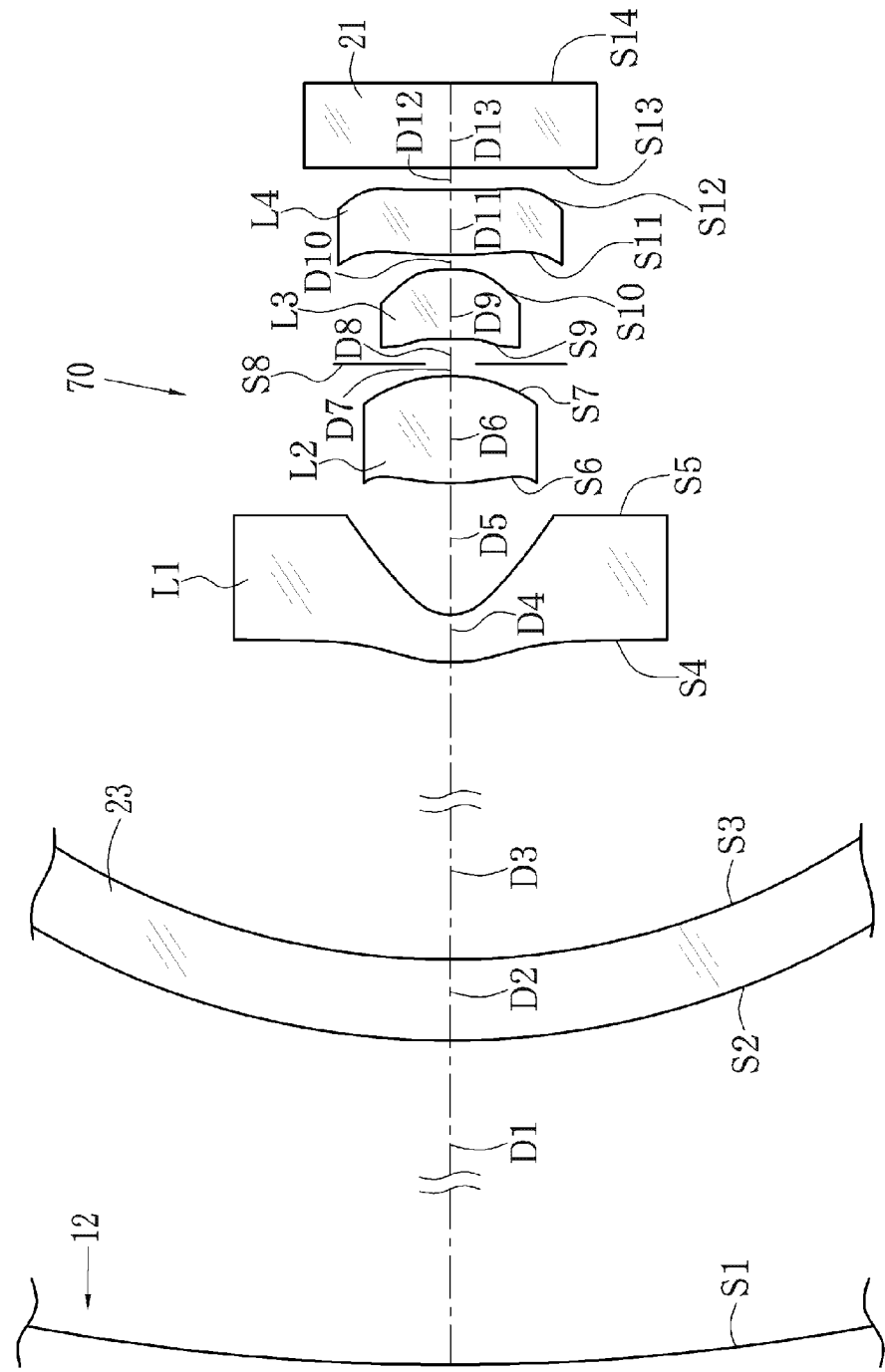
FIG. 21 is a lens configuration diagram of an image pickup optical system according to a sixth embodiment of the present invention.
Figure 22:
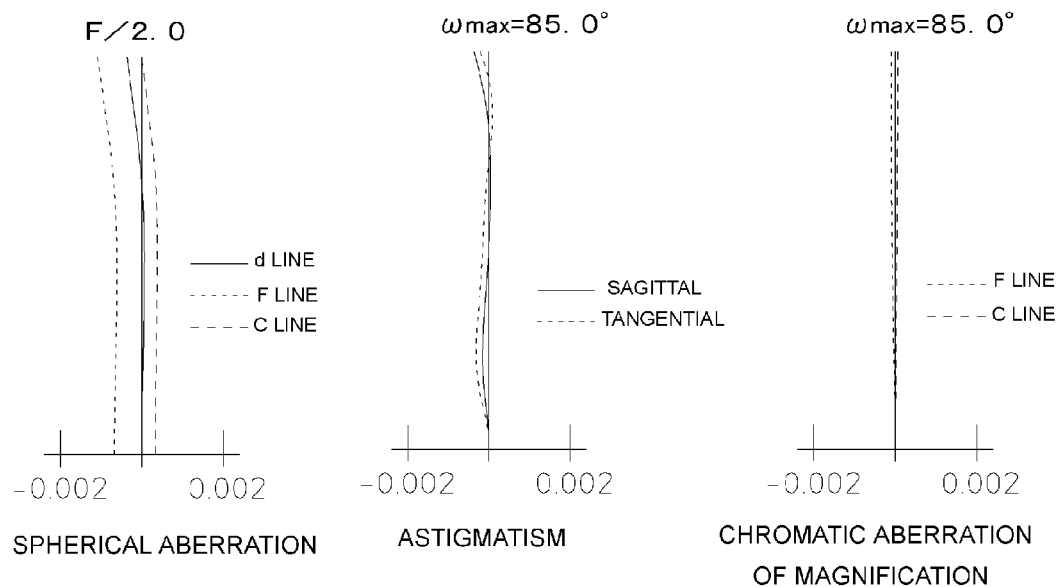
FIG. 22 is an aberration diagram of the image pickup optical system according to the sixth embodiment.

The configuration of an image pickup optical system 70 of Embodiment 6 is shown in FIG. 21. As in the case of the above Embodiments, Table 11 shows lens data, Table 12 shows data of aspherical surfaces, and FIG. 22 shows the spherical aberration, astigmatism, and chromatic aberration of magnification.

TABLE 11 f = 1.0   Fno = 2.0   2ωmax = 170°

| SURFACE | RADIUS OF CURVATURE | SURFACE SEPARATION | $N_d$ | $v_d$ |
|---|---|---|---|---|
| OBJ | 39.2626 | 25.3307 | | |
| 2 | 13.9319 | 1.2665 | 1.57500 | 32.2 |

TABLE 11-continued f = 1.0   Fno = 2.0   2ωmax = 170°

| SURFACE | RADIUS OF CURVATURE | SURFACE SEPARATION | $N_d$ | $v_d$ |
|---|---|---|---|---|
| 3 | 12.6654 | 12.6653 | | |
| 4* | 2.3143 | 0.7599 | 1.53039 | 55.2 |
| 5* | 0.5932 | 2.0895 | | |
| 6* | 3.7646 | 1.8364 | 1.63178 | 23.2 |
| 7* | −2.8294 | 0.2100 | | |
| APERTURE STOP | ∞ | 0.4150 | | |
| 9* | −4.2953 | 1.1591 | 1.54378 | 55.7 |
| 10* | −1.5655 | 0.2027 | | |
| 11* | 4.4560 | 1.0850 | 1.54378 | 55.7 |
| 12* | 95.9486 | 0.3752 | | |
| 13 | ∞ | 1.3805 | 1.55920 | 53.9 |
| 14 | ∞ | 0.0000 | | |
| IMG | ∞ | | | |

TABLE 12

| SURFACE | K | $A_3$ | $A_4$ | $A_5$ |
|---|---|---|---|---|
| 4 | −1.0000 | −8.5871E−02 | 3.6445E−03 | 1.6849E−03 |
| 5 | −1.0000 | −2.4983E−01 | 1.3210E−01 | −4.5289E−02 |
| 6 | −1.0000 | −5.7657E−02 | 1.2495E−01 | −1.7895E−01 |

TABLE 12-continued

| | | | | |
|---|---|---|---|---|
| 7 | −1.0000 | −3.3529E−02 | 9.7090E−02 | −5.4465E−02 |
| 9 | −1.0000 | −2.7838E−02 | 2.9039E−02 | −4.5048E−01 |
| 10 | −1.0000 | −3.3155E−03 | −8.1172E−02 | −4.8750E−02 |
| 11 | −1.0000 | 4.7961E−02 | −1.4179E−01 | 7.9568E−03 |
| 12 | −1.0000 | 3.2245E−03 | 1.5838E−01 | −1.3194E−01 |

| SURFACE | $A_6$ | $A_7$ | $A_8$ | $A_9$ |
|---|---|---|---|---|
| 4 | 1.6308E−04 | −2.0561E−06 | −1.1407E−05 | −1.8690E−06 |
| 5 | −2.1206E−02 | −1.7203E−04 | 2.9919E−03 | 1.5663E−03 |
| 6 | 3.8306E−02 | 4.4622E−02 | −4.6028E−03 | −1.4659E−02 |
| 7 | −3.0452E−01 | 3.3397E−01 | 2.1034E−01 | −2.5540E−01 |
| 9 | 6.8552E−01 | 5.8352E−01 | −3.0561E+00 | 3.5528E+00 |
| 10 | 4.4822E−02 | 5.9125E−02 | 8.2984E−03 | −4.6437E−02 |
| 11 | 6.7049E−02 | −1.6987E−02 | −1.5855E−02 | 5.6036E−03 |
| 12 | −3.4618E−02 | 2.5025E−02 | 9.9375E−03 | −1.0946E−04 |

| SURFACE | $A_{10}$ | $A_{11}$ | $A_{12}$ | $A_{13}$ |
|---|---|---|---|---|
| 4 | −2.1800E−07 | 1.0283E−08 | 1.9658E−08 | 5.3521E−09 |
| 5 | 6.2289E−04 | 5.3536E−05 | −1.2433E−04 | −1.0725E−04 |
| 6 | −1.4456E−03 | 3.2012E−04 | −9.3419E−04 | 1.9888E−03 |
| 7 | −2.9877E−01 | 4.3697E−01 | −1.6450E−01 | 1.0304E−02 |
| 9 | −1.7717E+00 | 4.2167E−01 | 1.3244E−01 | −1.7521E−01 |
| 10 | −3.7424E−03 | −2.0677E−03 | 5.1690E−03 | 7.3802E−03 |
| 11 | 4.9723E−03 | −7.0489E−05 | −4.5512E−03 | 6.8068E−04 |
| 12 | −4.5074E−04 | −7.6467E−04 | −5.7872E−04 | −3.4936E−04 |

| SURFACE | $A_{14}$ | $A_{15}$ | $A_{16}$ | $A_{17}$ |
|---|---|---|---|---|
| 4 | 1.2238E−09 | 2.2572E−10 | −7.3024E−11 | −2.8805E−11 |
| 5 | −1.6269E−05 | 9.5627E−06 | 1.5117E−06 | 8.4478E−07 |
| 6 | 8.0085E−05 | −2.4483E−04 | −1.0633E−05 | −9.7077E−09 |
| 7 | 3.2493E−03 | 1.2928E−05 | 3.2298E−07 | −3.3168E−12 |
| 9 | 1.4012E−02 | −1.4045E−12 | −1.7871E−10 | −7.0560E−12 |
| 10 | −3.1672E−03 | −5.5248E−06 | −7.5648E−15 | −7.0484E−12 |
| 11 | 1.1477E−03 | −3.2732E−04 | −1.8090E−07 | 5.6683E−11 |
| 12 | 3.4843E−04 | 2.0644E−05 | −2.0835E−05 | 1.5389E−11 |

| SURFACE | $A_{18}$ | $A_{19}$ | $A_{20}$ |
|---|---|---|---|
| 4 | −6.2984E−12 | 1.5460E−13 | 4.2817E−13 |
| 5 | 7.9212E−10 | −1.9263E−15 | −1.8374E−20 |
| 6 | 1.2517E−13 | 4.6920E−14 | 1.8045E−18 |
| 7 | −2.8899E−13 | −1.0982E−14 | −4.3186E−16 |
| 9 | −2.7740E−13 | −1.0951E−14 | −4.3233E−16 |
| 10 | −2.7852E−13 | −1.0997E−14 | −4.3233E−16 |
| 11 | −1.1790E−17 | −4.6543E−19 | −4.2827E−19 |
| 12 | −1.1790E−17 | −4.6543E−19 | −4.3366E−16 |

Figure 23:
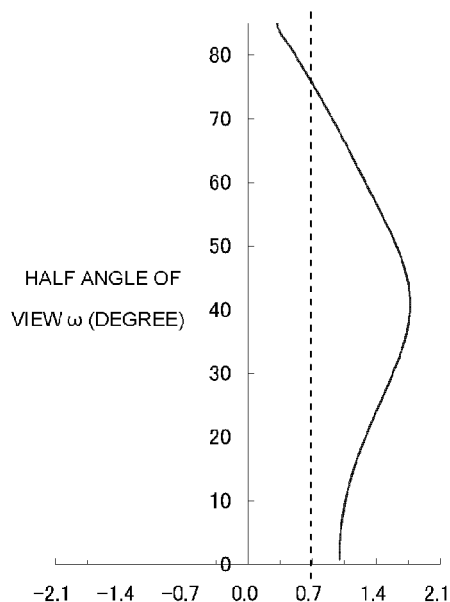
FIG. 23 is a graph showing distortion of the image pickup optical system according to the sixth embodiment.

In the image pickup optical system 70, in which the maximum angle of view is 170°, ΔZr is −0.015, ΔZp is 0.186, and ΔZr/ΔZp is −0.080. Therefore, the image pickup optical system 70 satisfies not only the mathematical expression 2 but also the mathematical expression 1. Moreover, as shown in FIG. 23, (Y(ω+Δω)−Y(ω))/Y(Δω) is more than 0.7. Therefore, the image pickup optical system 70 also satisfies the condition of the mathematical expression 3, and the image of the object 12 including its central portion and peripheral portion is successively within the depth of field. Accordingly, the peripheral portion of the image is not distorted so much, and it is possible to successively performing the image forming.

[Embodiment 7]

Figure 24:
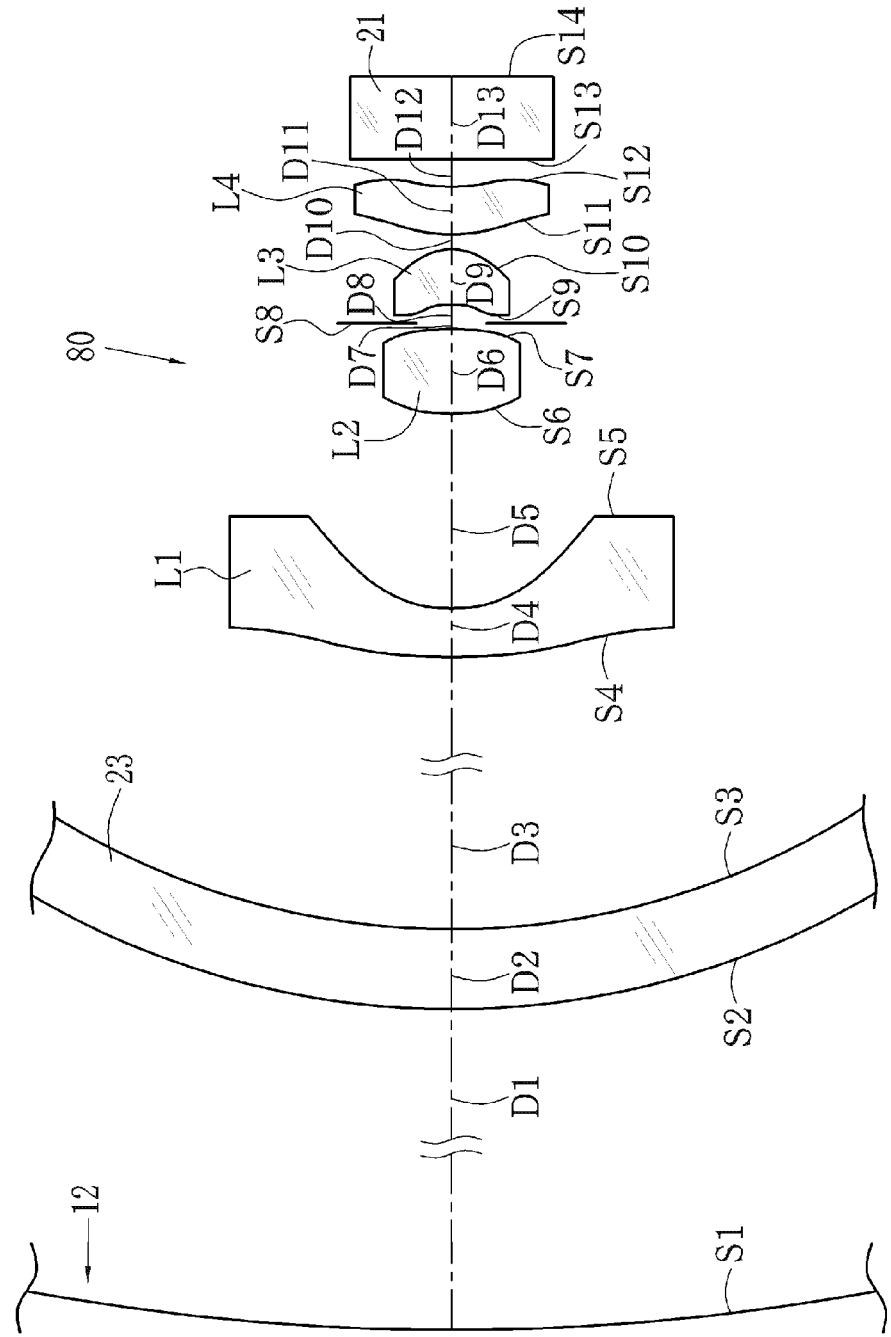
FIG. 24 is a lens configuration diagram of an image pickup optical system according to a seventh embodiment of the present invention.
Figure 25:
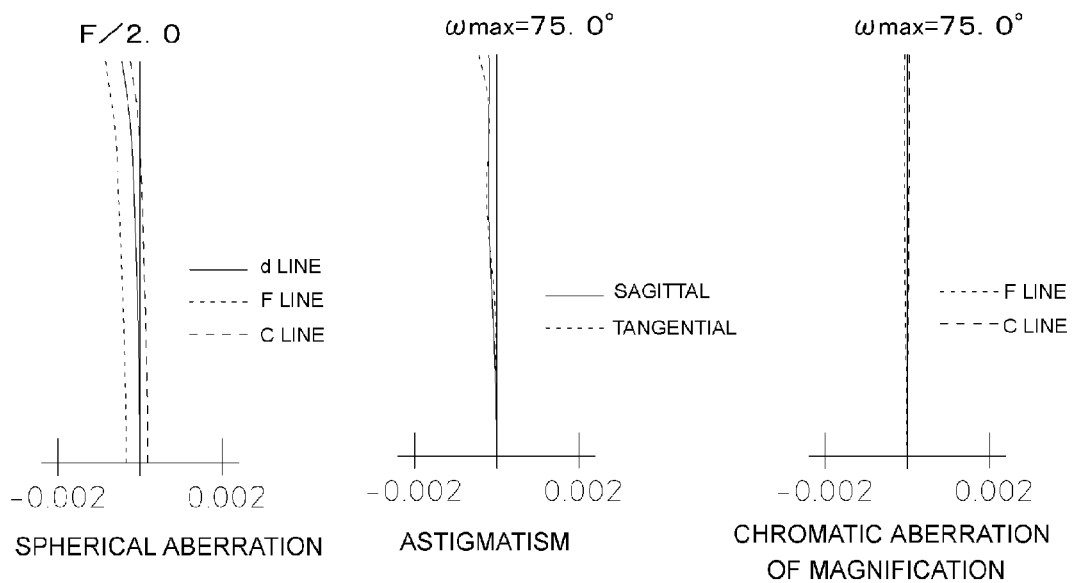
FIG. 25 is an aberration diagram of the image pickup optical system according to the seventh embodiment.

The configuration of an image pickup optical system 80 of Embodiment 7 is shown in FIG. 24. As in the case of the above Embodiments, Table 13 shows lens data, Table 14 shows data of aspherical surfaces, and FIG. 25 shows the spherical aberration, astigmatism, and chromatic aberration of magnification.

TABLE 13 f = 1.0   Fno = 2.0   2ωmax = 150°

| SURFACE | RADIUS OF CURVATURE | SURFACE SEPARATION | $N_d$ | $v_d$ |
|---|---|---|---|---|
| OBJ | 31.0156 | 20.0101 | | |
| 2 | 11.0055 | 1.0005 | 1.57500 | 32.2 |
| 3 | 10.0050 | 9.8197 | | |
| 4* | 7.1731 | 0.6003 | 1.63000 | 60.0 |
| 5* | 1.5111 | 2.5494 | | |
| 6* | 1.9237 | 1.1366 | 1.62357 | 35.6 |
| 7* | −3.1228 | 0.0243 | | |
| APERTURE STOP | ∞ | 0.2293 | | |
| 9* | −0.8388 | 0.7189 | 1.63000 | 60.0 |
| 10* | −0.7951 | 0.2032 | | |
| 11* | 2.1379 | 0.6093 | 1.55906 | 62.7 |
| 12* | 2.6310 | 0.3509 | | |
| 13 | ∞ | 1.0906 | 1.55920 | 53.9 |
| 14 | ∞ | 0.0000 | | |
| IMG | ∞ | | | |

TABLE 14

| SURFACE | K | $A_3$ | $A_4$ | $A_5$ |
|---|---|---|---|---|
| 4 | −1.0000 | 0.0000E+00 | −1.6851E−03 | 0.0000E+00 |
| 5 | −1.0000 | 0.0000E+00 | 6.6842E−03 | 0.0000E+00 |
| 6 | −1.0000 | 0.0000E+00 | 7.0290E−02 | 0.0000E+00 |
| 7 | −1.0000 | 0.0000E+00 | −9.3884E−02 | 0.0000E+00 |
| 9 | −1.0000 | 0.0000E+00 | −4.8665E−01 | 0.0000E+00 |
| 10 | −1.0000 | 0.0000E+00 | −5.1686E−02 | 0.0000E+00 |
| 11 | −1.0000 | 0.0000E+00 | −1.6545E−02 | 0.0000E+00 |
| 12 | −1.0000 | 0.0000E+00 | −1.0026E−01 | 0.0000E+00 |

| SURFACE | $A_6$ | $A_7$ | $A_8$ | $A_9$ |
|---|---|---|---|---|
| 4 | −1.4277E−04 | 0.0000E+00 | −6.6804E−06 | 0.0000E+00 |
| 5 | 6.1982E−04 | 0.0000E+00 | −5.5435E−04 | 0.0000E+00 |
| 6 | −2.1519E−01 | 0.0000E+00 | 4.8451E−01 | 0.0000E+00 |
| 7 | −2.1391E−01 | 0.0000E+00 | 5.5458E−01 | 0.0000E+00 |
| 9 | −3.5296E−01 | 0.0000E+00 | 1.4686E+00 | 0.0000E+00 |
| 10 | −1.0823E−01 | 0.0000E+00 | 6.7602E−02 | 0.0000E+00 |
| 11 | −2.4301E−02 | 0.0000E+00 | 2.1117E−03 | 0.0000E+00 |
| 12 | −7.6680E−03 | 0.0000E+00 | −4.4835E−03 | 0.0000E+00 |

| SURFACE | $A_{10}$ | $A_{11}$ | $A_{12}$ | $A_{13}$ |
|---|---|---|---|---|
| 4 | −5.9563E−08 | 0.0000E+00 | 7.1999E−08 | 0.0000E+00 |
| 5 | 4.1171E−05 | 0.0000E+00 | −1.5114E−06 | 0.0000E+00 |
| 6 | −5.5780E−01 | 0.0000E+00 | 1.6068E−01 | 0.0000E+00 |
| 7 | −4.5109E−01 | 0.0000E+00 | 9.4952E−02 | 0.0000E+00 |
| 9 | −7.3422E−01 | 0.0000E+00 | 5.4092E−01 | 0.0000E+00 |
| 10 | −2.6969E−01 | 0.0000E+00 | 3.2478E−01 | 0.0000E+00 |
| 11 | 2.2571E−03 | 0.0000E+00 | −1.7515E−03 | 0.0000E+00 |
| 12 | 1.2691E−03 | 0.0000E+00 | −2.2466E−04 | 0.0000E+00 |

| SURFACE | $A_{14}$ | $A_{15}$ | $A_{16}$ | $A_{17}$ |
|---|---|---|---|---|
| 4 | 0.0000E+00 | 0.0000E+00 | 0.0000E+00 | 0.0000E+00 |
| 5 | 0.0000E+00 | 0.0000E+00 | 0.0000E+00 | 0.0000E+00 |
| 6 | 0.0000E+00 | 0.0000E+00 | 0.0000E+00 | 0.0000E+00 |
| 7 | 0.0000E+00 | 0.0000E+00 | 0.0000E+00 | 0.0000E+00 |
| 9 | 0.0000E+00 | 0.0000E+00 | 0.0000E+00 | 0.0000E+00 |
| 10 | 0.0000E+00 | 0.0000E+00 | 0.0000E+00 | 0.0000E+00 |
| 11 | 0.0000E+00 | 0.0000E+00 | 0.0000E+00 | 0.0000E+00 |
| 12 | 0.0000E+00 | 0.0000E+00 | 0.0000E+00 | 0.0000E+00 |

| SURFACE | $A_{18}$ | $A_{19}$ | $A_{20}$ |
|---|---|---|---|
| 4 | 0.0000E+00 | 0.0000E+00 | 0.0000E+00 |
| 5 | 0.0000E+00 | 0.0000E+00 | 0.0000E+00 |
| 6 | 0.0000E+00 | 0.0000E+00 | 0.0000E+00 |
| 7 | 0.0000E+00 | 0.0000E+00 | 0.0000E+00 |
| 9 | 0.0000E+00 | 0.0000E+00 | 0.0000E+00 |
| 10 | 0.0000E+00 | 0.0000E+00 | 0.0000E+00 |
| 11 | 0.0000E+00 | 0.0000E+00 | 0.0000E+00 |
| 12 | 0.0000E+00 | 0.0000E+00 | 0.0000E+00 |

Figure 26:
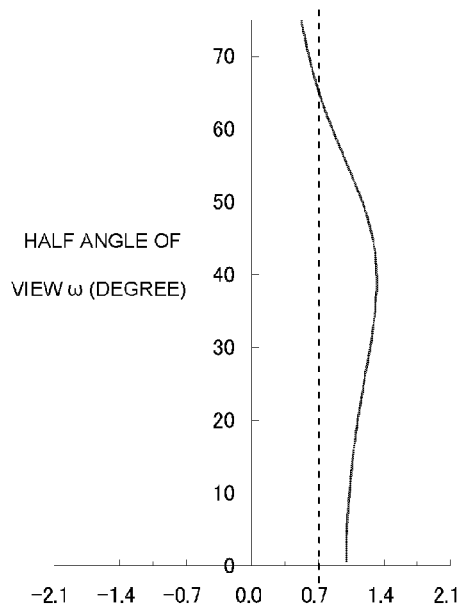
FIG. 26 is a graph showing distortion of the image pickup optical system according to the seventh embodiment.

In the image pickup optical system 80, in which the maximum angle of view is 150°, ΔZr is 0.010, ΔZp is 0.075, and ΔZr/ΔZp is 0.128. Therefore, the image pickup optical system 80 satisfies the condition of the mathematical expressions 1 and 2. Moreover, as shown in FIG. 26, (Y(ω+Δω)−Y(ω))/Y(Δω) is more than 0.7. Therefore, the image pickup optical system 80 also satisfies the condition of the mathematical expression 3, and the image of the object 12 including its central portion and peripheral portion is successively within the depth of field. Accordingly, the peripheral portion of the image is not distorted so much, and it is possible to successively performing the image forming.

[Embodiment 8]

Figure 27:
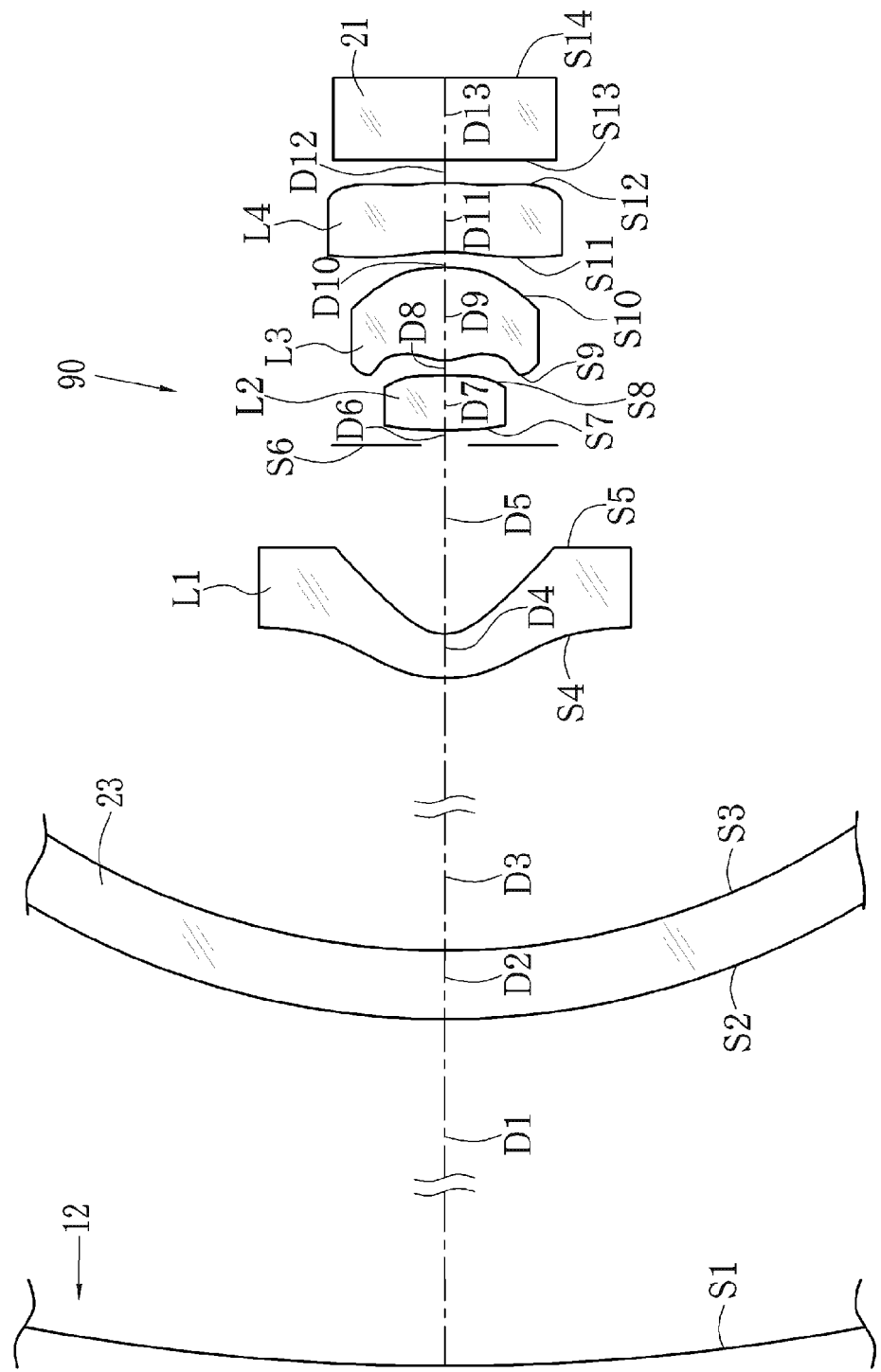
FIG. 27 is a lens configuration diagram of an image pickup optical system according to an eighth embodiment of the present invention.
Figure 28:
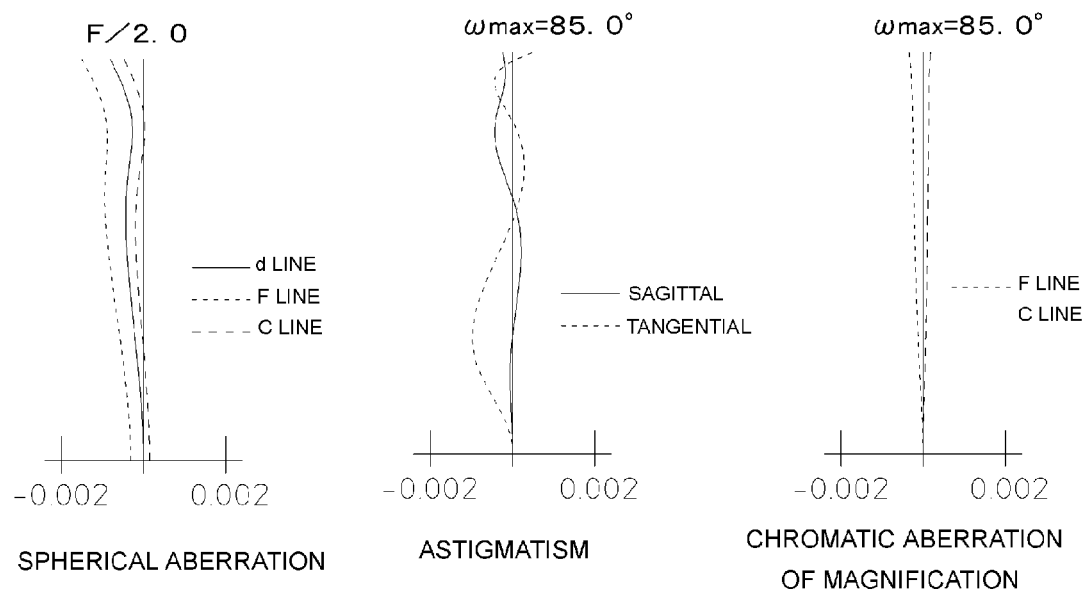
FIG. 28 is an aberration diagram of the image pickup optical system according to the eighth embodiment.

The configuration of an image pickup optical system 90 of Embodiment 8 is shown in FIG. 27. As in the case of the above Embodiments, Table 15 shows lens data, Table 16 shows data of aspherical surfaces, and FIG. 28 shows the spherical aberration, astigmatism, and chromatic aberration of magnification.

TABLE 15 f = 1.0  Fno = 2.0  2ωmax = 170°

| SURFACE | RADIUS OF CURVATURE | SURFACE SEPARATION | $N_d$ | $v_d$ |
|---|---|---|---|---|
| OBJ | 52.3393 | 33.7673 | | |
| 2 | 18.5720 | 1.6884 | 1.58600 | 55.0 |
| 3 | 16.8836 | 16.8837 | | |
| 4* | 2.0691 | 1.0130 | 1.53039 | 55.2 |
| 5* | 0.7157 | 4.2191 | | |
| APERTURE STOP | ∞ | 0.3312 | | |
| 7* | 5.9517 | 1.1875 | 1.63178 | 23.2 |
| 8* | 7.6999 | 0.4004 | | |
| 9* | 2.1836 | 2.0415 | 1.54378 | 55.7 |
| 10* | −13.7488 | 0.3339 | | |
| 11* | −15.8602 | 1.6064 | 1.54378 | 55.7 |
| 12* | −1.4551 | 0.4670 | | |
| 13 | ∞ | 1.8403 | 1.55920 | 53.9 |
| 14 | ∞ | 0.0000 | | |
| IMG | ∞ | | | |

TABLE 16

| SURFACE | K | $A_3$ | $A_4$ | $A_5$ |
|---|---|---|---|---|
| 4 | −1.0000 | −3.5700E−02 | −3.1703E−03 | −3.2383E−04 |
| 5 | −1.0000 | −4.4213E−01 | 2.8306E−01 | −7.1316E−02 |
| 7 | −1.0000 | −2.3697E−02 | −1.7459E−01 | 6.7293E−01 |
| 8 | −1.0000 | 1.9655E−03 | −2.4355E−01 | −1.7837E−02 |
| 9 | −1.0000 | −6.2772E−02 | 3.1543E−02 | −2.4815E−01 |
| 10 | −1.0000 | −1.1759E−01 | 3.8284E−02 | −3.0955E−02 |
| 11 | −1.0000 | 5.1705E−02 | −6.7555E−02 | 3.7561E−03 |
| 12 | −1.0000 | 2.6587E−01 | 3.9872E−02 | −5.5335E−02 |

| SURFACE | $A_6$ | $A_7$ | $A_8$ | $A_9$ |
|---|---|---|---|---|
| 4 | −4.8301E−05 | −1.8810E−06 | 5.7872E−06 | 3.0860E−06 |
| 5 | −2.6700E−02 | 4.0634E−03 | 7.3417E−03 | 1.9461E−03 |
| 7 | −6.9440E−01 | −3.9297E−01 | 8.4036E−01 | 5.9985E−02 |
| 8 | 5.0926E−01 | −4.4819E−01 | −8.2505E−02 | 2.4562E−01 |
| 9 | −1.0694E−01 | 6.2314E−01 | −2.1044E−01 | −5.0565E−01 |
| 10 | −5.3022E−04 | 1.1277E−02 | 4.8678E−04 | −1.9928E−03 |
| 11 | 1.7082E−02 | −2.6104E−03 | −1.9276E−03 | 6.3326E−04 |
| 12 | −1.0392E−02 | 4.7938E−03 | 1.6785E−03 | 1.3692E−04 |

TABLE 14-continued

| 10 | 0.0000E+00 | 0.0000E+00 | 0.0000E+00 |
| 11 | 0.0000E+00 | 0.0000E+00 | 0.0000E+00 |
| 12 | 0.0000E+00 | 0.0000E+00 | 0.0000E+00 |

TABLE 16-continued

| SURFACE | $A_{10}$ | $A_{11}$ | $A_{12}$ | $A_{13}$ |
|---|---|---|---|---|
| 4 | 1.1347E−06 | 1.5734E−07 | −9.2745E−08 | −6.6930E−08 |
| 5 | −3.4371E−03 | 1.0520E−03 | −1.5511E−04 | 3.3157E−05 |
| 7 | −4.9133E−01 | 1.9195E−01 | −1.4455E−02 | 3.3205E−04 |
| 8 | −9.0588E−02 | 7.7982E−03 | 1.1247E−04 | −7.9737E−05 |
| 9 | 4.8359E−01 | −1.5089E−01 | 1.5231E−02 | −9.7760E−04 |
| 10 | 5.7040E−04 | −3.6120E−04 | −2.3859E−04 | 2.5806E−04 |
| 11 | 3.9993E−04 | 9.4593E−06 | −1.9412E−04 | 1.7265E−05 |
| 12 | 4.2750E−06 | −3.9195E−05 | −2.7301E−05 | −1.3288E−05 |

| SURFACE | $A_{14}$ | $A_{15}$ | $A_{16}$ | $A_{17}$ |
|---|---|---|---|---|
| 4 | 1.4174E−08 | −3.6178E−10 | 4.9531E−10 | −6.9814E−11 |
| 5 | −6.6938E−06 | 2.1328E−07 | 2.3416E−08 | 6.3586E−09 |
| 7 | 1.1280E−05 | −4.3752E−06 | −1.4254E−07 | −9.7621E−11 |
| 8 | 7.4969E−05 | 2.3102E−07 | 4.3296E−09 | −3.3337E−14 |
| 9 | 3.7414E−04 | −2.5098E−14 | −2.3957E−12 | −7.0940E−14 |
| 10 | −5.1325E−05 | 5.8702E−07 | −1.2963E−12 | −7.0879E−14 |
| 11 | 2.3622E−05 | −4.6939E−06 | 3.1130E−08 | 5.6029E−13 |
| 12 | 7.5612E−06 | 5.7693E−07 | −3.0597E−07 | −1.3901E−10 |

| SURFACE | $A_{18}$ | $A_{19}$ | $A_{20}$ |
|---|---|---|---|
| 4 | −1.4761E−11 | 1.7343E−12 | 6.5058E−14 |
| 5 | 5.9754E−12 | −1.0901E−17 | 2.8332E−20 |
| 7 | 9.7661E−16 | 2.6648E−16 | 3.6479E−20 |
| 8 | −2.1795E−15 | −6.1172E−17 | −1.8044E−18 |
| 9 | −2.0921E−15 | −6.0998E−17 | −1.8064E−18 |
| 10 | −2.1010E−15 | −6.2229E−17 | −1.8064E−18 |
| 11 | −2.8777E−15 | −2.6338E−21 | −1.8180E−21 |
| 12 | −6.8780E−15 | −2.6338E−21 | −1.8409E−18 |

Figure 29:
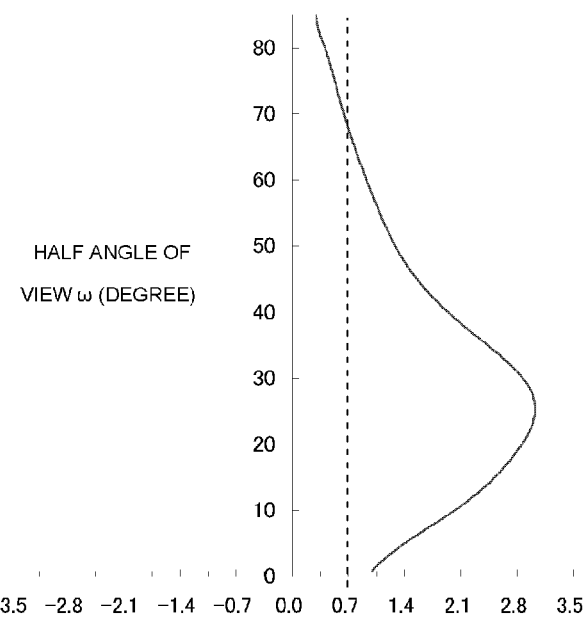
FIG. 29 is a graph showing distortion of the image pickup optical system according to the eighth embodiment.

In the image pickup optical system 90, the maximum angle of view is 170°, ΔZr is −0.031, and ΔZp is 0.133. ΔZr/ΔZp is −0.235, which is within the range of the mathematical expressions 1 and 2. Moreover, as shown in FIG. 29, (Y(ω+Δω)−Y(ω))/Y(Δω) is more than 0.7. Therefore, the image pickup optical system 90 also satisfies the condition of the mathematical expression 3, and the image of the object 12 including its central portion and peripheral portion is successively within the depth of field. Accordingly, the peripheral portion of the image is not distorted so much, and it is possible to successively performing the image forming.

[Embodiment 9]

Figure 30:
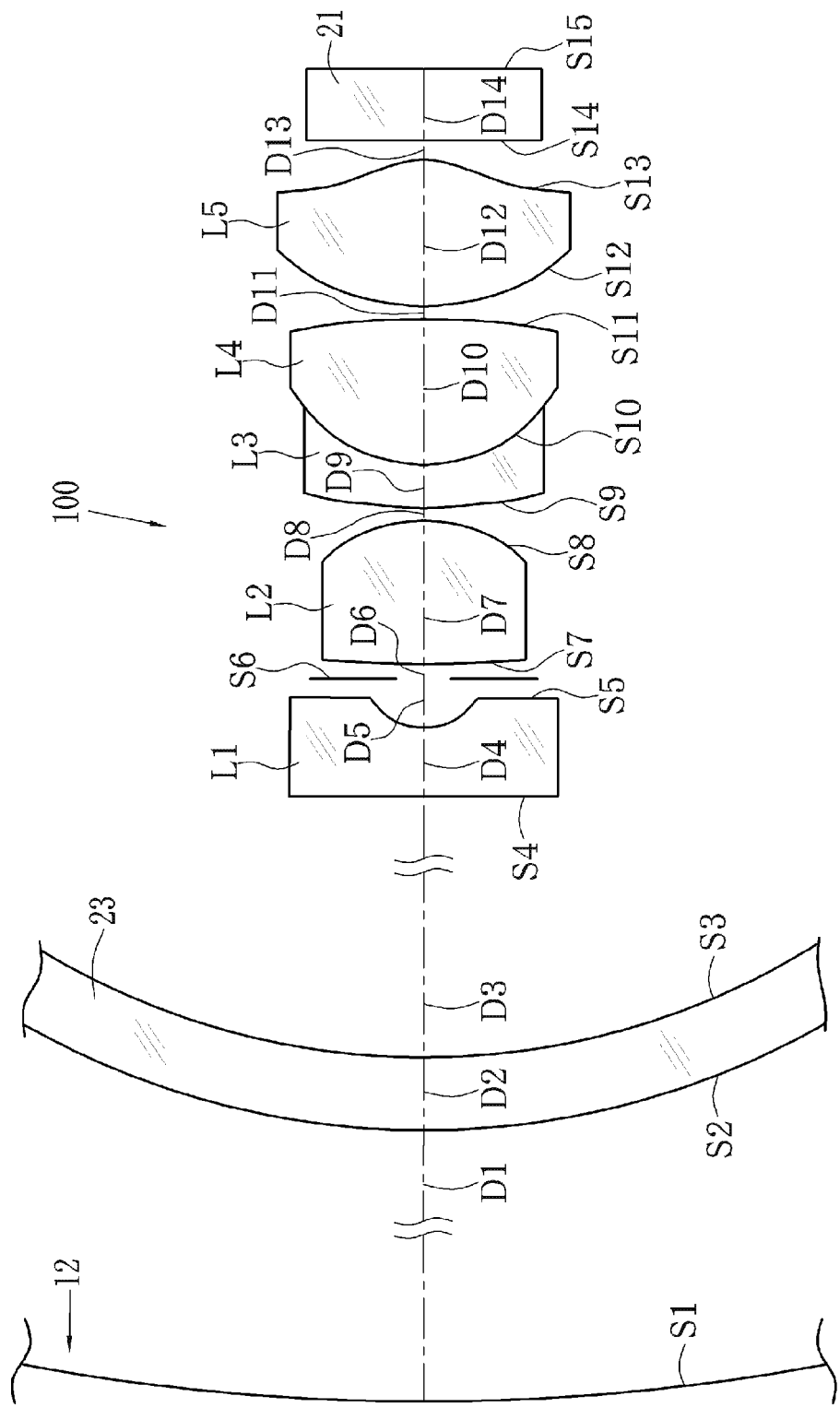
FIG. 30 is a lens configuration diagram of an image pickup optical system according to a ninth embodiment of the present invention.
Figure 31:
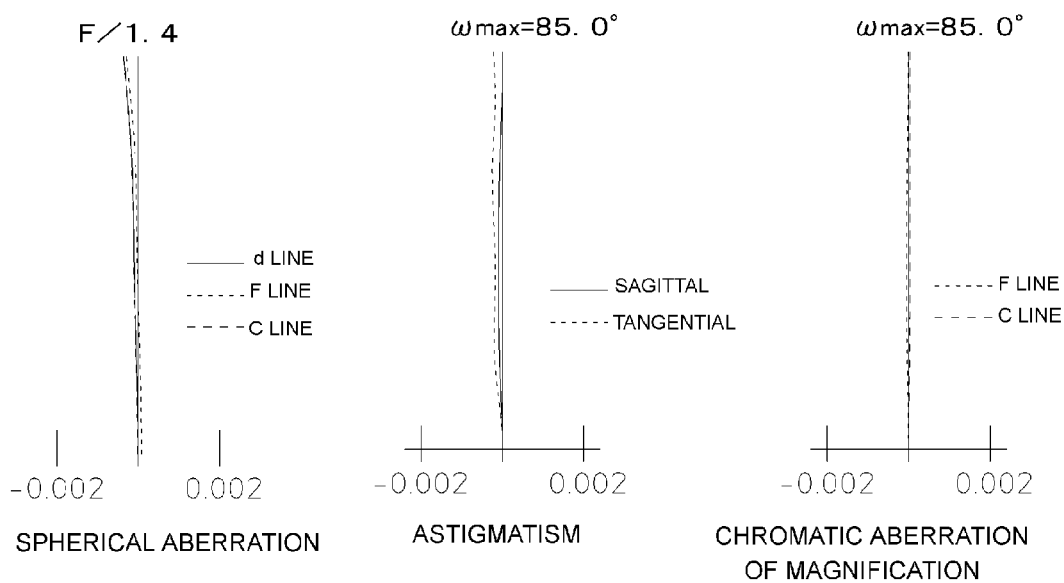
FIG. 31 is an aberration diagram of the image pickup optical system according to the ninth embodiment.

The configuration of an image pickup optical system 100 of Embodiment 9 is shown in FIG. 30. As in the case of the above Embodiments, Table 17 shows lens data, Table 18 shows data of aspherical surfaces, and FIG. 31 shows the spherical aberration, astigmatism, and chromatic aberration of magnification.

TABLE 17 f = 1.0 Fno = 1.4 2ωmax = 170°

| SURFACE | RADIUS OF CURVATURE | SURFACE SEPARATION | $N_d$ | $v_d$ |
|---|---|---|---|---|
| OBJ | 35.6520 | 22.5413 | | |
| 2 | 13.1108 | 1.1501 | 1.58600 | 55.0 |
| 3 | 11.9607 | 9.5059 | | |
| 4* | −35.5208 | 1.1501 | 1.53039 | 55.2 |
| 5* | 0.8801 | 0.7764 | | |
| APERTURE STOP | ∞ | 0.2300 | | |
| 7 | 33.8004 | 2.2672 | 1.74320 | 49.3 |
| 8 | −2.5557 | 0.2300 | | |
| 9 | 8.6484 | 0.6900 | 1.92286 | 18.9 |
| 10 | 2.5557 | 2.3001 | 1.72916 | 54.7 |
| 11 | −11.8213 | 0.2300 | | |
| 12* | 3.8788 | 2.3001 | 1.53039 | 55.2 |
| 13* | −1.3291 | 0.3245 | | |
| 14 | ∞ | 1.1501 | 1.55920 | 53.9 |
| 15 | ∞ | 0.0000 | | |
| IMG | ∞ | | | |

TABLE 18

| SURFACE | K | $A_3$ | $A_4$ | $A_5$ |
|---|---|---|---|---|
| 4 | −1.0000 | 5.5091E−02 | −2.7558E−02 | −2.1981E−03 |
| 5 | −1.0000 | −3.4084E−01 | 1.6403E+00 | −2.0923E+00 |
| 12 | −1.0000 | −1.2527E−02 | 2.7986E−02 | −1.2837E−02 |
| 13 | −1.0000 | 1.0704E−01 | 4.6420E−02 | −8.9891E−03 |

TABLE 18-continued

| SURFACE | $A_6$ | $A_7$ | $A_8$ | $A_9$ |
|---|---|---|---|---|
| 4 | 4.7034E−04 | 4.6228E−04 | 2.6092E−04 | 1.1739E−04 |
| 5 | −1.1442E+00 | 2.7202E+00 | 2.1544E+00 | −3.8604E+00 |
| 12 | 1.1054E−03 | 9.1051E−04 | 1.3628E−05 | −7.9323E−05 |
| 13 | −6.3406E−03 | −1.1914E−03 | 2.5164E−04 | 3.0147E−04 |

| SURFACE | $A_{10}$ | $A_{11}$ | $A_{12}$ | $A_{13}$ |
|---|---|---|---|---|
| 4 | 3.7681E−05 | 4.8817E−06 | −6.8767E−06 | −1.0520E−05 |
| 5 | 1.3620E+00 | −7.4332E−01 | 1.1473E−01 | 2.6608E−01 |
| 12 | −1.9703E−05 | −9.1654E−07 | 3.5337E−06 | 1.6433E−06 |
| 13 | 1.4918E−04 | 1.1106E−05 | −7.8818E−06 | −6.2716E−06 |

| SURFACE | $A_{14}$ | $A_{15}$ | $A_{16}$ | $A_{17}$ |
|---|---|---|---|---|
| 4 | −1.5643E−05 | 1.1646E−05 | −1.7979E−06 | −4.9008E−08 |
| 5 | −1.3595E−02 | −9.6052E−05 | 3.4414E−17 | 1.5014E−18 |
| 12 | 5.3936E−07 | −1.2937E−07 | −1.2455E−07 | −5.0324E−08 |
| 13 | −2.5610E−06 | −4.8456E−07 | 1.5747E−07 | 1.1910E−07 |

| SURFACE | $A_{18}$ | $A_{19}$ | $A_{20}$ |
|---|---|---|---|
| 4 | 1.9276E−08 | 5.3897E−10 | 1.0622E−11 |
| 5 | −8.6529E−15 | −1.5707E−15 | −6.8715E−17 |
| 12 | 2.1537E−08 | −2.3263E−10 | −1.9503E−11 |
| 13 | 7.2352E−09 | −2.8018E−10 | −2.2769E−10 |

Figure 32:
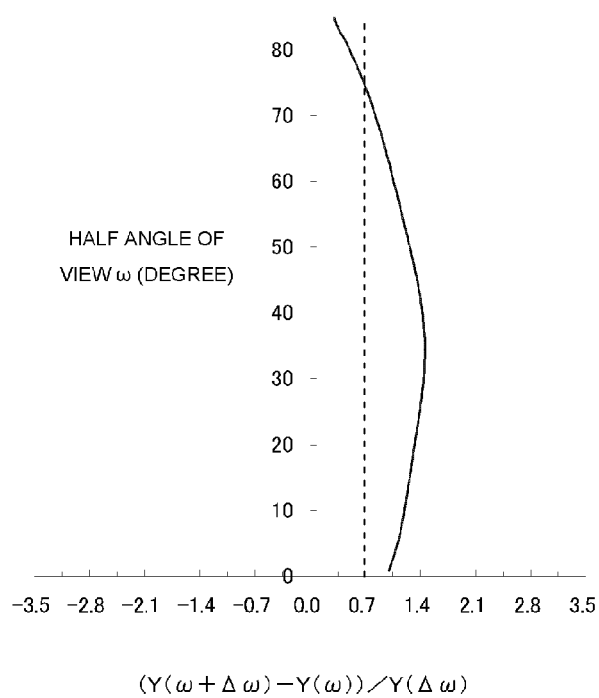
FIG. 32 is a graph showing distortion of the image pickup optical system according to the ninth embodiment.

In the image pickup optical system 100, the maximum angle of view is 170°, ΔZr is 0.036, ΔZp is 0.168, and ΔZr/ΔZp is 0.215, which is within the range of not only the mathematical expression 2 but also the mathematical expression 1. Moreover, as shown in FIG. 32, (Y(ω+Δω)−Y(ω))/Y(Δω) is more than 0.7. Therefore, the image pickup optical system 100 also satisfies the condition of the mathematical expression 3, and the image of the object 12 including its central portion and peripheral portion is successively within the depth of field. Accordingly, the peripheral portion of the image is not distorted so much, and it is possible to successively performing the image forming.

[Embodiment 10]

Figure 33:
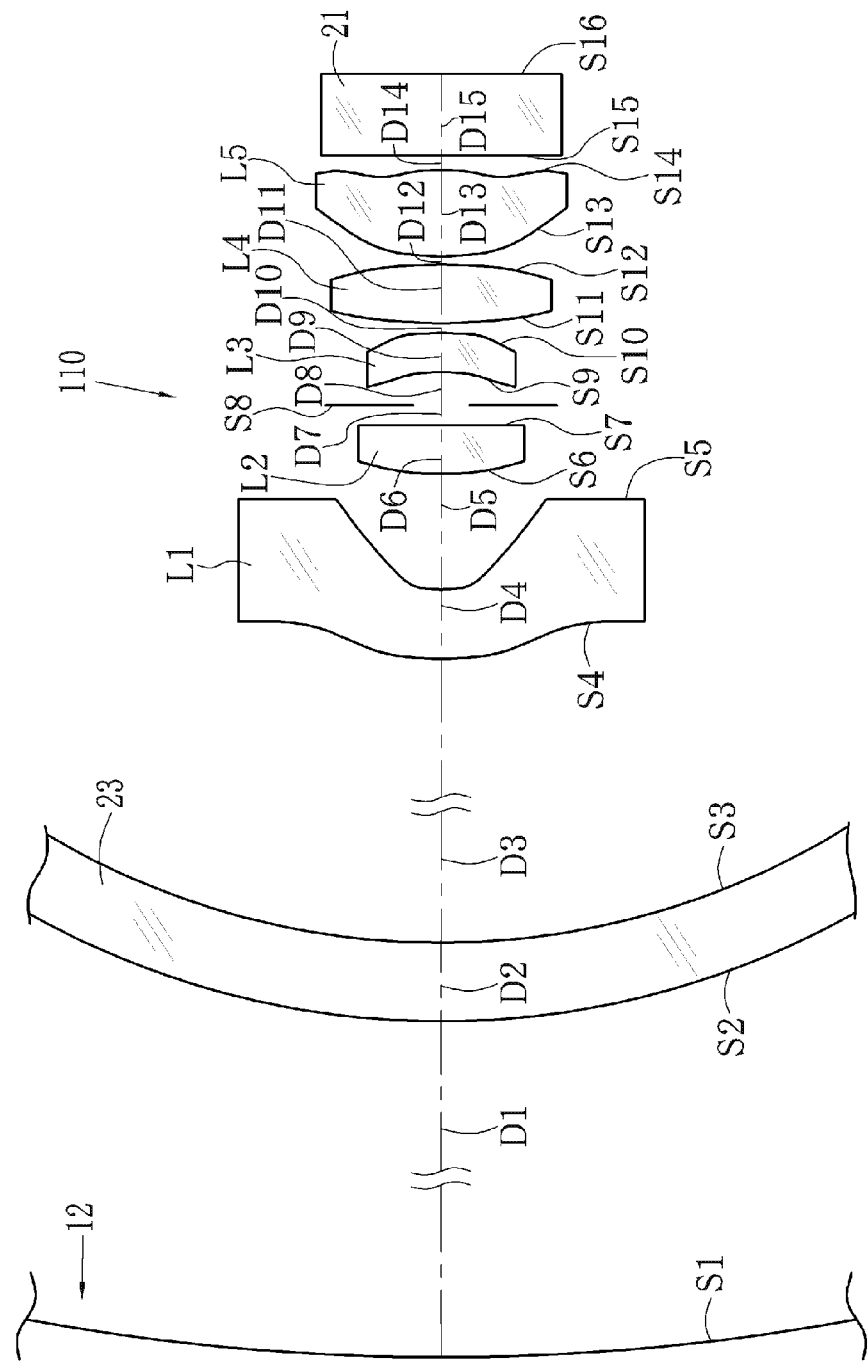
FIG. 33 is a lens configuration diagram of an image pickup optical system according to a tenth embodiment of the present invention.
Figure 34:
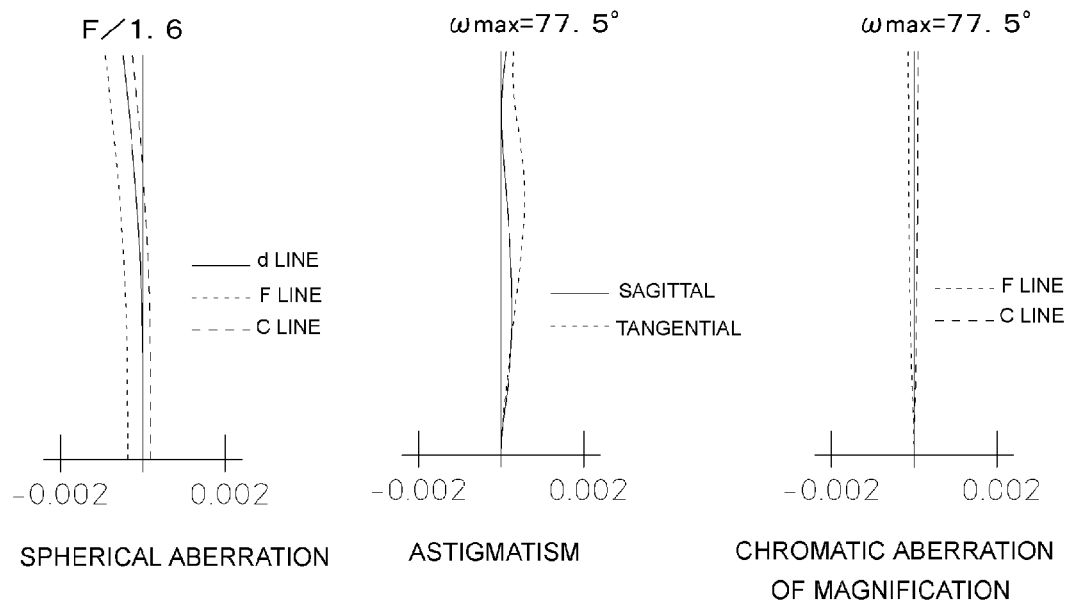
FIG. 34 is an aberration diagram of the image pickup optical system according to the tenth embodiment.

The configuration of an image pickup optical system 110 of Embodiment 10 is shown in FIG. 33. As in the case of the above Embodiments, Table 19 shows lens data, Table 20 shows data of aspherical surfaces, and FIG. 34 shows the spherical aberration, astigmatism, and chromatic aberration of magnification.

TABLE 19 f = 1.0 Fno = 1.6 2ωmax = 155°

| SURFACE | RADIUS OF CURVATURE | SURFACE SEPARATION | $N_d$ | $v_d$ |
|---|---|---|---|---|
| OBJ | 42.9914 | 27.1817 | | |
| 2 | 15.8097 | 1.3868 | 1.58600 | 55.0 |
| 3 | 14.4229 | 13.8681 | | |
| 4* | −271.3132 | 1.2463 | 1.53159 | 55.4 |
| 5* | 1.2736 | 2.1234 | | |
| 6 | 5.0379 | 0.8775 | 1.84666 | 23.8 |
| 7 | −42.2078 | 0.3893 | | |
| APERTURE STOP | ∞ | 0.5793 | | |
| 9 | −3.2395 | 0.7814 | 1.72916 | 54.7 |
| 10 | −2.7196 | 0.1387 | | |
| 11 | 10.3913 | 1.0834 | 1.72916 | 54.7 |
| 12 | −8.5087 | 0.1387 | | |
| 13* | 4.0002 | 1.5744 | 1.54378 | 55.7 |
| 14* | −2.3765 | 0.4205 | | |
| 15 | ∞ | 1.3868 | 1.55920 | 53.9 |
| 16 | ∞ | 0.0000 | | |
| IMG | ∞ | | | |

TABLE 20

| SURFACE | K | $A_3$ | $A_4$ | $A_5$ |
|---|---|---|---|---|
| 4 | −1.0000 | 1.1845E−01 | −2.6035E−02 | −3.9981E−03 |
| 5 | −1.0000 | 1.8659E−01 | −1.0512E−01 | 5.6801E−02 |
| 13 | −1.0000 | 1.9628E−02 | 4.5078E−03 | 4.7745E−03 |
| 14 | −1.0000 | 6.2929E−02 | 1.2675E−01 | −4.8654E−02 |

| SURFACE | $A_6$ | $A_7$ | $A_8$ | $A_9$ |
|---|---|---|---|---|
| 4 | 5.0211E−05 | 1.2748E−04 | 3.2446E−05 | 4.9233E−06 |
| 5 | −1.4380E−02 | −1.4481E−02 | −2.3922E−03 | 1.5344E−03 |

TABLE 20-continued

| | | | | |
|---|---|---|---|---|
| 13 | −4.8268E−03 | −8.8612E−04 | 4.0639E−04 | 2.6232E−04 |
| 14 | −1.2880E−02 | 9.2601E−04 | 1.6500E−03 | 6.0678E−04 |

| SURFACE | $A_{10}$ | $A_{11}$ | $A_{12}$ | $A_{13}$ |
|---|---|---|---|---|
| 4 | 2.4863E−07 | −9.2028E−08 | −5.0714E−08 | −1.4201E−08 |
| 5 | 1.2218E−03 | 4.0802E−04 | 3.4527E−06 | −7.6706E−05 |
| 13 | 4.8332E−05 | −1.3376E−05 | −1.1747E−05 | −3.5147E−06 |
| 14 | 7.0560E−05 | −5.3653E−05 | −3.9547E−05 | −9.3269E−06 |

| SURFACE | $A_{14}$ | $A_{15}$ | $A_{16}$ | $A_{17}$ |
|---|---|---|---|---|
| 4 | −2.7915E−09 | −3.2091E−10 | 2.8702E−11 | 3.8175E−11 |
| 5 | −4.2800E−05 | −8.2857E−07 | 5.1190E−06 | 6.7286E−09 |
| 13 | −1.6990E−07 | 3.0642E−07 | 1.4844E−07 | −2.6644E−08 |
| 14 | 1.3794E−06 | 1.6722E−06 | 3.9199E−07 | −1.5382E−07 |

| SURFACE | $A_{18}$ | $A_{19}$ | $A_{20}$ |
|---|---|---|---|
| 4 | 1.0979E−11 | 1.3070E−12 | −6.2270E−13 |
| 5 | 2.6366E−11 | 3.1970E−12 | 1.3166E−13 |
| 13 | 2.4159E−11 | 1.1222E−15 | 0.0000E+00 |
| 14 | −9.6897E−24 | 0.0000E+00 | 0.0000E+00 |

Figure 35:
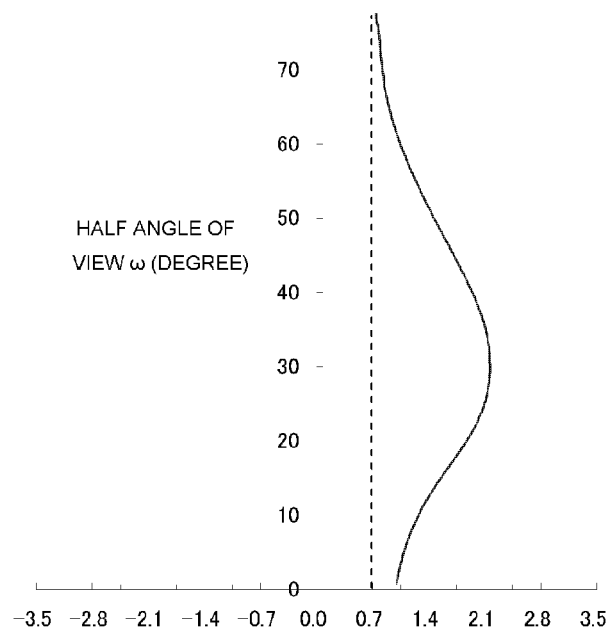
FIG. 35 is a graph showing distortion of the image pickup optical system according to the tenth embodiment.

In the image pickup optical system 110, the maximum angle of view is 155°, $\Delta Zr$ is −0.020, $\Delta Zp$ is 0.069, and $\Delta Zr/\Delta Zp$ is −0.295, which is within the range of not only the mathematical expression 2 but also the mathematical expression 1. Moreover, as shown in FIG. 35, $(Y(\omega+\Delta\omega)-Y(\omega))/Y(\Delta\omega)$ is more than 0.7. Therefore, the image pickup optical system 110 also satisfies the condition of the mathematical expression 3, and the image of the object 12 including its central portion and peripheral portion is successively within the depth of field. Accordingly, the distortion can be suppressed, and it is possible to successively performing the image forming.

[Embodiment 11]

Figure 36:
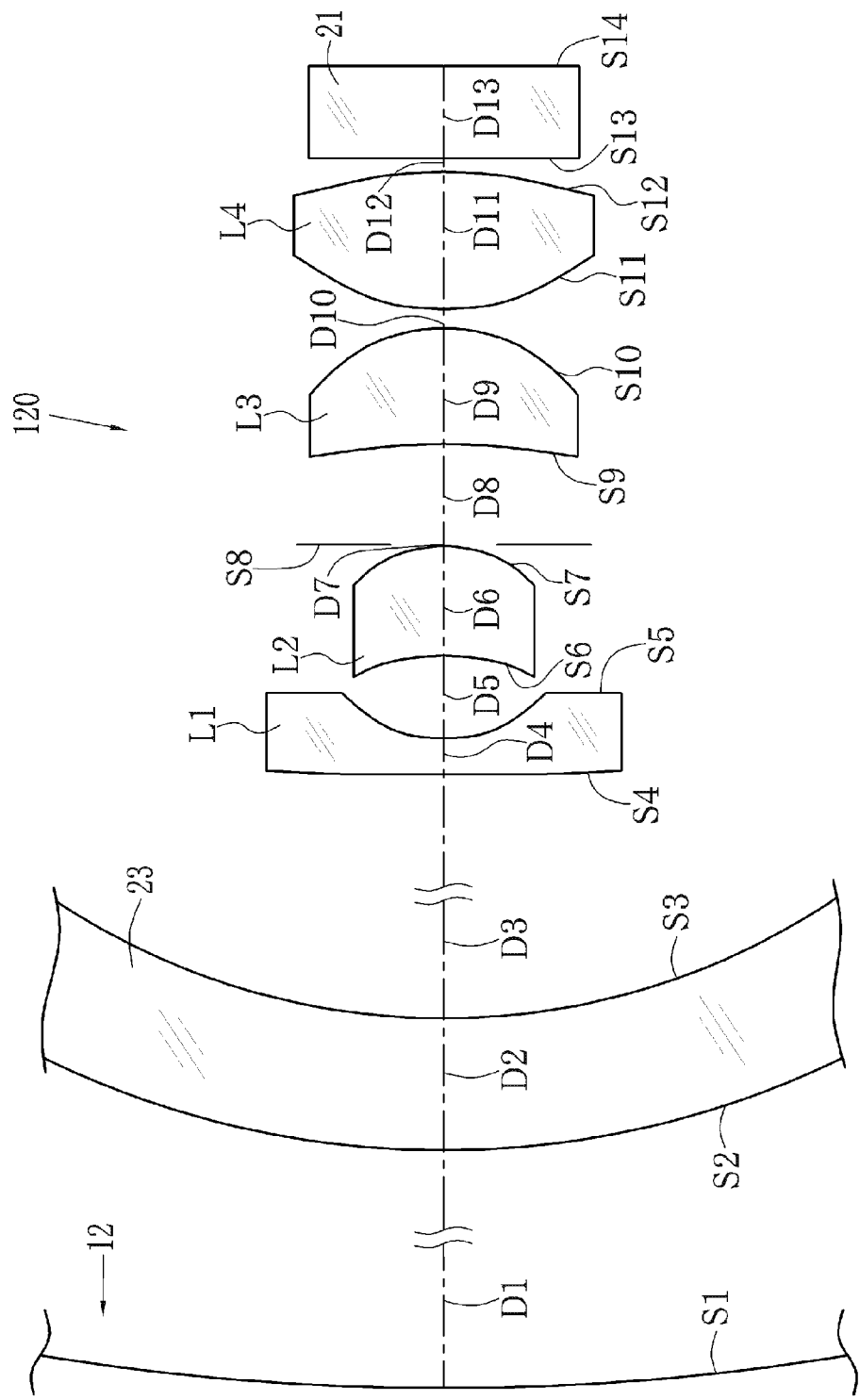
FIG. 36 is a lens configuration diagram of an image pickup optical system according to an eleventh embodiment of the present invention.
Figure 37:
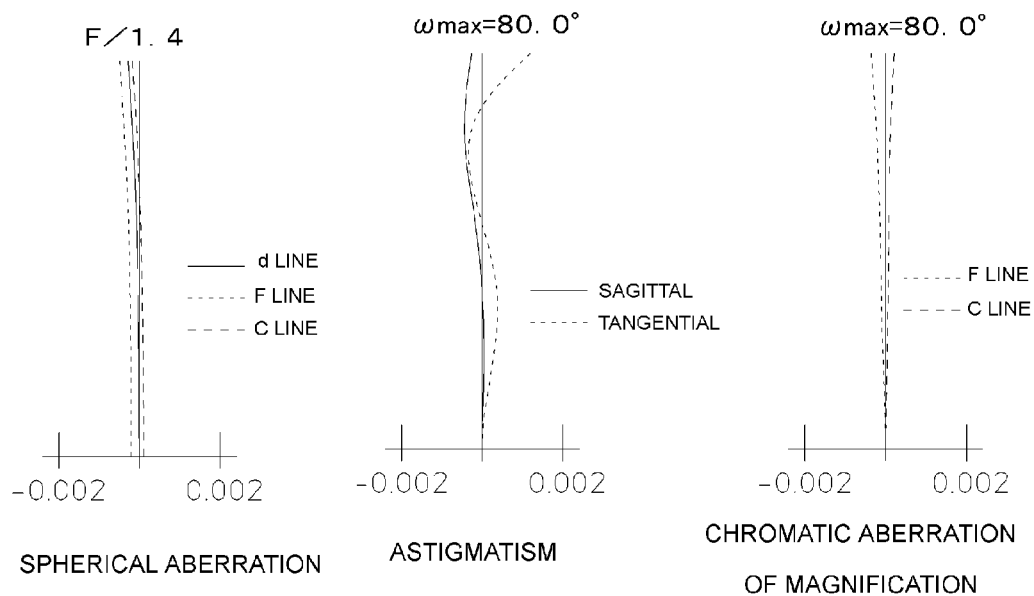
FIG. 37 is an aberration diagram of the image pickup optical system according to the eleventh embodiment.
Figure 38:
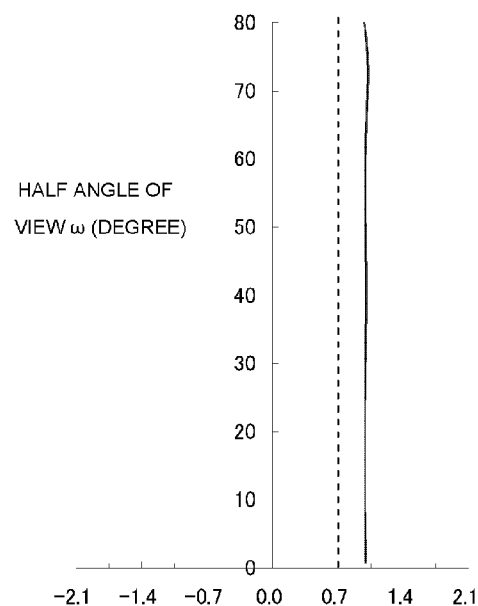
FIG. 38 is a graph showing distortion of the image pickup optical system according to the eleventh embodiment.

The configuration of an image pickup optical system 120 of Embodiment 11 is shown in FIG. 36. As in the case of the above Embodiments, Table 21 shows lens data, Table 22 shows data of aspherical surfaces, and FIG. 37 shows the spherical aberration, astigmatism, and chromatic aberration of magnification. Additionally, the graph illustrating the degree of the distortion based on the value of $(Y(\omega+\Delta\omega)-Y(\omega))/Y(\Delta\omega)$ is shown in FIG. 38.

TABLE 21 f = 1.0 Fno = 1.4 2ωmax = 160°

| SURFACE | RADIUS OF CURVATURE | SURFACE SEPARATION | $N_d$ | $\nu_d$ |
|---|---|---|---|---|
| OBJ | 28.2332 | 19.4022 | | |
| 2 | 10.1884 | 1.4572 | 1.57500 | 32.2 |
| 3 | 7.8196 | 6.2476 | | |
| 4* | −117.6982 | 0.3795 | 1.53039 | 55.2 |
| 5* | 1.5604 | 0.9144 | | |
| 6* | −3.3005 | 1.1967 | 1.53039 | 55.2 |
| 7* | −1.3610 | 0.0054 | | |
| APERTURE STOP | ∞ | 1.1230 | | |
| 9* | −4.3483 | 1.2890 | 1.53039 | 55.2 |
| 10* | −1.8179 | 0.1822 | | |
| 11* | 1.8940 | 1.5094 | 1.53039 | 55.2 |
| 12* | −4.3858 | 0.1714 | | |
| 13 | ∞ | 0.9927 | 1.55920 | 53.9 |
| 14 | ∞ | 0.0000 | | |
| IMG | ∞ | | | |

TABLE 22

| SURFACE | K | $A_3$ | $A_4$ | $A_5$ |
|---|---|---|---|---|
| 4 | −1.0000 | 6.4662E−03 | −1.0823E−03 | 1.2994E−03 |
| 5 | −1.0000 | 4.3222E−02 | 1.2853E−02 | 5.3203E−03 |
| 6 | −1.0000 | −5.0859E−03 | −3.4693E−02 | −1.3680E−02 |
| 7 | −1.0000 | 5.8988E−03 | −1.7335E−02 | 1.1859E−02 |
| 9 | −1.0000 | 2.1280E−02 | 4.9107E−03 | 2.8814E−02 |
| 10 | −1.0000 | −2.3316E−02 | 2.6397E−03 | 2.5619E−03 |
| 11 | −1.0000 | −2.7029E−02 | 5.8249E−03 | 2.6211E−04 |
| 12 | −1.0000 | 1.2528E−02 | −4.9044E−03 | 2.6159E−03 |

| SURFACE | $A_6$ | $A_7$ | $A_8$ | $A_9$ |
|---|---|---|---|---|
| 4 | 1.2777E−03 | −8.3443E−04 | −2.3103E−04 | 1.5397E−04 |
| 5 | −5.3685E−03 | −3.5806E−03 | 2.6181E−03 | 7.1885E−06 |
| 6 | −3.1221E−02 | −4.7545E−03 | −3.3105E−03 | −6.5527E−06 |
| 7 | −1.8205E−02 | 4.2313E−03 | −2.8733E−04 | 1.9037E−06 |
| 9 | −1.7732E−02 | 1.3438E−05 | −1.4280E−03 | 3.4946E−04 |
| 10 | 4.5554E−04 | −3.3893E−04 | −8.8711E−04 | −5.6674E−04 |
| 11 | −3.8849E−03 | 1.9742E−03 | 7.5091E−05 | −6.1615E−04 |
| 12 | −5.5300E−04 | −7.6048E−04 | 7.9145E−05 | 4.1644E−04 |

TABLE 22-continued

| SURFACE | $A_{10}$ | $A_{11}$ | $A_{12}$ | $A_{13}$ |
|---|---|---|---|---|
| 4 | 1.5083E−06 | 1.3272E−08 | 3.5637E−10 | 1.9565E−11 |
| 5 | 2.8852E−07 | 5.6322E−09 | 3.1396E−10 | 1.7236E−11 |
| 6 | −4.0152E−08 | 5.7187E−09 | 3.1396E−10 | 1.7236E−11 |
| 7 | 1.0417E−07 | 5.7187E−09 | 3.1396E−10 | 1.7236E−11 |
| 9 | 4.5382E−07 | 5.7187E−09 | 3.1396E−10 | 1.7236E−11 |
| 10 | 1.5669E−07 | 5.7187E−09 | 3.1396E−10 | 1.7236E−11 |
| 11 | 7.6879E−05 | 3.0862E−07 | 3.1680E−10 | 1.7236E−11 |
| 12 | 1.1190E−04 | 4.3744E−08 | 3.1388E−10 | 1.7236E−11 |

| SURFACE | $A_{14}$ | $A_{15}$ | $A_{16}$ | $A_{17}$ |
|---|---|---|---|---|
| 4 | 9.4627E−13 | 5.1950E−14 | 2.8521E−15 | 1.5658E−16 |
| 5 | 9.4627E−13 | 5.1950E−14 | 2.8521E−15 | 1.5658E−16 |
| 6 | 9.4627E−13 | 5.1950E−14 | 2.8521E−15 | 1.5658E−16 |
| 7 | 9.4627E−13 | 5.1950E−14 | 2.8521E−15 | 1.5658E−16 |
| 9 | 9.4627E−13 | 5.1950E−14 | 2.8521E−15 | 1.5658E−16 |
| 10 | 9.4627E−13 | 5.1950E−14 | 2.8521E−15 | 1.5658E−16 |
| 11 | 9.4627E−13 | 5.1950E−14 | 2.8521E−15 | 1.5658E−16 |
| 12 | 9.4627E−13 | 5.1950E−14 | 2.8521E−15 | 1.5658E−16 |

| SURFACE | $A_{18}$ | $A_{19}$ | $A_{20}$ |
|---|---|---|---|
| 4 | 8.5961E−18 | 4.7193E−19 | 2.5909E−20 |
| 5 | 8.5961E−18 | 4.7193E−19 | 2.5909E−20 |
| 6 | 8.5961E−18 | 4.7193E−19 | 2.5909E−20 |
| 7 | 8.5961E−18 | 4.7193E−19 | 2.5909E−20 |
| 9 | 8.5961E−18 | 4.7193E−19 | 2.5909E−20 |
| 10 | 8.5961E−18 | 4.7193E−19 | 2.5909E−20 |
| 11 | 8.5961E−18 | 4.7193E−19 | 2.5909E−20 |
| 12 | 8.5961E−18 | 4.7193E−19 | 2.5909E−20 |

In the image pickup optical system 120, the maximum angle of view is 160°, $\Delta Zr$ is 0.117, $\Delta Zp$ is 0.119, and $\Delta Zr/\Delta Zp$ is 0.981, which is out of the range of the mathematical expression 1. However, the maximum angle of view ($2\omega \max$) of the image pickup optical system 120 is at least 135°, and therefore if the image pickup optical system 120 satisfies the condition of the mathematical expression 2, the image of the object 12 including its central portion and peripheral portion can be within the depth of field. Further, as shown in FIG. 38, $(Y(\omega+\Delta\omega)-Y(\omega))/Y(\Delta\omega)$ is more than 0.7. Therefore, the image pickup optical system 120 also satisfies the condition of the mathematical expression 3, and it is possible to suppress the distortion to an acceptable level.

[Embodiment 12]

Figure 39:
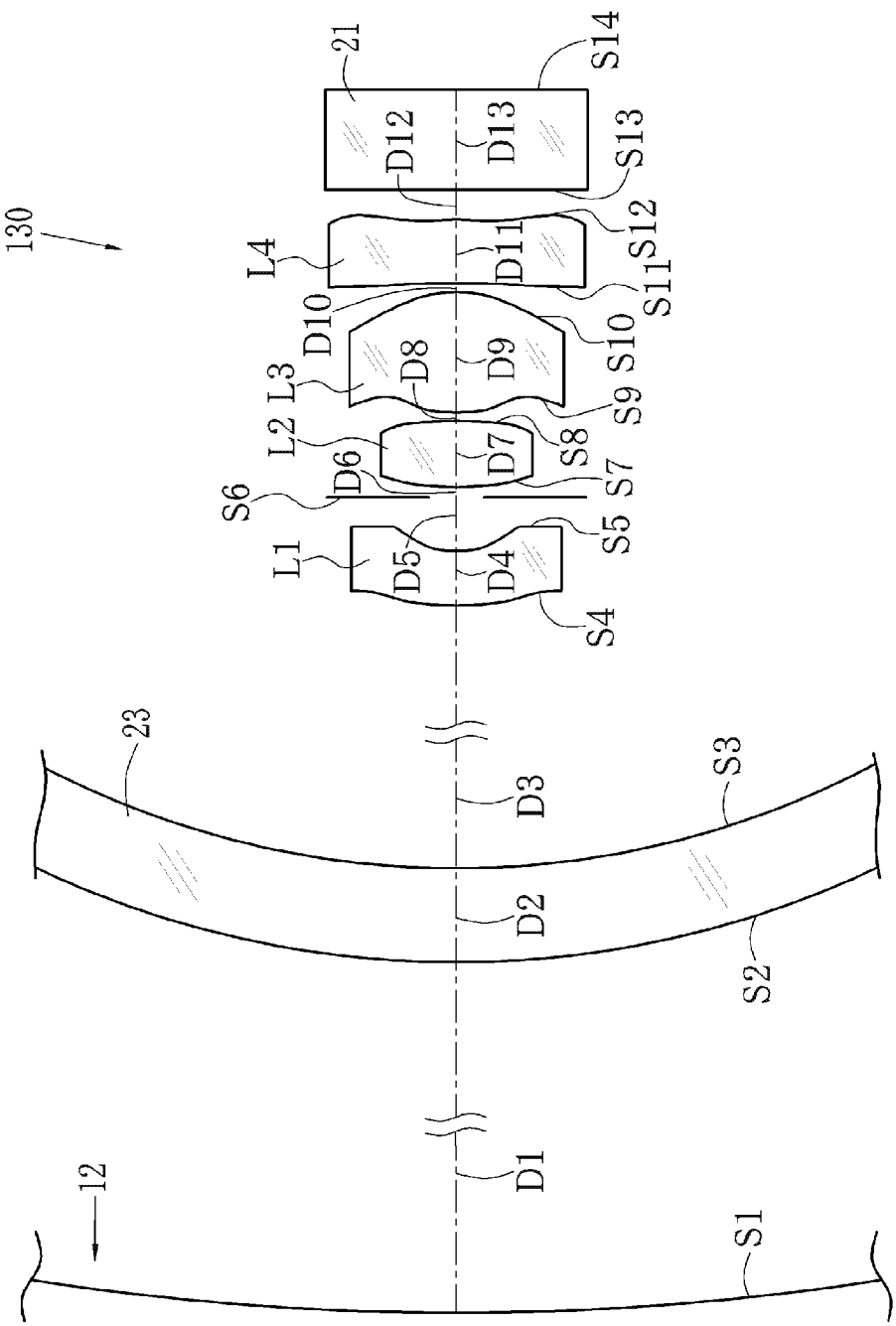
FIG. 39 is a lens configuration diagram of an image pickup optical system according to a twelfth embodiment of the present invention.
Figure 40:
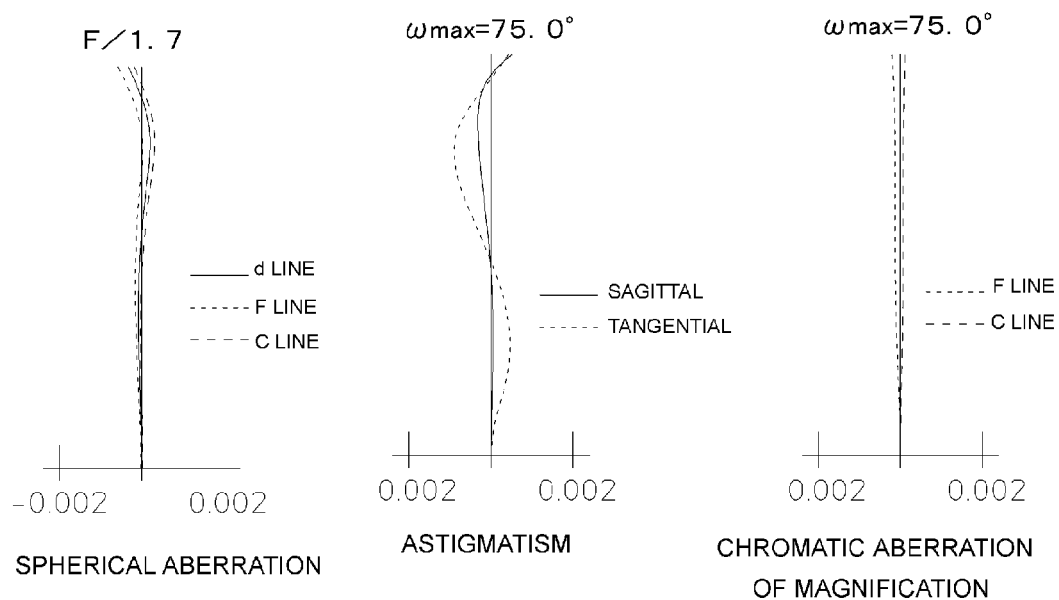
FIG. 40 is an aberration diagram of the image pickup optical system according to the twelfth embodiment.
Figure 41:
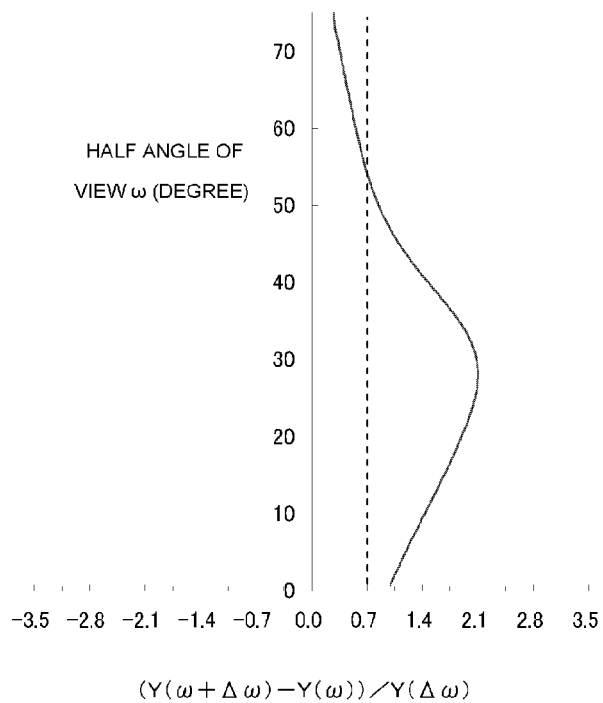
FIG. 41 is a graph showing distortion of the image pickup optical system according to the twelfth embodiment.

The configuration of an image pickup optical system 130 of Embodiment 12 is shown in FIG. 39. As in the case of the above Embodiments, Table 23 shows lens data, Table 24 shows data of aspherical surfaces, and FIG. 40 shows the spherical aberration, astigmatism, and chromatic aberration of magnification. Additionally, the graph illustrating the degree of the distortion based on the value of $(Y(\omega+\Delta\omega)-Y(\omega))/Y(\Delta\omega)$ is shown in FIG. 41.

TABLE 23 f = 1.0  Fno = 1.7  2ωmax = 150°

| SURFACE | RADIUS OF CURVATURE | SURFACE SEPARATION | $N_d$ | $v_d$ |
|---|---|---|---|---|
| OBJ | 34.3542 | 22.1640 | | |
| 2 | 12.1902 | 1.1082 | 1.58600 | 55.0 |
| 3 | 11.0820 | 11.0820 | | |
| 4* | −142.3518 | 0.6649 | 1.63178 | 23.2 |
| 5* | 0.9780 | 0.6649 | | |
| APERTURE STOP | ∞ | 0.1108 | | |
| 7* | 2.6830 | 0.7776 | 1.63178 | 23.2 |
| 8* | 2.1249 | 0.1108 | | |
| 9* | 0.7361 | 1.5045 | 1.49023 | 57.5 |
| 10* | −1.4812 | 0.1108 | | |
| 11* | −2.1419 | 0.7758 | 1.63178 | 23.2 |
| 12* | −1.2326 | 0.3369 | | |
| 13 | ∞ | 1.2079 | 1.55920 | 53.9 |
| 14 | ∞ | 0.0000 | | |
| IMG | ∞ | | | |

TABLE 24

| SURFACE | K | $A_3$ | $A_4$ | $A_5$ |
|---|---|---|---|---|
| 4 | −1.0000 | 2.5557E−01 | −7.9966E−02 | 1.0669E−01 |
| 5 | −1.0000 | −7.5229E−01 | 4.9965E+00 | −8.4921E+00 |
| 7 | −1.0000 | 2.4035E−01 | −1.6417E+00 | 4.3919E+00 |
| 8 | −1.0000 | −2.6174E−01 | −1.8006E−01 | −1.2237E+00 |
| 9 | −1.0000 | −9.6486E−01 | 1.7197E+00 | −1.9499E+00 |
| 10 | −1.0000 | −1.5172E−01 | 1.9389E−01 | −1.8857E−01 |
| 11 | −1.0000 | 4.4724E−01 | −3.6165E−01 | −5.8004E−03 |
| 12 | −1.0000 | 4.5402E−01 | 4.0102E−01 | −4.3849E−01 |

TABLE 24-continued

| SURFACE | $A_6$ | $A_7$ | $A_8$ | $A_9$ |
|---|---|---|---|---|
| 4 | −9.0104E−02 | −1.0062E−01 | −2.0955E−02 | 3.4790E−02 |
| 5 | 3.2770E+00 | 2.1598E+00 | −1.5407E+00 | 6.4680E−01 |
| 7 | −4.3015E+00 | −5.5651E+00 | 1.3940E+01 | 5.9263E−01 |
| 8 | 5.1226E+00 | −5.5367E+00 | −2.0503E+00 | 6.9866E+00 |
| 9 | −2.8688E+00 | 9.6102E+00 | −2.8151E+00 | −1.5372E+01 |
| 10 | 9.4593E−02 | 1.7075E−01 | −3.3295E−02 | −9.7080E−02 |
| 11 | 1.2899E−01 | −3.5795E−02 | −4.1157E−02 | 2.9275E−02 |
| 12 | −1.4621E−01 | 7.8715E−02 | 5.8889E−02 | 1.3945E−02 |

| SURFACE | $A_{10}$ | $A_{11}$ | $A_{12}$ | $A_{13}$ |
|---|---|---|---|---|
| 4 | 4.0433E−02 | 1.5542E−02 | −1.0541E−02 | −1.7026E−02 |
| 5 | 2.7222E+00 | −3.8597E+00 | 2.9405E−01 | 6.1719E−01 |
| 7 | −2.0418E+01 | 1.6047E+01 | −1.9003E+00 | −1.4448E+00 |
| 8 | −3.8309E+00 | 6.5949E−01 | −2.6596E−02 | −5.8372E−02 |
| 9 | 2.0573E+01 | −1.0293E+01 | 1.8423E+00 | 6.0120E−02 |
| 10 | 1.7761E−02 | −1.5813E−02 | −1.4972E−02 | 4.7029E−02 |
| 11 | 2.4140E−02 | −7.6758E−04 | −2.2347E−02 | 1.9912E−03 |
| 12 | −2.5645E−03 | −8.0562E−03 | −5.4726E−03 | −1.4975E−03 |

| SURFACE | $A_{14}$ | $A_{15}$ | $A_{16}$ | $A_{17}$ |
|---|---|---|---|---|
| 4 | 3.2111E−03 | 2.0588E−03 | 3.2114E−05 | −3.5101E−08 |
| 5 | 1.3215E−02 | 8.3660E−05 | 1.2917E−05 | 5.3212E−06 |
| 7 | 2.6873E−03 | −1.5880E−03 | −7.8824E−05 | −8.2243E−08 |
| 8 | 2.9629E−02 | 8.3852E−05 | 2.3942E−06 | −2.8086E−11 |
| 9 | −2.5181E−02 | 8.9775E−05 | −1.3247E−09 | −5.9765E−11 |
| 10 | −1.8587E−02 | 7.3900E−04 | −5.6077E−14 | −5.9713E−11 |
| 11 | 6.1478E−03 | −1.7187E−03 | 4.4605E−05 | 4.8021E−10 |
| 12 | 3.3380E−03 | −1.3232E−04 | −2.1244E−04 | −1.1737E−07 |

| SURFACE | $A_{18}$ | $A_{19}$ | $A_{20}$ |
|---|---|---|---|
| 4 | −1.7829E−08 | 3.4054E−09 | 2.0020E−10 |
| 5 | 7.8094E−09 | −6.0477E−15 | 7.7327E−16 |
| 7 | 1.6316E−12 | 5.3637E−13 | 7.9755E−16 |
| 8 | −2.7975E−12 | −1.1963E−13 | −4.6868E−15 |
| 9 | −2.6853E−12 | −1.1928E−13 | −4.6928E−15 |
| 10 | −2.6967E−12 | −1.2169E−13 | −5.3817E−15 |
| 11 | −1.1415E−16 | −5.1503E−18 | −5.4162E−18 |
| 12 | −1.1415E−16 | −5.1503E−18 | −5.4843E−15 |

In the image pickup optical system 130, the maximum angle of view is 150°, ΔZr is 0.078, ΔZp is 0.069, and ΔZr/ΔZp is 1.120. Since the maximum angle of view of the image pickup optical system 130 is at least 135°, it is sufficient that the condition of the mathematical expression 2 is satisfied. Therefore, the image of the object 12 including its central portion and peripheral portion can be within the depth of field. Further, as shown in FIG. 41, (Y(ω+Δω)−Y(ω))/Y(Δω) is more than 0.7. Therefore, the image pickup optical system 130 also satisfies the condition of the mathematical expression 3, and it is possible to suppress the distortion to an acceptable level.

[Embodiment 13]

Figure 42:
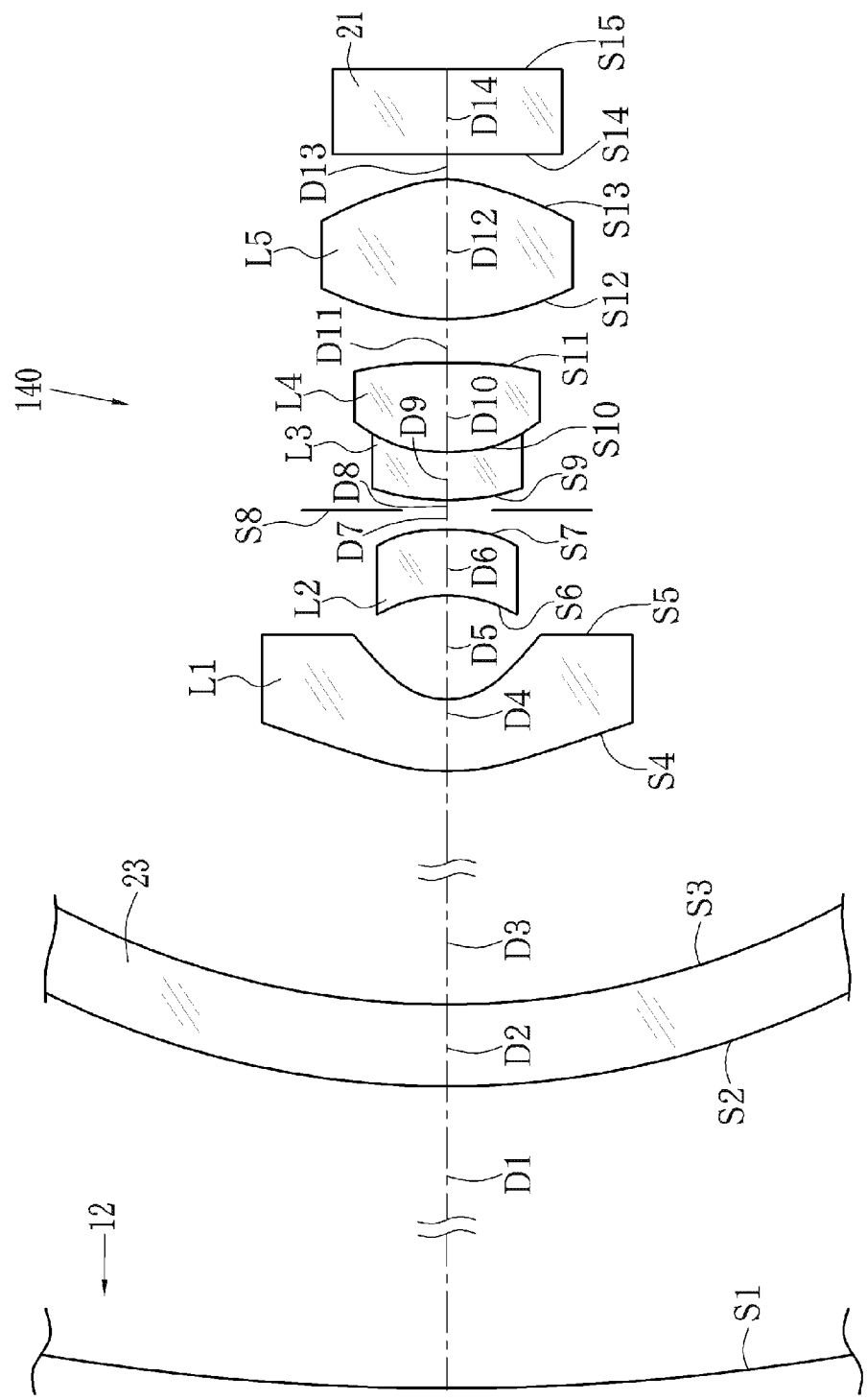
FIG. 42 is a lens configuration diagram of an image pickup optical system according to a thirteenth embodiment of the present invention.
Figure 43:
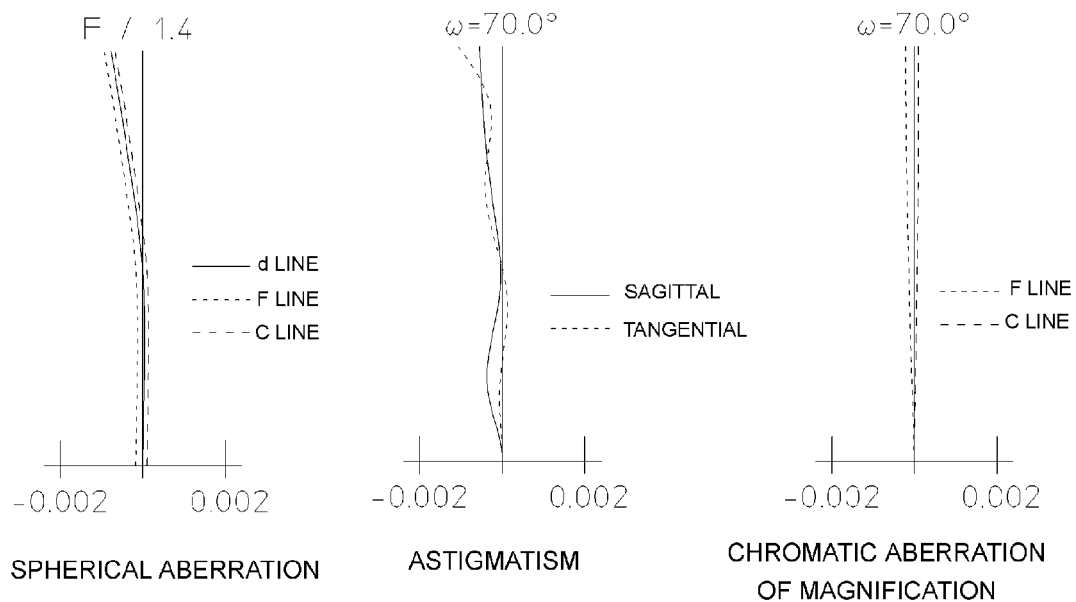
FIG. 43 is an aberration diagram of the image pickup optical system according to the thirteenth embodiment.
Figure 44:
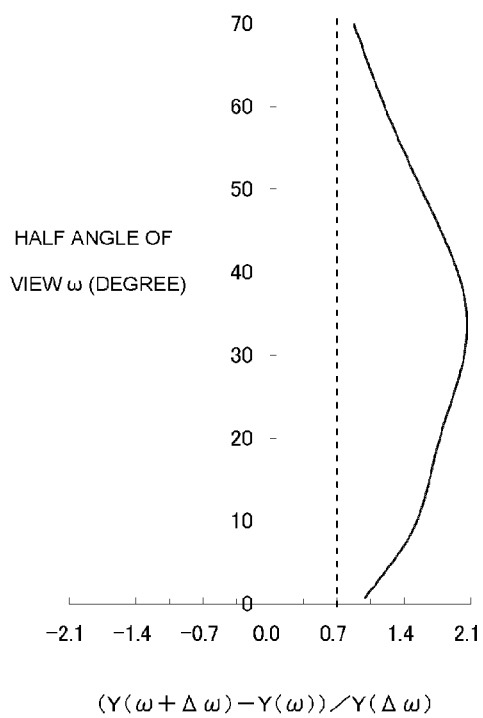
FIG. 44 is a graph showing distortion of the image pickup optical system according to the thirteenth embodiment.

The configuration of an image pickup optical system 140 of Embodiment 13 is shown in FIG. 42. As in the case of the above Embodiments, Table 25 shows lens data, Table 26 shows data of aspherical surfaces, and FIG. 43 shows the spherical aberration, astigmatism, and chromatic aberration of magnification. Additionally, the graph illustrating the degree of the distortion based on the value of (Y(+Δω)−Y(ω))/Y(Δω) is shown in FIG. 44.

TABLE 25 f = 1.0 Fno = 1.4 2ωmax = 140°

| SURFACE | RADIUS OF CURVATURE | SURFACE SEPARATION | $N_d$ | $v_d$ |
|---|---|---|---|---|
| OBJ | 46.6412 | 29.4893 | | |
| 2 | 17.1519 | 1.5046 | 1.58600 | 55.0 |
| 3 | 15.6474 | 15.0454 | | |
| 4* | 5.6650 | 1.3154 | 1.53039 | 55.2 |
| 5* | 0.9640 | 1.9412 | | |
| 6 | −2.5360 | 1.2129 | 1.83481 | 42.7 |
| 7 | −3.1101 | 0.3722 | | |
| APERTURE STOP | ∞ | 0.1505 | | |
| 9 | 4.8912 | 0.8689 | 1.84666 | 23.8 |
| 10 | 2.8994 | 1.6847 | 1.72916 | 54.7 |
| 11 | −10.9280 | 0.8151 | | |
| 12* | 3.9733 | 2.5848 | 1.53039 | 55.2 |
| 13* | −1.6180 | 0.5921 | | |
| 14 | ∞ | 1.5046 | 1.55920 | 53.9 |
| 15 | ∞ | 0.0000 | | |
| IMG | ∞ | | | |

TABLE 26

| SURFACE | K | $A_3$ | $A_4$ | $A_5$ |
|---|---|---|---|---|
| 4 | −1.0000 | 2.4676E−02 | −8.1846E−03 | −7.7721E−04 |
| 5 | −1.0000 | −4.4807E−01 | 6.1677E−01 | −2.1560E−01 |
| 12 | −1.0000 | −2.2403E−02 | 1.5209E−02 | −3.2990E−03 |
| 13 | −1.0000 | 7.7484E−02 | 8.8811E−03 | −1.2276E−03 |

| SURFACE | $A_6$ | $A_7$ | $A_8$ | $A_9$ |
|---|---|---|---|---|
| 4 | −3.9881E−05 | 1.4596E−05 | 8.1674E−06 | 2.8924E−06 |
| 5 | −1.8633E−01 | 1.0018E−01 | 8.1013E−02 | −9.0741E−02 |
| 12 | −1.8254E−04 | 2.2860E−05 | −2.9215E−05 | 1.1397E−07 |
| 13 | −4.5699E−04 | −9.8416E−05 | −7.8836E−05 | −2.8019E−05 |

| SURFACE | $A_{10}$ | $A_{11}$ | $A_{12}$ | $A_{13}$ |
|---|---|---|---|---|
| 4 | 7.3839E−07 | 1.2637E−07 | −1.4413E−08 | −3.0817E−08 |
| 5 | 4.0095E−02 | −9.4795E−03 | 1.7820E−04 | 3.5069E−04 |
| 12 | 4.9438E−06 | −3.8706E−06 | −1.8050E−06 | 1.4052E−07 |
| 13 | −2.4746E−06 | −1.0287E−06 | 6.2823E−08 | −3.9567E−08 |

| SURFACE | $A_{14}$ | $A_{15}$ | $A_{16}$ | $A_{17}$ |
|---|---|---|---|---|
| 4 | −3.1909E−08 | 1.4808E−08 | −1.5122E−09 | −5.6318E−11 |
| 5 | −2.3948E−05 | −2.0663E−07 | 8.0736E−11 | 1.0538E−21 |
| 12 | −2.7694E−07 | 1.3671E−07 | −1.1583E−10 | 6.3221E−11 |
| 13 | 1.3990E−07 | 6.4277E−08 | −1.4935E−08 | −6.0131E−12 |

| SURFACE | $A_{18}$ | $A_{19}$ | $A_{20}$ |
|---|---|---|---|
| 4 | 8.5521E−12 | 3.5661E−13 | −5.1576E−15 |
| 5 | −2.6589E−18 | −2.9992E−19 | −8.1304E−21 |
| 12 | 7.8895E−12 | −5.3503E−14 | −2.3142E−15 |
| 13 | 2.0056E−12 | −1.8060E−13 | −2.7019E−14 |

In the image pickup optical system 140, ΔZr is −0.036, ΔZp is 0.034, and ΔZr/ΔZp is −1.048. Since the maximum angle of view (2maxω) of the image pickup optical system 140 is 140°, it is sufficient that the condition of the mathematical expression 2 is satisfied. Therefore, the image of the object 12 including its central portion and peripheral portion can be within the depth of field. Further, as shown in FIG. 44, (Y(ω+Δω)−Y(ω))/Y(Δω) is more than 0.7. Therefore, the image pickup optical system 140 also satisfies the condition of the mathematical expression 3, and it is possible to suppress the distortion to an acceptable level, while the distortion is likely to appear in the peripheral portion.

[Embodiment 14]

Figure 45:
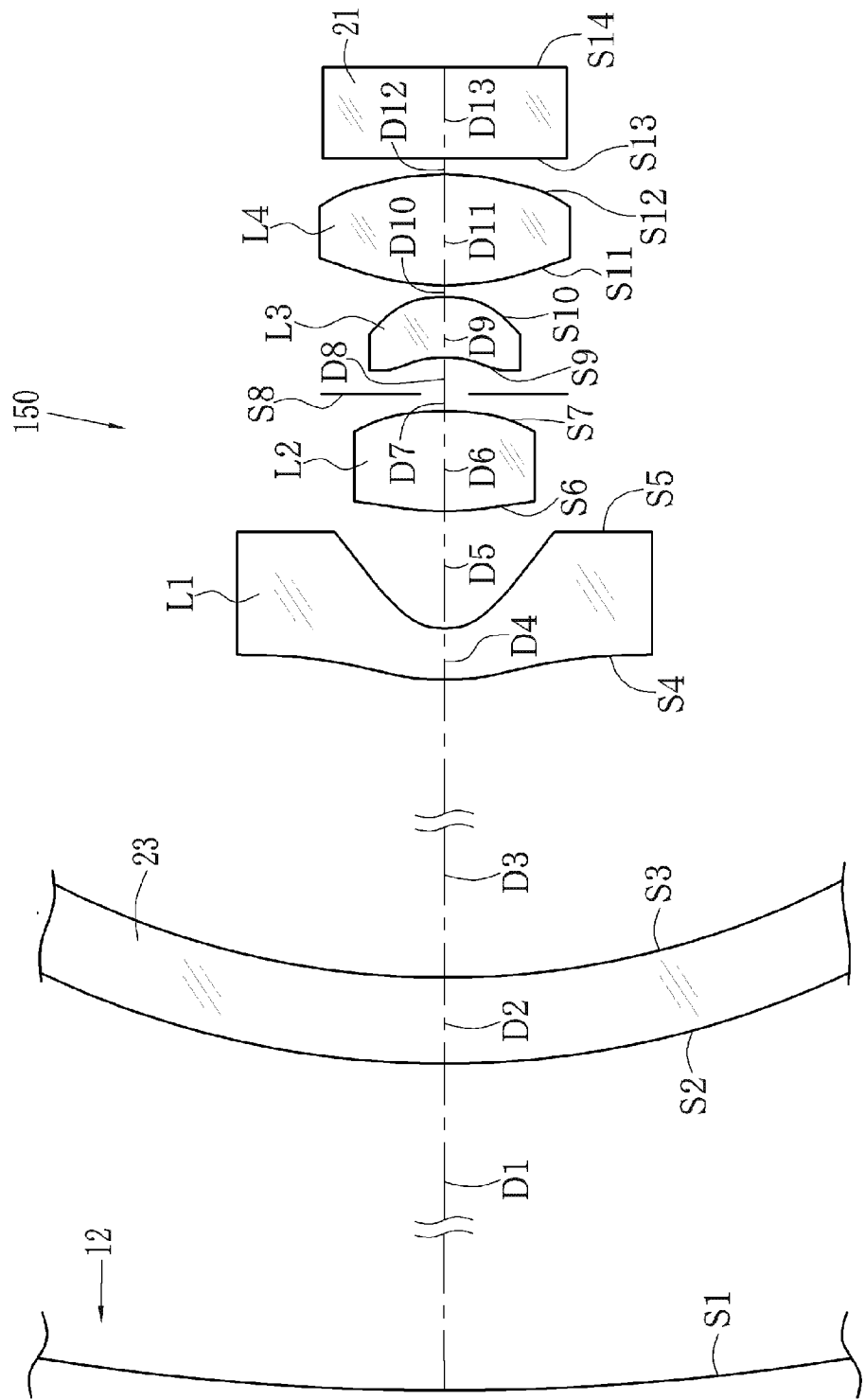
FIG. 45 is a lens configuration diagram of an image pickup optical system according to a fourteenth embodiment of the present invention.
Figure 46:
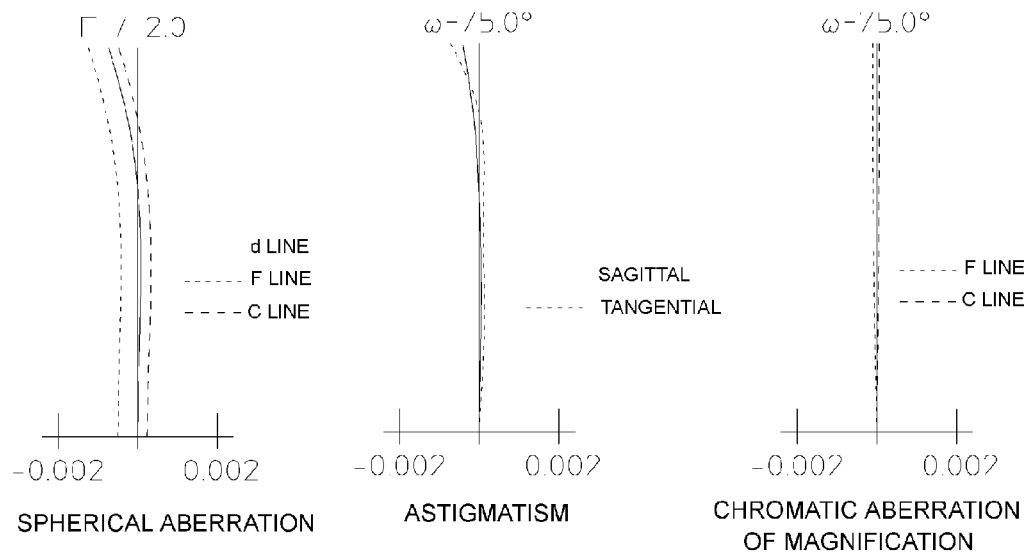
FIG. 46 is an aberration diagram of the image pickup optical system according to the fourteenth embodiment.
Figure 47:
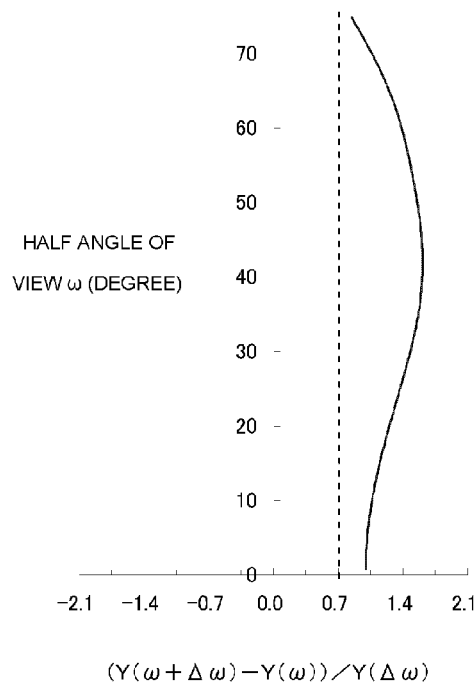
FIG. 47 is a graph showing distortion of the image pickup optical system according to the fourteenth embodiment.

The configuration of an image pickup optical system 150 of Embodiment 14 is shown in FIG. 45. As in the case of the above Embodiments, Table 27 shows lens data, Table 28 shows data of aspherical surfaces, and FIG. 46 shows the spherical aberration, astigmatism, and chromatic aberration of magnification. Additionally, the graph illustrating the degree of the distortion based on the value of (Y(ω+Δω)−Y(ω))/Y(Δω) is shown in FIG. 47.

TABLE 27 f = 1.0 Fno = 2.0 2ωmax = 150°

| SURFACE | RADIUS OF CURVATURE | SURFACE SEPARATION | $N_d$ | $v_d$ |
|---|---|---|---|---|
| OBJ | 39.1116 | 24.7286 | | |
| 2 | 14.3830 | 1.2617 | 1.58600 | 55.0 |
| 3 | 13.1213 | 12.6165 | | |
| 4* | 2.5983 | 0.7570 | 1.53039 | 55.2 |
| 5* | 0.6700 | 1.7472 | | |
| 6* | 3.8888 | 1.4805 | 1.65112 | 20.8 |
| 7* | −4.2960 | 0.2581 | | |
| APERTURE STOP | ∞ | 0.5254 | | |
| 9* | −2.5149 | 0.9367 | 1.54378 | 55.7 |
| 10* | −1.4944 | 0.1713 | | |
| 11* | 3.0622 | 1.6348 | 1.54378 | 55.7 |
| 12* | −3.3309 | 0.3740 | | |
| 13 | ∞ | 1.2617 | 1.55920 | 53.9 |
| 14 | ∞ | 0.0000 | | |
| IMG | ∞ | | | |

TABLE 28

| SURFACE | K | $A_3$ | $A_4$ | $A_5$ |
|---|---|---|---|---|
| 4 | −1.0000 | −7.0949E−02 | 2.6436E−03 | 1.1982E−03 |
| 5 | −1.0000 | −1.9524E−01 | 1.0890E−01 | −3.1541E−02 |
| 6 | −1.0000 | −4.6955E−02 | 1.0027E−01 | −1.2395E−01 |
| 7 | −1.0000 | −2.8435E−02 | 1.0106E−01 | −9.8759E−02 |
| 9 | −1.0000 | −3.8830E−02 | 5.8665E−02 | −3.3679E−01 |
| 10 | −1.0000 | 2.1049E−02 | −9.8121E−02 | −5.2708E−02 |
| 11 | −1.0000 | 5.0913E−02 | −1.1043E−01 | 6.2833E−03 |
| 12 | −1.0000 | 2.0349E−02 | 1.2216E−01 | −9.1841E−02 |

TABLE 28-continued

| SURFACE | $A_6$ | $A_7$ | $A_8$ | $A_9$ |
|---|---|---|---|---|
| 4 | 1.0817E-04 | -7.4701E-07 | -6.1587E-06 | -9.4155E-07 |
| 5 | -1.4199E-02 | -5.0886E-04 | 1.4185E-03 | 6.6602E-04 |
| 6 | 2.6934E-02 | 2.7848E-02 | -4.3172E-03 | -6.9136E-03 |
| 7 | -1.4502E-01 | 1.6489E-01 | 1.1418E-01 | -9.6373E-02 |
| 9 | 4.0474E-01 | 3.4398E-01 | -1.6802E+00 | 1.9344E+00 |
| 10 | 2.3560E-02 | 3.2595E-02 | 9.5777E-03 | -1.9910E-02 |
| 11 | 4.4177E-02 | -9.8649E-03 | -8.5029E-03 | 2.9868E-03 |
| 12 | -2.1712E-02 | 1.5465E-02 | 5.7070E-03 | 4.9041E-05 |

| SURFACE | $A_{10}$ | $A_{11}$ | $A_{12}$ | $A_{13}$ |
|---|---|---|---|---|
| 4 | -9.8605E-08 | 4.1903E-09 | 7.0984E-09 | 1.8698E-09 |
| 5 | 2.4417E-04 | 1.1144E-06 | -5.1744E-05 | -3.5573E-05 |
| 6 | -2.1159E-03 | 3.3713E-04 | -2.8675E-04 | 5.1859E-04 |
| 7 | -1.7127E-01 | 1.9418E-01 | -5.8590E-02 | 1.4298E-03 |
| 9 | -1.0255E+00 | 2.9017E-01 | 4.2899E-02 | -6.2657E-02 |
| 10 | 3.1645E-04 | 1.2392E-03 | 2.9498E-03 | 1.8471E-03 |
| 11 | 2.3984E-03 | 5.4571E-06 | -1.7626E-03 | 2.4514E-04 |
| 12 | -1.6938E-04 | -3.2234E-04 | -2.2391E-04 | -1.2641E-04 |

| SURFACE | $A_{14}$ | $A_{15}$ | $A_{16}$ | $A_{17}$ |
|---|---|---|---|---|
| 4 | 2.0378E-10 | 6.9033E-11 | -2.2709E-11 | -6.6762E-12 |
| 5 | 2.4435E-07 | 3.8157E-06 | 3.9818E-07 | 2.1441E-07 |
| 6 | 1.9055E-04 | -7.4627E-05 | -2.9403E-06 | -2.4613E-09 |
| 7 | 1.0553E-03 | 3.8930E-06 | 8.9134E-08 | -7.7981E-11 |
| 9 | 4.5990E-03 | 8.6106E-10 | -4.9416E-11 | -1.7909E-12 |
| 10 | -1.0435E-03 | -1.6559E-06 | -1.4093E-10 | -1.7889E-12 |
| 11 | 3.7410E-04 | -1.0246E-04 | -6.2740E-08 | 1.1976E-11 |
| 12 | 1.1258E-04 | 5.0652E-06 | -6.0662E-06 | -1.0767E-09 |

| SURFACE | $A_{18}$ | $A_{19}$ | $A_{20}$ |
|---|---|---|---|
| 4 | -2.8483E-12 | 1.4725E-13 | 2.6989E-13 |
| 5 | 1.8432E-10 | -5.9132E-14 | -3.6062E-21 |
| 6 | 3.6838E-14 | -2.2143E-14 | 3.5417E-19 |
| 7 | -6.7323E-14 | -2.3482E-15 | -8.4759E-17 |
| 9 | -6.4623E-14 | -2.7919E-15 | -1.0149E-16 |
| 10 | -6.4884E-14 | -2.3514E-15 | -8.4851E-17 |
| 11 | -3.0546E-13 | -7.0885E-14 | 9.3052E-16 |
| 12 | 2.8315E-13 | -7.3306E-15 | -2.7237E-15 |

In the image pickup optical system 150, ΔZr is -0.034, ΔZp is 0.060, and ΔZr/ΔZp is -0.566. Since the maximum angle of view (2maxω) of the image pickup optical system 150 is 150°, it is sufficient that the condition of the mathematical expression 2 is satisfied. Therefore, the image of the object 12 including its central portion and peripheral portion can be within the depth of field. Further, as shown in FIG. 47, (Y(ω+Δω)-Y(ω))/Y(Δω) is more than 0.7. Therefore, the image pickup optical system 150 also satisfies the condition of the mathematical expression 3, and it is possible to suppress the distortion to an acceptable level, while the distortion is likely to appear in the peripheral portion.

[Embodiment 15]

Figure 48:
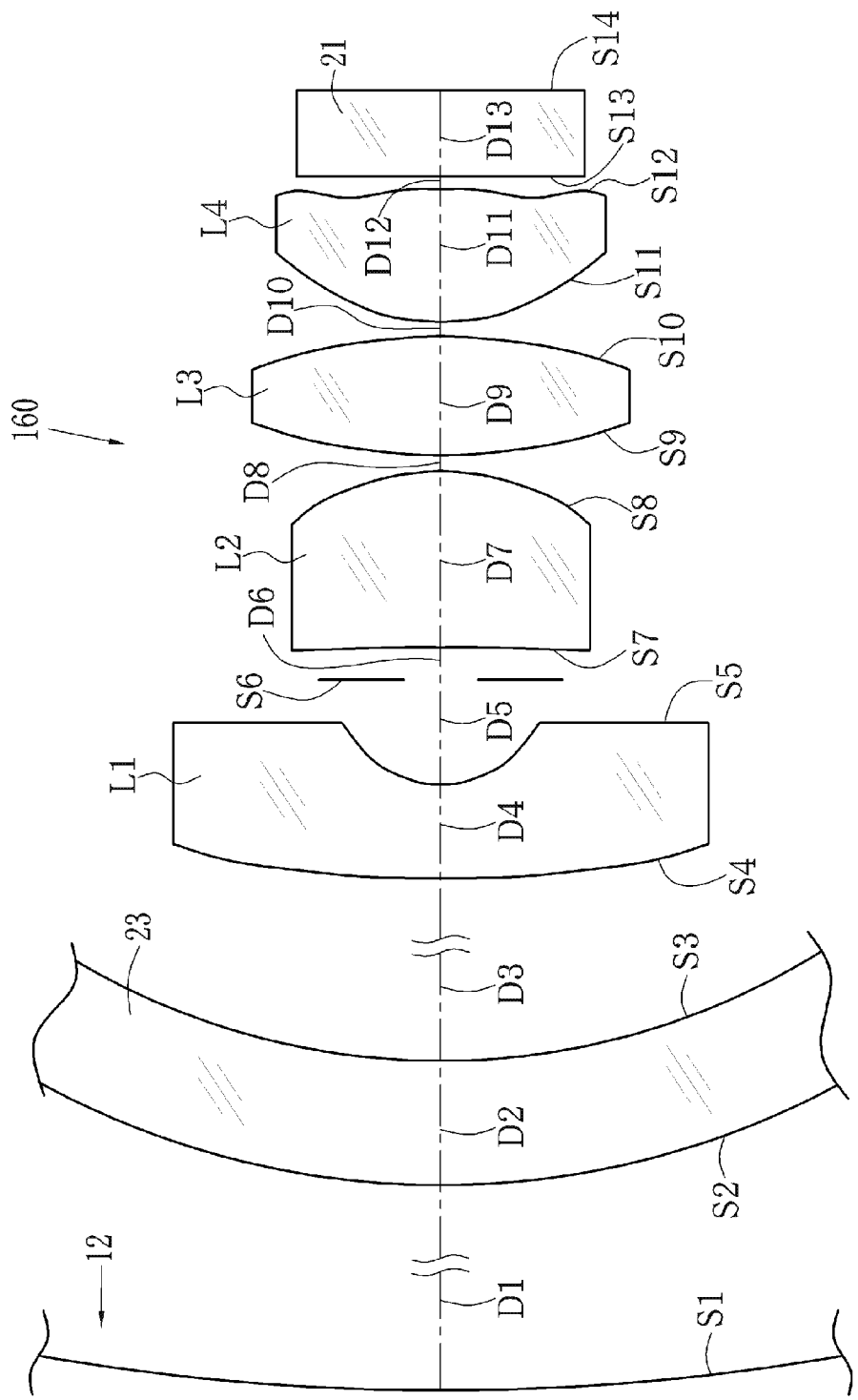
FIG. 48 is a lens configuration diagram of an image pickup optical system according to a fifteenth embodiment of the present invention.
Figure 49:
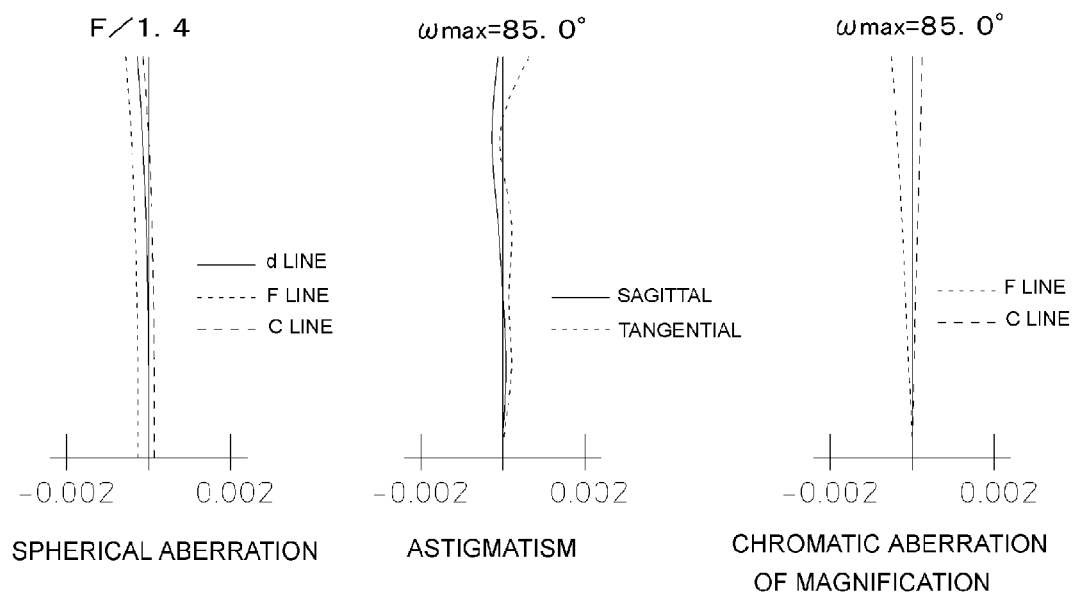
FIG. 49 is an aberration diagram of the image pickup optical system according to the fifteenth embodiment.
Figure 50:
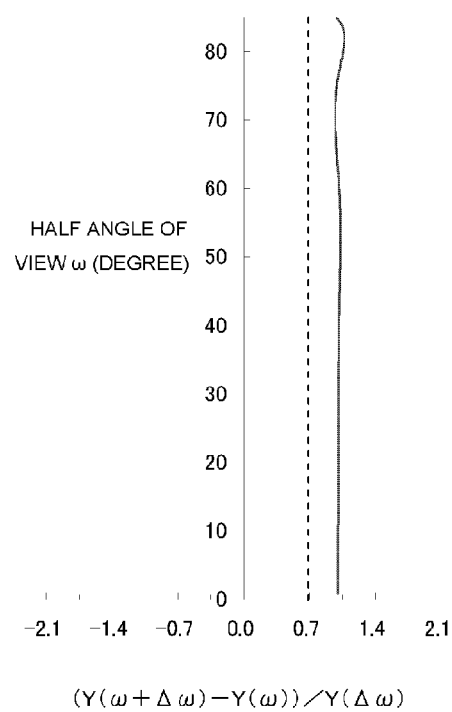
FIG. 50 is a graph showing distortion of the image pickup optical system according to the fifteenth embodiment.

The configuration of an image pickup optical system 160 of Embodiment 15 is shown in FIG. 48. As in the case of the above Embodiments, Table 29 shows lens data, Table 30 shows data of aspherical surfaces, and FIG. 49 shows the spherical aberration, astigmatism, and chromatic aberration of magnification. Additionally, the graph illustrating the degree of the distortion based on the value of (Y(ω+Δω)-Y(ω))/Y(Δω) is shown in FIG. 50.

TABLE 29 f = 1.0 Fno = 1.4 2ωmax = 170°

| SURFACE | RADIUS OF CURVATURE | SURFACE SEPARATION | $N_d$ | $v_d$ |
|---|---|---|---|---|
| OBJ | 29.0057 | 16.9570 | | |
| 2 | 10.2579 | 1.4971 | 1.57500 | 32.2 |
| 3 | 8.7517 | 5.8627 | | |
| 4* | 21.0846 | 1.1291 | 1.53039 | 55.2 |
| 5* | 1.2635 | 1.2642 | | |
| APERTURE STOP | ∞ | 0.3829 | | |
| 7 | -21.3026 | 2.1301 | 1.80400 | 46.6 |
| 8 | -3.0244 | 0.1873 | | |
| 9 | 7.5453 | 1.4255 | 1.80400 | 46.6 |
| 10 | -7.1995 | 0.1865 | | |
| 11* | 2.6921 | 1.5813 | 1.53039 | 55.2 |
| 12* | -4.0858 | 0.1806 | | |
| 13 | ∞ | 1.0199 | 1.55920 | 53.9 |
| 14 | ∞ | 0.0000 | | |
| IMG | ∞ | | | |

TABLE 30

| SURFACE | K | $A_3$ | $A_4$ | $A_5$ |
|---|---|---|---|---|
| 4 | −1.0000 | 1.1806E−03 | 6.0847E−04 | 1.1648E−04 |
| 5 | −1.0000 | 3.0189E−02 | 2.9023E−02 | −1.1704E−03 |
| 11 | −1.0000 | 6.2958E−03 | −6.0490E−03 | 3.8647E−03 |
| 12 | −1.0000 | 4.0413E−02 | 1.1306E−02 | 2.8963E−03 |

| SURFACE | $A_6$ | $A_7$ | $A_8$ | $A_9$ |
|---|---|---|---|---|
| 4 | 1.1526E−05 | −3.1849E−07 | −5.5674E−07 | −1.9003E−07 |
| 5 | −1.1450E−04 | 3.8652E−03 | 4.5996E−03 | 3.2054E−03 |
| 11 | 1.3835E−03 | 9.1107E−05 | −1.2677E−04 | −7.7351E−05 |
| 12 | 1.6035E−03 | 9.4610E−04 | 4.0676E−04 | 9.5714E−05 |

| SURFACE | $A_{10}$ | $A_{11}$ | $A_{12}$ | $A_{13}$ |
|---|---|---|---|---|
| 4 | −4.4059E−08 | −6.2540E−09 | 3.8526E−10 | 6.0256E−10 |
| 5 | 1.5331E−03 | 4.4516E−04 | −5.1892E−05 | −2.0610E−04 |
| 11 | −2.3361E−05 | −8.6265E−08 | 5.3226E−06 | 4.3320E−06 |
| 12 | −3.5343E−05 | −6.5696E−05 | −5.5364E−05 | −3.5172E−05 |

| SURFACE | $A_{14}$ | $A_{15}$ | $A_{16}$ | $A_{17}$ |
|---|---|---|---|---|
| 4 | 1.8528E−10 | 1.0491E−11 | −3.7667E−12 | −6.3129E−13 |
| 5 | −2.1831E−04 | −1.9444E−04 | −3.3983E−05 | −2.3424E−07 |
| 11 | 2.3286E−06 | 8.4037E−07 | 3.8252E−08 | −2.8889E−07 |
| 12 | −1.7641E−05 | −5.8258E−06 | 8.5904E−07 | 3.9596E−06 |

| SURFACE | $A_{18}$ | $A_{19}$ | $A_{20}$ |
|---|---|---|---|
| 4 | −1.3027E−13 | −2.5007E−15 | 3.8559E−15 |
| 5 | −1.2454E−07 | 0.0000E+00 | 3.9978E−20 |
| 11 | −3.6116E−07 | −1.7141E−08 | 0.0000E+00 |
| 12 | 1.5778E−07 | 0.0000E+00 | 0.0000E+00 |

In the image pickup optical system 160, $\Delta Zr$ is −0.018, $\Delta Zp$ is 0.202, and $\Delta Zr/\Delta Zp$ is −0.088. Although the maximum angle of view ($2max\omega$) of the image pickup optical system 160 is 170°, both of the mathematical expressions 1 and 2 are satisfied. Therefore, the image of the object 12 including its central portion and peripheral portion can be within the depth of field. Further, as shown in FIG. 50, $(Y(\omega+\Delta\omega)-Y(\omega))/Y(\Delta\omega)$ is more than 0.7. Therefore, the image pickup optical system 160 also satisfies the condition of the mathematical expression 3, and it is possible to suppress the distortion to an acceptable level, while the distortion is likely to appear in the peripheral portion.

[Comparative Embodiment 1]

An image of a spherical object surface is captured with its center at an entrance pupil position of an image pickup lens through a transparent cover having no optical power by an image pickup optical system shown in "appended optical system data 1" of the Patent Document 2. As a result, $\Delta Zr$ is −0.109, and $\Delta Zp$ is 0.016. Accordingly, although the maximum angle of view is less than 120° in this image pickup optical system, $\Delta Zr/\Delta Zp$ is −6.683, which is outside the range of the mathematical expression 1. Therefore, the position of the real image surface with respect to the light flux of $2\omega max$ is significantly deviated toward the object side in comparison with the position of the real image surface with respect to the light flux of $\omega max$, and part of the image obtained by the image capturing is outside of the depth of field. Thus, it becomes impossible to achieve preferable image forming.

[Comparative Embodiment 2]

In the similar manner, an image of a spherical object surface is captured with its center at an entrance pupil position of an image pickup lens through a transparent cover having no optical power by an image pickup optical system shown in "appended optical system data 2" of the Patent Document 2. As a result, $\Delta Zr$ is −0.010, and $\Delta Zp$ is 0.017. Accordingly, although the maximum angle of view is less than 120°, $\Delta Zr/\Delta Zp$ is −0.594, which is also outside the range of the mathematical expression 1. Therefore, the position of the real image surface with respect to the light flux of $2\omega max$ is significantly deviated toward the object side in comparison with the position of the real image surface with respect to the light flux of $\omega max$, and part of the image obtained by the image capturing is outside of the depth of field. Thus, it becomes impossible to achieve preferable image forming.

[Comparative Embodiment 3]

In the similar manner, an image of a spherical object surface is captured with its center at an entrance pupil position of an image pickup lens through a transparent cover having no optical power by an image pickup optical system shown in "appended optical system data 3" of the Patent Document 2. As a result, $\Delta Zr$ is −0.158, and $\Delta Zp$ is 0.015. Accordingly, although the maximum angle of view is less than 120°, $\Delta Zr/\Delta Zp$ is −10.849, which is outside the range of the mathematical expression 1. Therefore, the position of the real image surface with respect to the light flux of $2\omega max$ is significantly deviated toward the object side in comparison with the position of the real image surface with respect to the light flux of $\omega max$, and part of the image obtained by the image capturing is outside of the depth of field. Thus, it becomes impossible to achieve preferable image forming.

[Comparative Embodiment 4]

In the similar manner, also in the case of using an image pickup optical system shown in "appended optical system data 4" of the Patent Document 2, $\Delta Zr$ is −0.024, $\Delta Zp$ is 0.035, and $\Delta Zr/\Delta Zp$ is −0.687. Accordingly, although the maximum angle of view is less than 120°, the mathematical expression 1 is not satisfied. Therefore, the position of the real image surface with respect to the light flux of $2\omega max$ is significantly deviated toward the object side in comparison with the position of the real image surface with respect to the light flux of ωmax. As a result, part of the image obtained by the image capturing is outside of the depth of field. Thus, it becomes impossible to achieve preferable image forming.

[Comparative Embodiment 5]

In the similar manner, in the case of using an image pickup optical system shown in "appended optical system data 1" of the Patent Document 3, $\Delta Zr$ is −0.021, $\Delta Zp$ is 0.031, and $\Delta Zr/\Delta Zp$ is −0.691. Accordingly, although the maximum angle of view is less than 120°, the mathematical expression 1 is not satisfied. Therefore, the position of the real image surface with respect to the light flux of 2ωmax is significantly deviated toward the object side in comparison with the position of the real image surface with respect to the light flux of ωmax, and it becomes impossible to achieve preferable image forming.

[Comparative Embodiment 6]

In the similar manner, in the case of using an image pickup optical system shown in "appended optical system data 2" of the Patent Document 3, $\Delta Zr$ is −0.024 and $\Delta Zp$ is 0.036. Accordingly, although the maximum angle of view is less than 120°, $\Delta Zr/\Delta Zp$ is −0.666, which is outside the range of the mathematical expression 1. Therefore, the position of the real image surface with respect to the light flux of 2ωmax is significantly deviated toward the object side in comparison with the position of the real image surface with respect to the light flux of ωmax, and it becomes impossible to achieve preferable image forming.

DESCRIPTION OF THE REFERENCE NUMERALS

10: CAPSULE ENDOSCOPE
20: IMAGE PICKUP OPTICAL SYSTEM
L1: FIRST LENS
L2: SECOND LENS
L3: THIRD LENS
L4: FOURTH LENS
L5: FIFTH LENS

The invention claimed is:

1. An image pickup optical system for use in a capsule endoscope, which is accommodated in a capsule to be swallowed into a body and used to capture an image inside a body cavity through a dome-shaped powerless transparent cover constituting part of said capsule, said image pickup optical system satisfying a condition expressed by:

$$-5.0 \leq \Delta Zr/\Delta Zp \leq 5.0$$

when said image pickup optical system is disposed in front of an object in the shape of concave curved surface and image capturing is performed, wherein said $\Delta Zr$ denotes a difference between a position of a real image surface with respect to light flux of a maximum angle of view 2ωmax and a position of said real image surface with respect to light flux of a half angle of view ωmax, and A $\Delta Zp$ denotes a difference between a paraxial image forming position of a virtual object plane surface passing through an intersection point of said object and principal rays of 2ωmax and being vertical to an optical axis and a paraxial image forming position of a virtual object plane surface passing through an intersection point of said object and principal rays of ωmax and being vertical to said optical axis.

2. The image pickup optical system for use in a capsule endoscope described in claim 1, wherein said maximum angle of view 2ωmax is at least 135°.

3. The image pickup optical system for use in a capsule endoscope described in claim 1, wherein said maximum angle of view 2ωmax is at least 120° and a condition expressed by $-0.5 \leq \Delta Zr/\Delta Zp \leq 0.5$ is satisfied.

4. The image pickup optical system for use in a capsule endoscope described in claim 2, wherein a condition expressed by:

$$0.7 < (Y(\omega+\Delta\omega) - Y(\omega))/Y(\Delta\omega)$$

is satisfied, wherein $Y(\Delta\omega)$ denotes an image height at an arbitrary angle of view ω, and $\Delta\omega$ denotes an amount of slight change in said arbitrary angle of view ω.

5. The image pickup optical system for use in a capsule endoscope described in claim 1, wherein a negative lens which is convex toward said object is disposed at a position nearest to said object, a positive lens is disposed at a position nearest to an image surface, and at least a surface of said negative lens at a side nearer to said image surface and one of surfaces of said positive lens are aspherical.

6. The image pickup optical system for use in a capsule endoscope described in claim 5, wherein a positive lens group constituted by a plurality of lenses and having a positive power as a whole is disposed at a side nearer to said image surface than said negative lens, and a lens located at a position nearest to said object and a lens located at a position nearest to said image surface among said positive lens group are positive lenses.

* * * * *